(12) United States Patent
Foster et al.

(10) Patent No.: US 10,896,627 B2
(45) Date of Patent: Jan. 19, 2021

(54) INJECTION SITE TRAINING SYSTEM

(71) Applicant: Truinject Corp., Newport Beach, CA (US)

(72) Inventors: Clark B. Foster, Mission Viejo, CA (US); Gabrielle A. Rios, Newport Beach, CA (US); Bruce A. Christie, Clairmont, CA (US); Khoi Turner, Tustin, CA (US)

(73) Assignee: Truinjet Corp., Irvine, CA (US)

( * ) Notice: Subject to any disclaimer, the term of this patent is extended or adjusted under 35 U.S.C. 154(b) by 233 days.

(21) Appl. No.: 15/886,363

(22) Filed: Feb. 1, 2018

(65) Prior Publication Data

US 2018/0240365 A1    Aug. 23, 2018

Related U.S. Application Data

(63) Continuation of application No. 14/598,614, filed on Jan. 16, 2015, now Pat. No. 9,922,578.

(60) Provisional application No. 61/928,915, filed on Jan. 17, 2014, provisional application No. 61/939,093, (Continued)

(51) Int. Cl.
*G09B 23/28* (2006.01)
*G09B 23/30* (2006.01)
*A61M 5/31* (2006.01)

(52) U.S. Cl.
CPC .............. *G09B 23/285* (2013.01); *A61M 5/31* (2013.01); *G09B 23/30* (2013.01); *A61M 2205/33* (2013.01); *A61M 2205/332* (2013.01); *A61M 2205/3306* (2013.01); *A61M 2205/50* (2013.01);

(Continued)

(58) Field of Classification Search
CPC ....... G09B 23/28; G09B 23/285; G09B 23/30
See application file for complete search history.

(56) References Cited

U.S. PATENT DOCUMENTS

| | | |
|---|---|---|
| 3,237,340 A | 3/1966 | Knott |
| 3,722,108 A | 3/1973 | Chase |
| 3,941,121 A | 3/1976 | Olinger et al. |

(Continued)

FOREIGN PATENT DOCUMENTS

| | | |
|---|---|---|
| AU | 2011218649 B2 | 9/2011 |
| AU | 2015255197 A1 | 12/2015 |

(Continued)

OTHER PUBLICATIONS

"B-Smart disposable manometer for measuring peripheral nerve block injection pressures", Bbraun USA, 2016, in 4 pages.

(Continued)

*Primary Examiner* — Eddy Saint-Vil
(74) *Attorney, Agent, or Firm* — Knobbe, Martens, Olson & Bear, LLP

(57) ABSTRACT

An injection apparatus and training system for prophylactic, curative, therapeutic, acupuncture, or cosmetic injection training and certification. In an embodiment, an injection training system is described that includes a testing tool having a needle and a position sensor, where the position sensor is configured to obtain position information of the testing tool. The system also includes an injection apparatus configured to receive a simulated injection by the testing tool. The system includes a display device configured to receive the position information and to display position data reflective of the position information.

21 Claims, 31 Drawing Sheets

Related U.S. Application Data filed on Feb. 12, 2014, provisional application No. 62/066,792, filed on Oct. 21, 2014.

(52) U.S. Cl.
CPC ..... *A61M 2205/8206* (2013.01); *G09B 23/28* (2013.01)

(56) References Cited

U.S. PATENT DOCUMENTS

| | | | |
|---|---|---|---|
| 4,142,517 A | 3/1979 | Contreras Guerrero de Stavropoulos et al. | |
| 4,311,138 A | 1/1982 | Sugarman | |
| 4,356,828 A | 11/1982 | Jamshidi | |
| 4,410,020 A | 10/1983 | Lorenz | |
| 4,439,162 A | 3/1984 | Blaine | |
| 4,515,168 A | 5/1985 | Chester et al. | |
| 4,566,438 A | 1/1986 | Liese et al. | |
| 4,836,632 A | 6/1989 | Bardoorian | |
| 4,867,686 A | 9/1989 | Goldstein | |
| 4,880,971 A | 11/1989 | Danisch | |
| 5,065,236 A | 11/1991 | Diner | |
| 5,197,476 A | 3/1993 | Nowacki et al. | |
| 5,198,877 A | 3/1993 | Schulz | |
| 5,241,184 A | 8/1993 | Menzel | |
| 5,249,581 A | 10/1993 | Horbal et al. | |
| 5,295,483 A | 3/1994 | Nowacki et al. | |
| 5,321,257 A | 6/1994 | Danisch | |
| 5,391,081 A | 2/1995 | Lampotang et al. | |
| 5,517,997 A | 5/1996 | Fontenot | |
| 5,518,407 A | 5/1996 | Greenfield et al. | |
| 5,534,704 A | 7/1996 | Robinson et al. | |
| 5,622,170 A | 4/1997 | Shulz | |
| 5,651,783 A | 7/1997 | Reynard | |
| 5,690,618 A * | 11/1997 | Smith ............... A61M 5/31546 604/232 |
| 5,727,948 A | 3/1998 | Jordan | |
| 5,766,016 A | 8/1998 | Sinclair et al. | |
| 5,817,105 A | 10/1998 | Van Der Brug | |
| 5,828,770 A | 10/1998 | Leis et al. | |
| 5,890,908 A | 4/1999 | Lampotang et al. | |
| 5,899,692 A | 5/1999 | Davis et al. | |
| 5,923,417 A | 7/1999 | Leis | |
| 5,954,648 A | 9/1999 | Van Der Brug | |
| 5,954,701 A | 9/1999 | Matalon | |
| 6,024,576 A | 2/2000 | Bevirt et al. | |
| 6,061,644 A | 5/2000 | Leis | |
| 6,064,749 A | 5/2000 | Hirota et al. | |
| 6,127,672 A | 10/2000 | Danisch | |
| 6,172,499 B1 | 1/2001 | Ashe | |
| 6,217,558 B1 | 4/2001 | Zadini et al. | |
| 6,288,785 B1 | 9/2001 | Frantz et al. | |
| 6,353,226 B1 | 3/2002 | Khalil et al. | |
| 6,385,482 B1 | 5/2002 | Boksberger et al. | |
| 6,428,323 B1 | 8/2002 | Pugh | |
| 6,470,302 B1 | 10/2002 | Cunningham et al. | |
| 6,485,308 B1 | 11/2002 | Goldstein | |
| 6,538,634 B1 | 3/2003 | Chui et al. | |
| 6,553,326 B1 | 4/2003 | Kirsch et al. | |
| 6,564,087 B1 | 5/2003 | Pitris et al. | |
| 6,568,941 B1 | 5/2003 | Goldstein | |
| 6,575,757 B1 | 6/2003 | Leight et al. | |
| 6,625,563 B2 | 9/2003 | Kirsch et al. | |
| 6,702,790 B1 | 3/2004 | Ross et al. | |
| 6,769,286 B2 | 8/2004 | Biermann et al. | |
| 6,774,624 B2 | 8/2004 | Anderson et al. | |
| 6,836,745 B2 | 12/2004 | Seiler et al. | |
| 6,857,878 B1 | 2/2005 | Chosack et al. | |
| 6,863,536 B1 | 3/2005 | Fisher et al. | |
| 7,015,859 B2 | 3/2006 | Anderson | |
| 7,115,113 B2 | 10/2006 | Evans et al. | |
| 7,137,712 B2 | 11/2006 | Brunner et al. | |
| 7,158,754 B2 | 1/2007 | Anderson | |
| 7,194,296 B2 | 3/2007 | Frantz et al. | |
| 7,204,796 B1 | 4/2007 | Seiler | |
| 7,247,149 B2 | 7/2007 | Beyerlein | |
| 7,383,728 B2 | 6/2008 | Noble et al. | |
| 7,500,853 B2 | 3/2009 | Bevirt et al. | |
| 7,544,062 B1 | 6/2009 | Hauschild et al. | |
| 7,553,159 B1 | 6/2009 | Arnal et al. | |
| 7,594,815 B2 | 9/2009 | Toly | |
| 7,665,995 B2 | 2/2010 | Toly | |
| 7,725,279 B2 | 5/2010 | Luinge et al. | |
| 7,761,139 B2 | 7/2010 | Tearney et al. | |
| 7,783,441 B2 | 8/2010 | Nieminen et al. | |
| 7,857,626 B2 | 12/2010 | Toly | |
| 7,912,662 B2 | 3/2011 | Zuhars et al. | |
| 7,945,311 B2 | 5/2011 | McCloy et al. | |
| 8,007,281 B2 | 8/2011 | Toly | |
| 8,040,127 B2 | 10/2011 | Jensen | |
| 8,072,606 B2 | 12/2011 | Chau et al. | |
| 8,131,342 B2 | 3/2012 | Anderson | |
| 8,165,844 B2 | 4/2012 | Luinge et al. | |
| 8,203,487 B2 | 6/2012 | Hol et al. | |
| 8,208,716 B2 | 6/2012 | Choi et al. | |
| 8,226,610 B2 | 7/2012 | Edwards et al. | |
| 8,250,921 B2 | 8/2012 | Nasiri et al. | |
| 8,257,250 B2 | 9/2012 | Tenger et al. | |
| 8,277,411 B2 | 10/2012 | Gellman | |
| 8,319,182 B1 | 11/2012 | Brady et al. | |
| 8,342,853 B2 | 1/2013 | Cohen | |
| 8,351,773 B2 | 1/2013 | Nasiri et al. | |
| 8,382,485 B2 | 2/2013 | Bardsley | |
| 8,403,888 B2 | 3/2013 | Gaudet | |
| 8,408,918 B2 | 4/2013 | Hu et al. | |
| 8,409,140 B2 | 4/2013 | Ejlersen et al. | |
| 8,437,833 B2 | 5/2013 | Silverstein | |
| 8,442,619 B2 | 5/2013 | Li et al. | |
| 8,450,997 B2 | 5/2013 | Silverman | |
| 8,467,855 B2 | 6/2013 | Yasui | |
| 8,469,716 B2 | 6/2013 | Fedotov et al. | |
| 8,525,990 B2 | 9/2013 | Wilcken | |
| 8,535,062 B2 | 9/2013 | Nguyen | |
| 8,556,635 B2 | 10/2013 | Toly | |
| 8,632,498 B2 | 1/2014 | Rimsa et al. | |
| 8,647,124 B2 | 2/2014 | Bardsley et al. | |
| 8,655,622 B2 | 2/2014 | Yen et al. | |
| 8,684,744 B2 | 4/2014 | Selz et al. | |
| 8,689,801 B2 | 4/2014 | Ritchey et al. | |
| 8,715,233 B2 | 5/2014 | Brewer et al. | |
| 8,764,449 B2 | 7/2014 | Rios et al. | |
| 8,818,751 B2 | 8/2014 | Van Acht et al. | |
| 8,917,916 B2 | 12/2014 | Martin et al. | |
| 8,924,334 B2 | 12/2014 | Lacey et al. | |
| 8,945,147 B2 | 2/2015 | Ritchey et al. | |
| 8,961,189 B2 | 2/2015 | Rios et al. | |
| 8,994,366 B2 | 3/2015 | Ashe | |
| 9,017,080 B1 | 4/2015 | Placik | |
| 9,024,624 B2 | 5/2015 | Brunner | |
| 9,031,314 B2 | 5/2015 | Clausen et al. | |
| 9,053,641 B2 | 6/2015 | Samosky | |
| 9,123,261 B2 | 9/2015 | Lowe | |
| 9,251,721 B2 | 2/2016 | Lampotang et al. | |
| 9,275,557 B2 | 3/2016 | Trotta | |
| 9,318,032 B2 | 4/2016 | Samosky et al. | |
| 9,361,809 B1 | 6/2016 | Caron | |
| 9,439,653 B2 | 9/2016 | Avneri et al. | |
| 9,443,446 B2 | 9/2016 | Rios et al. | |
| 9,456,766 B2 | 10/2016 | Cox et al. | |
| 9,460,638 B2 | 10/2016 | Baker et al. | |
| 9,486,162 B2 | 11/2016 | Zhuang et al. | |
| 9,554,716 B2 | 1/2017 | Burnside et al. | |
| 9,595,208 B2 | 3/2017 | Ottensmeyer et al. | |
| 9,626,805 B2 | 4/2017 | Lampotang et al. | |
| 9,666,102 B2 | 5/2017 | East et al. | |
| 9,792,836 B2 | 10/2017 | Rios et al. | |
| 9,922,578 B2 | 3/2018 | Foster et al. | |
| 10,083,630 B2 | 9/2018 | Samosky et al. | |
| 10,173,015 B2 | 1/2019 | Fiedler et al. | |
| 10,269,266 B2 | 4/2019 | Rios et al. | |
| 10,290,231 B2 | 5/2019 | Rios et al. | |
| 10,290,232 B2 | 5/2019 | Rios et al. | |
| 10,325,522 B2 | 6/2019 | Samosky et al. | |
| 10,500,340 B2 | 12/2019 | Rios et al. | |

(56) References Cited

U.S. PATENT DOCUMENTS

| | | |
|---|---|---|
| 2002/0076681 A1 | 6/2002 | Leight et al. |
| 2002/0168618 A1 | 11/2002 | Anderson et al. |
| 2002/0191000 A1 | 12/2002 | Henn |
| 2003/0031993 A1 | 2/2003 | Pugh |
| 2003/0055380 A1 | 3/2003 | Flaherty |
| 2003/0108853 A1 | 6/2003 | Chosack et al. |
| 2003/0114842 A1 | 6/2003 | DiStefano |
| 2003/0220557 A1 | 11/2003 | Cleary et al. |
| 2004/0009459 A1 | 1/2004 | Anderson et al. |
| 2004/0092878 A1 | 5/2004 | Flaherty |
| 2004/0118225 A1 | 6/2004 | Wright et al. |
| 2004/0126746 A1 | 7/2004 | Toly |
| 2004/0175684 A1 | 9/2004 | Kaasa et al. |
| 2004/0234933 A1 | 11/2004 | Dawson et al. |
| 2005/0055241 A1 | 3/2005 | Horstmann |
| 2005/0057243 A1 | 3/2005 | Johnson et al. |
| 2005/0070788 A1 | 3/2005 | Wilson et al. |
| 2005/0084833 A1 | 4/2005 | Lacey et al. |
| 2005/0181342 A1 | 8/2005 | Toly |
| 2005/0203380 A1 | 9/2005 | Sauer et al. |
| 2006/0084050 A1 | 4/2006 | Haluck |
| 2006/0194180 A1 | 8/2006 | Bevirt et al. |
| 2006/0264745 A1 | 11/2006 | Da Silva |
| 2006/0264967 A1* | 11/2006 | Ferreyro .......... A61B 17/00234 606/93 |
| 2007/0003917 A1 | 1/2007 | Kitching et al. |
| 2007/0179448 A1 | 8/2007 | Lim et al. |
| 2007/0197954 A1 | 8/2007 | Keenan |
| 2007/0238981 A1 | 10/2007 | Zhu |
| 2008/0038703 A1 | 2/2008 | Segal et al. |
| 2008/0097378 A1 | 4/2008 | Zuckerman |
| 2008/0107305 A1 | 5/2008 | Vanderkooy et al. |
| 2008/0123910 A1 | 5/2008 | Zhu |
| 2008/0138781 A1 | 6/2008 | Pellegrin et al. |
| 2008/0176198 A1 | 7/2008 | Ansari et al. |
| 2008/0177174 A1 | 7/2008 | Crane |
| 2008/0194973 A1 | 8/2008 | Imam |
| 2009/0036902 A1 | 2/2009 | Dimaio et al. |
| 2009/0043253 A1 | 2/2009 | Podaima |
| 2009/0046140 A1 | 2/2009 | Lashmet |
| 2009/0061404 A1 | 3/2009 | Toly |
| 2009/0074262 A1 | 3/2009 | Kudavelly |
| 2009/0081619 A1 | 3/2009 | Miasnik |
| 2009/0081627 A1 | 3/2009 | Ambrozio |
| 2009/0123896 A1 | 5/2009 | Hu et al. |
| 2009/0142741 A1 | 6/2009 | Ault et al. |
| 2009/0161827 A1 | 6/2009 | Gertner et al. |
| 2009/0208915 A1 | 8/2009 | Pugh |
| 2009/0221908 A1 | 9/2009 | Glossop |
| 2009/0263775 A1 | 10/2009 | Ullrich |
| 2009/0265671 A1 | 10/2009 | Sachs et al. |
| 2009/0275810 A1 | 11/2009 | Ayers et al. |
| 2009/0278791 A1 | 11/2009 | Slycke et al. |
| 2009/0305213 A1 | 12/2009 | Burgkart et al. |
| 2009/0326556 A1 | 12/2009 | Diolaiti |
| 2010/0030111 A1 | 2/2010 | Perriere |
| 2010/0071467 A1 | 3/2010 | Nasiri et al. |
| 2010/0099066 A1 | 4/2010 | Mire et al. |
| 2010/0120006 A1 | 5/2010 | Bell |
| 2010/0167249 A1 | 7/2010 | Ryan |
| 2010/0167250 A1 | 7/2010 | Ryan et al. |
| 2010/0167254 A1 | 7/2010 | Nguyen |
| 2010/0179428 A1 | 7/2010 | Pederson et al. |
| 2010/0198141 A1 | 8/2010 | Laitenberger et al. |
| 2010/0273135 A1 | 10/2010 | Cohen |
| 2011/0027767 A1 | 2/2011 | Divinagracia |
| 2011/0046915 A1 | 2/2011 | Hol et al. |
| 2011/0060229 A1 | 3/2011 | Hulvershorn et al. |
| 2011/0071419 A1 | 3/2011 | Liu et al. |
| 2011/0144658 A1 | 6/2011 | Wenderow et al. |
| 2011/0202012 A1 | 8/2011 | Bartlett |
| 2011/0207102 A1 | 8/2011 | Trotta et al. |
| 2011/0236866 A1 | 9/2011 | Psaltis et al. |
| 2011/0257596 A1 | 10/2011 | Gaudet |
| 2011/0269109 A2 | 11/2011 | Miyazaki |
| 2011/0282188 A1 | 11/2011 | Burnside et al. |
| 2011/0294103 A1 | 12/2011 | Segal et al. |
| 2011/0301500 A1 | 12/2011 | Maguire et al. |
| 2011/0306025 A1 | 12/2011 | Sheehan et al. |
| 2012/0002014 A1 | 1/2012 | Walsh |
| 2012/0015336 A1 | 1/2012 | Mach |
| 2012/0026307 A1 | 2/2012 | Price |
| 2012/0034587 A1 | 2/2012 | Toly |
| 2012/0082969 A1 | 4/2012 | Schwartz et al. |
| 2012/0130269 A1 | 5/2012 | Rea |
| 2012/0148994 A1 | 6/2012 | Hori et al. |
| 2012/0171652 A1 | 7/2012 | Sparks et al. |
| 2012/0183238 A1 | 7/2012 | Savvides et al. |
| 2012/0209243 A1* | 8/2012 | Yan ....................... A61M 5/008 604/500 |
| 2012/0214144 A1 | 8/2012 | Trotta et al. |
| 2012/0219937 A1 | 8/2012 | Hughes |
| 2012/0238875 A1 | 9/2012 | Savitsky et al. |
| 2012/0251987 A1 | 10/2012 | Huang et al. |
| 2012/0280988 A1 | 11/2012 | Lampotang et al. |
| 2012/0282583 A1 | 11/2012 | Thaler et al. |
| 2012/0293632 A1 | 11/2012 | Yukich |
| 2012/0301858 A1 | 11/2012 | Park et al. |
| 2012/0323520 A1 | 12/2012 | Keal |
| 2013/0006178 A1 | 1/2013 | Pinho et al. |
| 2013/0018494 A1 | 1/2013 | Amini |
| 2013/0046489 A1 | 2/2013 | Keal |
| 2013/0100256 A1 | 4/2013 | Kirk et al. |
| 2013/0131503 A1 | 5/2013 | Schneider et al. |
| 2013/0179110 A1 | 7/2013 | Lee |
| 2013/0189658 A1 | 7/2013 | Peters et al. |
| 2013/0189663 A1 | 7/2013 | Tuchschmid et al. |
| 2013/0197845 A1 | 8/2013 | Keal |
| 2013/0198625 A1 | 8/2013 | Anderson |
| 2013/0203032 A1 | 8/2013 | Bardsley |
| 2013/0223673 A1 | 8/2013 | Davis et al. |
| 2013/0236872 A1 | 9/2013 | Laurusonis et al. |
| 2013/0267838 A1 | 10/2013 | Fronk et al. |
| 2013/0296691 A1 | 11/2013 | Ashe |
| 2013/0308827 A1 | 11/2013 | Dillavou et al. |
| 2013/0323700 A1 | 12/2013 | Samosky et al. |
| 2013/0342657 A1 | 12/2013 | Robertson |
| 2014/0039452 A1 | 2/2014 | Bangera et al. |
| 2014/0071165 A1 | 3/2014 | Tuchschmid et al. |
| 2014/0102167 A1 | 4/2014 | MacNeil et al. |
| 2014/0120505 A1 | 5/2014 | Rios et al. |
| 2014/0121636 A1 | 5/2014 | Boyden |
| 2014/0129200 A1 | 5/2014 | Bronstein et al. |
| 2014/0162232 A1 | 6/2014 | Yang et al. |
| 2014/0212864 A1 | 7/2014 | Rios et al. |
| 2014/0240314 A1 | 8/2014 | Fukazawa et al. |
| 2014/0244209 A1 | 8/2014 | Lee et al. |
| 2014/0260704 A1 | 9/2014 | Lloyd et al. |
| 2014/0278183 A1 | 9/2014 | Zheng et al. |
| 2014/0278205 A1 | 9/2014 | Bhat et al. |
| 2014/0278215 A1 | 9/2014 | Keal et al. |
| 2014/0322683 A1 | 10/2014 | Baym et al. |
| 2014/0349263 A1 | 11/2014 | Shabat et al. |
| 2014/0349266 A1 | 11/2014 | Choi |
| 2014/0363801 A1 | 12/2014 | Samosky et al. |
| 2015/0031987 A1 | 1/2015 | Pameijer et al. |
| 2015/0079545 A1 | 3/2015 | Kurtz |
| 2015/0086955 A1 | 3/2015 | Poniatowski et al. |
| 2015/0104773 A1 | 4/2015 | Toly et al. |
| 2015/0182706 A1 | 7/2015 | Wurmbauer et al. |
| 2015/0206456 A1 | 7/2015 | Foster et al. |
| 2015/0262512 A1 | 9/2015 | Rios et al. |
| 2015/0348443 A1 | 12/2015 | Rios et al. |
| 2015/0352294 A1 | 12/2015 | O'Mahony et al. |
| 2015/0379899 A1 | 12/2015 | Baker et al. |
| 2015/0379900 A1 | 12/2015 | Samosky et al. |
| 2016/0000411 A1 | 1/2016 | Raju et al. |
| 2016/0001016 A1 | 1/2016 | Poulsen et al. |
| 2016/0155363 A1 | 6/2016 | Rios et al. |
| 2016/0193428 A1 | 7/2016 | Perthu |
| 2016/0213856 A1 | 7/2016 | Despa et al. |
| 2016/0293058 A1 | 10/2016 | Gaillot et al. |
| 2016/0374902 A1 | 12/2016 | Govindasamy et al. |
| 2017/0053563 A1 | 2/2017 | Holloway |

(56) References Cited

U.S. PATENT DOCUMENTS

| | | |
|---|---|---|
| 2017/0136185 A1 | 5/2017 | Rios et al. |
| 2017/0178540 A1 | 6/2017 | Rios et al. |
| 2017/0186339 A1 | 6/2017 | Rios et al. |
| 2017/0245943 A1 | 8/2017 | Foster et al. |
| 2017/0252108 A1 | 9/2017 | Rios et al. |
| 2017/0254636 A1 | 9/2017 | Foster et al. |
| 2017/0316720 A1 | 11/2017 | Singh et al. |
| 2018/0012516 A1 | 1/2018 | Rios et al. |
| 2018/0068075 A1 | 3/2018 | Shiwaku |
| 2018/0197441 A1 | 7/2018 | Rios et al. |
| 2018/0225991 A1 | 8/2018 | Pedroso et al. |
| 2018/0261125 A1 | 9/2018 | Rios et al. |
| 2018/0261126 A1 | 9/2018 | Rios et al. |
| 2018/0271581 A1 | 9/2018 | OuYang et al. |
| 2018/0333543 A1* | 11/2018 | Diaz .................. A61M 5/3221 |
| 2018/0338806 A1 | 11/2018 | Grubbs |
| 2019/0130792 A1 | 5/2019 | Rios et al. |
| 2020/0202747 A1 | 6/2020 | Rios et al. |
| 2020/0206424 A1 | 7/2020 | Rios et al. |
| 2020/0226951 A1 | 7/2020 | Rios et al. |

FOREIGN PATENT DOCUMENTS

| | | |
|---|---|---|
| CA | 2865236 A1 | 9/2013 |
| CN | 2751386 Y | 1/2006 |
| CN | 201213049 Y | 3/2009 |
| CN | 201359805 Y | 12/2009 |
| CN | 201465399 U | 5/2010 |
| CN | 101908294 A | 12/2010 |
| CN | 202159452 U | 3/2012 |
| CN | 102708745 A | 10/2012 |
| CN | 102737533 A | 10/2012 |
| CN | 104703641 A | 6/2015 |
| CN | 105118350 A | 12/2015 |
| CN | 205541594 U | 8/2016 |
| CN | 106710413 A | 5/2017 |
| CN | 107067856 A | 8/2017 |
| DE | 202005021286 U1 | 9/2007 |
| EP | 0316763 A1 | 5/1989 |
| EP | 1504713 A1 | 2/2005 |
| EP | 1723977 A1 | 11/2006 |
| EP | 1884211 A2 | 2/2008 |
| EP | 2425416 B1 | 3/2015 |
| EP | 2538398 B1 | 8/2015 |
| EP | 2756857 B1 | 5/2016 |
| GB | 2288686 B | 7/1997 |
| GB | 2309644 A | 8/1997 |
| GB | 2 309 644 B | 5/2000 |
| GB | 2508510 | 6/2014 |
| IN | 201202900 P1 | 11/2013 |
| JP | H10161522 A | 6/1998 |
| JP | H10260627 A | 9/1998 |
| JP | 2004-348095 A | 12/2004 |
| JP | 2006-189525 A | 7/2006 |
| JP | 2008-83624 A | 4/2008 |
| JP | 2011-113056 A | 6/2011 |
| JP | 2013-037088 A | 2/2013 |
| JP | 52-21420 | 6/2013 |
| JP | 2013-250453 A | 12/2013 |
| JP | 2014-153482 A | 8/2014 |
| KR | 2012009379 A | 2/2012 |
| KR | 20140047943 A | 4/2014 |
| KR | 10-1397522 B1 | 5/2014 |
| TW | 201207785 A | 2/2012 |
| WO | WO 96/16389 | 5/1996 |
| WO | WO 00/53115 | 9/2000 |
| WO | WO 02/083003 | 10/2002 |
| WO | WO 2005/083653 | 9/2005 |
| WO | WO 2007/109540 | 9/2007 |
| WO | WO 2008/005315 A2 | 1/2008 |
| WO | WO 2008/122006 A1 | 10/2008 |
| WO | WO 2009/023247 A1 | 2/2009 |
| WO | WO 2009/049282 | 4/2009 |
| WO | WO 2009/094646 | 7/2009 |
| WO | WO 2009/141769 | 11/2009 |
| WO | WO 2011/043645 | 4/2011 |
| WO | WO 2011/127379 | 10/2011 |
| WO | WO 2011/136778 | 11/2011 |
| WO | WO 2012/075166 | 6/2012 |
| WO | WO 2012/088471 A1 | 6/2012 |
| WO | WO 2012/101286 | 8/2012 |
| WO | WO 2012/106706 | 8/2012 |
| WO | WO 2012/155056 | 11/2012 |
| WO | WO 2013/025639 | 2/2013 |
| WO | WO 2013/064804 | 5/2013 |
| WO | WO 2014/070799 | 5/2014 |
| WO | WO 2014/100658 | 6/2014 |
| WO | WO 2015/109251 | 7/2015 |
| WO | WO 2015/110327 A1 | 7/2015 |
| WO | WO 2015/136564 | 9/2015 |
| WO | WO 2015/138608 | 9/2015 |
| WO | WO 2015/171778 | 11/2015 |
| WO | WO 2016/089706 | 6/2016 |
| WO | WO 2016/123144 A2 | 8/2016 |
| WO | WO 2016/162298 | 10/2016 |
| WO | WO 2016/191127 | 12/2016 |
| WO | WO 2017/048929 A1 | 3/2017 |
| WO | WO 2017/048931 A1 | 3/2017 |
| WO | WO 2017/050781 A1 | 3/2017 |
| WO | WO 2017/060017 A1 | 4/2017 |
| WO | WO 2017/070391 | 4/2017 |
| WO | WO 2017/151441 | 9/2017 |
| WO | WO 2017/151716 | 9/2017 |
| WO | WO 2017/151963 | 9/2017 |
| WO | WO 2017/153077 | 9/2017 |
| WO | WO 2018/136901 | 7/2018 |

OTHER PUBLICATIONS

Correa et al., "Virtual Reality Simulator for Dental Anesthesia Training in the Inferior Alveolar Nerve Block," Journal of Applied Oral Science, vol. 25, No. 4, Jul./Aug. 2017, pp. 357-366.

Jafarzadeh et al., "Design and construction of an automatic syringe injection pump," Pacific Science Review A: Natural Science and Engineering 18, 2016, in 6 pages.

Poyade et al., "Development of a Haptic Training Simulation for the Administration of Dental Anesthesia Based Upon Accurate Anatomical Data," Conference and Exhibition of the European Association of Virtual and Augmented Reality, 2014, in 5 pages.

Quio, "Smartinjector," available at https://web.archive.org/web/20161017192142/http://www.quio.com/smartinjector, Applicant believes to be available as early as Oct. 17, 2016, in 3 pages.

Afzal, et al., "Use of Earth's Magnetic Field for Mitigating Gyroscope Errors Regardless of Magnetic Perturbation," Sensors 2011, 11, 11390-11414; doi:10.3390/s111211390, 25 pp. published Nov. 30, 2011.

Andraos et al., "Sensing your Orientation" Address 2007, 7 pp.

Arms, S.W., "A Vision for Future Wireless Sensing Systems," 44 pp., 2003.

Bao, et al., "A Novel Map-Based Dead-Reckoning Algorithm for Indoor Localization", J. Sens. Actuator Networks, 2014, 3, 44-63; doi:10.3390/jsan3010044, 20 pp., Jan. 3, 2014.

Benbasat et al., "An Inertial Measurement Framework for Gesture Recognition and Applications," I. Wachsmuth and T. Sowa (Eds.): GW 2001, Springer-Verlag Berlin Heidelberg, 12 pp., 2002.

Bergamini et al., "Estimating Orientation Using Magnetic and Inertial Sensors and Different Sensor Fusion Approaches: Accuracy Assessment in Manual and Locomotion Tasks", Oct. 2014, 18625-18649.

Brunet et al., "Uncalibrated Stereo Vision," A CS 766 Project, University of Wisconsin—Madison, 6 pp, Fall 2004, http://pages.cs.wisc.edu/~chaol/cs766/.

Brunet et al., "Uncalibrated Stereo Vision," A CS 766 Project, University of Wisconsin—Madison, 13 pp, Fall 2004, http://pages.cs.wisc.edu/~chaol/cs766/.

Desjardins, et al. "Epidural needle with embedded optical fibers for spectroscopic differentiation of tissue: ex vivo feasibility study", Biomedical Optics Express, vol. 2(6): pp. 1-10. Jun. 2011.

"EPGL Medical Invents Smart Epidural Needle, Nerve Ablation and Trigger Point Treatment Devices: New Smart Medical Devices Will

(56) References Cited

OTHER PUBLICATIONS

Give Physicians Advanced Situational Awareness During Critical Procedures," EPGL Medical, dated Aug. 12, 2013, in 3 pages. Retrieved from http://www.prnewswire.com/news-releases/epgl-medical-invents-smart-epidural-needle-nerve-ablation-and-trigger-point-treatment-devices-219344621.html#.
"The EpiAccess System: Access with Confidence", EpiEP Epicardial Solutions, dated 2015, in 2 pages.
Esteve, Eric, "Why do you need 9D Sensor Fusion to support 3D orientation?", 5 pp., Aug. 23, 2014, https://www.semiwiki.com/forum/content/3794-why-do-you-need-9d-sensor-fusion-support-3d-orientation.html.
Garg et al., "Radial Artery cannulation—Prevention of pain and Techniques of cannulation: review of literature," The Internet Journal of Anesthesiology, vol. 19, No. 1, 2008, in 6 pages.
Grenet et al., "spaceCoder: a Nanometric 3D Position Sensing Device," CSEM Scientific & Technical Report, 1 page, 2011.
Helen, L., et al. "Investigation of tissue bioimpedance using a macro-needle with a potential application in determination of needle-to-nerve proximity", Proceedings of the 8th International Conference on Sensing Technology, Sep. 2-4, 2014, pp. 376-380.
Inition. Virtual Botox: Haptic App Simulated Injecting the Real Thing. Retrieved from http://inition.co.uk/case-study/virtual-botox-haptic-app-simulates-injecting-real-thing.
International Search Report and Written Opinion for Appl. No. PCT/US2013/067352 dated Mar. 31, 2014 in 10 pages.
International Search Report and Written Opinion for Appl. No. PCT/US2015/011845, dated Apr. 29, 2015 in 10 pages.
International Search Report and Written Opinion for Appl. No. PCT/US2015/019974, dated May 21, 2015, 10 pages.
International Search Report and Written Opinion for Appl. No. PCT/US2015/062798, dated Mar. 14, 2016, 12 pages.
Kalvøy, H., et al., "Detection of intraneural needle-placement with multiple frequency bioimpedance monitoring: a novel method", Journal of Clinical Monitoring and Computing, Apr. 2016, 30(2):185-192.
Kettenbach et al., "A robotic needle-positioning and guidance system for CT-guided puncture: Ex vivo results," Minimally Invasive Therapy and Allied Technologies, vol. 23, 2014, in 8 pages.
Ladjal, et al., "Interactive Cell Injection Simulation Based on 3D Biomechanical Tensegrity Model," 2008 IEEE/RSJ International Conference on Intelligent Robots and Systems, in 9 pages.
Lee et al., "An Intravenous Injection Simulator Using Augmented Reality for Veterinary Education and its Evaluation," Proceedings of the 11th ACM SIGGRAPH International Conference on Virtual-Reality Continuum and its Applications in Industry, Dec. 2-4, 2012, in 4 pages.
Madgwick, Sebastian O.H., "An efficient orientation filter for inertial and inertial/magnetic sensor arrays," 32 pp., Apr. 30, 2010.
Microsoft, "Integrating Motion and Orientation Sensors," 85 pp., Jun. 10, 2013.
Miller, Nathan L., Low-Power, Miniature Inertial Navigation System with Embedded GPS and Extended Kalman Filter, MicroStrain, Inc., 12 pp., 2012.
MPU-9150 9-Axis Evaluation Board User Guide, Revision 1.0, 15 pp., May 11, 2011, http//www.invensense.com.
MPU-9150, Register Map and Descriptions, Revision 4.2, 52 pp., Sep. 18, 2013, http//www.invensense.com.
MPU-9150, Product Specification, Revision 4.3, 50 pp., Sep. 18, 2013, http//www.invensese.com.
PST Iris Tracker, Plug and Play, 3D optical motion tracking specifications, 1 p., Dec. 4, 2014, www.pstech.com.
PST Iris Tracker, Instruction Manual, 3D optical motion tracking specifications, 42 pp., Jul. 27, 2012, www.pstech.com.
Search and Examination Report for Appl. No. GB1319193.7 in 6 pages dated Mar. 28, 2014.
Search and Examination Report, dated Feb. 23, 2015, by the UK Intellectual Property Office, in the matter of Application No. GB1414892.8 of TruInject Medical Corporation, 6 pp.
State Electronics, "Sensofoil Membrane Potentiometer," Product Information and Technical Specifications, in 6 pages.
Struik, Pieter, "Ultra Low-Power 9D Fusion Implementation: A Case Study," Synopsis, Inc., 7 pp., Jun. 2014.
Sutherland, et al. "An Augmented Reality Haptic Training Simulator for Spinal Needle Procedures," IEEE, 2011.
Truinject Corp., "Smart Injection Platform," http://truinject.com/technology/, in 3 pages.
Varesano, Fabio, "Prototyping Orientation and Motion Sensing Objects with Open Hardware," Dipartimento di Informatica, Univ. Torino, http://www.di.unito.it/~varesano, Feb. 10, 2013, 4 pp.
Varesano, Fabio, "FreeIMU: An Open Hardware Framework for Orientation and Motion Sensing," Dipartimento di Informatica, Univ. Torino, http://www.di.unito.it/~varesano, Mar. 20, 2013, 10 pp.
"A beginner's guide to accelerometers," Dimension Engineering LLC, accessed Jul. 11, 2018, in 2 pages, https://www.dimensionengineering.com/info/accelerometers.
"Accelerometer: Introduction to Acceleration Measurement," Omega Engineering, Sep. 17, 2015, 3 pages, https://www.omega.com/prodinfo/accelerometers.html.
"About the Journal", *J. Dental Educ., Am. Dental Educ. Ass'n*, 2019, http://www.jdentaled.org/content/about-us (last visited Oct. 9, 2019).
Begg et al., "Computational Intelligence for Movement Sciences: Neural Networks and Other Emerging Techniques", *Idea Group Inc (IGI)*, 2006.
Comsa et al, "Bioluminescene imaging of point sources implants in small animals post mortem: evaluation of a method for estimating source strength and depth", *Phys. Med. Biol.*, Aug. 2007, vol. 52, No. 17, pp. 5415-5428.
Hotraphinyo et al., "Precision measurement for microsurgical instrument evaluation", *Conference Proceedings of the 23rd Annual International Conference of the IEEE Engineering in Medicine and Biology Societyl*, 2001, vol. 4, pp. 3454-3457.
Krupa et al., "Autonomous 3-D positioning of surgical instruments in robotized laparoscopic surgery using visual servoing", *IEEE Trans. Robotics and Automation*, 2003, vol. 19, pp. 842-853.
Lee et al., "Augmented reality intravenous injection simulator based 3D medical imaging for veterinary medicine," The Veterinary Journal, 2013, vol. 196, No. 2, pp. 197-202.
Liu et al. "Robust Real-Time Localization of Surgical Instruments in the Eye Surgery Stimulator (EyeSi)", *Signal and Image Processing*, 2002.
Merril et al., "The Ophthalmic Retrobulbar Injection Simulator (ORIS): An Application of Virtual Reality to Medical Education", *Proc. Ann. Symp. Comput. Med. Care*, 1992, pp. 702-706.
Mukherjee et al., "A Hall Effect Sensor Based Syringe Injection Rate Detector", *IEEE 2012 Sixth Int'l Conf. on Sensing Technol. (ICST)*, Dec. 18-21, 2012.
Patterson et al., "Absorption spectroscopy in tissue-simulating materials: a theoretical and experimental study of photon paths", Appl. Optics, Jan. 1995, vol. 34, No. 1, pp. 22-30.
Van Sickle et al., "Construct validation of the ProMIS simulator using novel laparoscopic suturing task", *Surg Endosc*, Sep. 2005, vol. 19, No. 9, pp. 1227-1231.
Wierinck et al., "Expert Performance on a Virtual Reality Simulation System", *71 J. Dental Educ.*, Jun. 2007, pp. 759-766.
Wik et al., "Intubation with laryngoscope versus transillumination performed by paramedic students on mainkins and cadavers", *Resuscitation*, Jan. 1997, vol. 33, No. 3, pp. 215-218.
3D Systems, "ANGIO Mentor Clinical Validations, the Role of Simulation in Boosting the learning Curve in EVAR Procedures," Journal of Surgical Education, Mar.-Apr. 2018, 75(2), pp. 1-2, accessed on Feb. 6, 2020, https://simbionix.com/ simulators/clinical-validations/angio-mentor-clinical-validations/ (listing clinical validations completed on ANGIO Mentor from 2007 through 2018).
3D Systems, "ANGIO Mentor™," Product Brochure/Overview. 2015, 6 pp.
Ainsworth et al., "Simulation Model for Transcervical Laryngeal Injection Providing Real-time Feedback," Annals of Otology, Rhinology & Laryngology, 2014, col. 123 (12), pp. 881-886.

(56) References Cited

OTHER PUBLICATIONS

Banivaheb, Niloofar, "Comparing Measured and Theoretical Target Registration Error of an Optical Tracking System," Feb. 2015, Toronto, Ontario, 128 pp.
Blue Telescope, DAISEY Injector Simulator, Available at https://www.bluetelescope.com/work/ipsen-injection-simulator. Blue Telescope Laboratories 2020. Site visited Aug. 26, 2020.
Blum et al., "A Review of Computer-Based Simulators for Ultrasound Training," Society for Simulation in Healthcare, Apr. 2013, vol. 8, pp. 98-108.
Botden et al., "Suturing training in Augmented Reality: gaining proficiency in suturing skills faster," Surg Endosc, 2009, vol. 23, pp. 2131-2137.
Botden et al., "Augmented versus Virtual Reality Laparoscopic Simulation: What Is the Difference?," World J. Surgery, 31, 2007, 10 pp.
Botden et al., "Face validity study of the ProMIS Augmented Reality laparoscopic suturing simulator," Surgical Technology International, Feb. 2008, 17, 16 pp.
Botden et al., "What is going on in augmented reality simulation in laparoscopic surgery," Surgical Endoscopy 23, 2009, 1693-1700.
Bova et al., "Mixed-Reality Simulation for Neurosurgical Procedures," Neurosurgery, Oct. 2013, vol. 73, No. 4, pp. S138-S145.
Brennan et al., "Classification of diffuse light emission profiles for distinguishing skin layer penetration of a needle-free jet injection," Biomedical Optics Express, Oct. 1, 2019, vol. 10, No. 10, pp. 5081-5092.
Brennan et al., "Light source depth estimation in porcine skin using spatially resolved diffuse imaging," *2016 38th Annual International Conference of the IEEE Engineering in Medicine and Biology Society* (EMBC), Orlando, FL, 2016, pp. 5917-5920.
Brett, et al., "Simulation of resistance forces acting on surgical needles," Proceedings of the Institutional of Mechanical Engineers Part H Journal of Engineering in Medicine, Feb. 1997, vol. 211 Part H, pp. 335-347.
Buchanan, Judith Ann, "Use of Simulation Technology in Dental Education," Journal of Dental Education, 2001, vol. 65, No. 11, 1225-1231.
CAE Healthcare, "CAE ProMIS Laparoscopic Simulator," Product Brochure/Overview, 2012, 2 pp.
Capsulorhexis forceps only technique rehearsed on EYESi before OR (Feb. 10, 2010), https://www.youtube.com/watch?v=ySMl1Vq6Ajw.
Chui et al., "Haptics in computer-mediated simulation: Training in vertebroplasty," Simulation & Gaming, Dec. 2006, vol. 37, No. 4, pp. 438-451.
Coquoz et al., "Determination of depth of in vivo bioluminescent signals using spectral imaging techniques," Conference Proceedings of SPIE, 2003, vol. 4967, pp. 37-45, San Jose, CA.
Craig, Alan B., "Augmented Reality Hardware," Understanding Augmented Reality Chapter 3, 2013, Elsevier Inc., pp. 69-124.
Cumin et al., "Simulators for use in anaesthesia," Anaesthesia, 2007, vol. 62, pp. 151-162.
Datta et al., "The use of electromagnetic motion tracking analysis to objectively measure open surgical skill in the laboratory-based model". vol. 193, No. 5, Nov. 2001, pp. 479-485.
Davenar123, DentSim (Mar. 18, 2008), https://www.youtube.com/watch?v=qkzXUHay1W0.
DentSim Educators, DentSim Classroom Introduction (Aug. 8, 2013), https://vimeo.com/79938695.
DentSimLab, Aha Moments—Dentsim Students explain how their dental skills are improving (Nov. 13, 2013), https://www.youtube.com/watch?v=02NgPmhg55Q.
Dine et al., "Improving cardiopulmonary resuscitation quality and resuscitation training by combining audiovisual feedback and debriefing," Crit Care Med, 2008 vol. 36, No. 10, pp. 2817-2822.
EPED Taiwan, EPED—Computerized Dental Simulator (CDS-100) (Jun. 9, 2014), https://www.youtube.com/watch?v=m8UXaV2ZSXQ.
Ford et al.,"Impact of simulation-based learning on mediation error rates in critically ill patients," Intensive Care Med, 2010, vol. 36, pp. 1526-1531.
Franz et al., "Electromagnetic Tracking in Medicine—A Review of Technology, Validation, and Applications," IEEE, Transactions on Medical Imaging, Aug. 2014, vol. 33, No. 8, pp. 1702-1725.
Garrett et al., "High-Fidelity Patient Simulation: Considerations for Effective Learning," Teaching with Technology: High-Fidelity Simulation, 2010, vol. 31, No. 5, pp. 309-313.
Gottlieb et al., "Faculty Impressions of Dental Students' Performance With and Without Virtual Reality Simulation," Journal of Dental Education, 2011, vol. 75, No. 11, pp. 1443-1451.
Gottlieb et al., "Simulation in Dentistry and Oral Health," The Comprehensive Textbook of Healthcare Simulation Chapter 21, Apr. 2013, pp. 329-340.
Hoffman et al., "Arytenoid Repositioning Device," Annals of Otology, Rhinology & Laryngology, 2014, vol. 123 (3); pp. 195-205.
Hoffman et al., "Transillumination for Needle Localization in the Larynx," The Laryngoscope, 2015, vol. 125, pp. 2341-2348.
Huang et al., "CatAR: A Novel Stereoscopic Augmented Reality Cataract Surgery Training System with Dexterous Instrument Tracking Technology," CHI' 18: Proceedings of the 2018 CHI Conference on Human Factors in Computing Systems, Apr. 21-26, 2018, pp. 1-12, ACM, Montréal, Canada.
IDA Design Awards—Winners, DAISEY Injection Simulator, available at https://idesignawards.com/winners/zoom.php?eid=9-11737-16&count=0&mode=, Available as early as Sep. 7, 2016.
Image Navigation, DentSim by Image Navigation—Augmented Reality Dental Simulation, Nov. 2014, 5 pp., available at https://image-navigation.com/wp-content/uploads/2014/11/DentSim-V5-2-Pager.pdf.
Image Navigation, DentSim Computerized Dental Training Simulator, Product Brochure, Jul. 2014, available at https://image-navigation.com/wp-content/uploads/2014/07/DentsimBrochure.pdf.
Invensense, Inc., "MPU-9150 EV Board User Guide," May 11, 2011, pp. 1-15.
Invensense, Inc., "MPU-9150 Product Specification Revision 4.3," Sep. 18, 2013, pp. 1-50.
Invensense, Inc., "MPU-9150 Register Map and Descriptions Revision 4.2," Sep. 18, 2013, pp. 1-52.
Jasinevicius et al., "An Evaluation of Two Dental Simulation Systems: Virtual Reality versus Contemporary Non-Computer-Assisted," Journal of Dental Education, 2004, vol. 68, No. 11, 1151-1162.
Kandani et al., "Development in blood vessel searching system for HMS," SPIE, Infrared Systems and Photoelectronic Technology III, 2008, vol. 7065, pp. 1-10.
Khosravi, Sara, "Camera-Based Estimation of Needle Pose for Ultrasound Percutaneous Procedures," University of British Columbia, 2008, pp. ii-83.
Kumar et al., "Virtual Instrumentation System With Real-Time Visual Feedback and Needle Position Warning Suitable for Ophthalmic Anesthesia Training," IEEE: Transactions on Instrumentation and Measurement, May 2018, vol. 67, No. 5, pp. 1111-1123.
Lacey et al., "Mixed-Reality Simulation of Minimally Invasive Surgeries," IEEE Computer Society, 2007, pp. 76-87.
Laerdal, "Virtual Phlebotomy—Directions for Use," Self-directed Phlebotomy learning, Aug. 4, 2010, pp. 1-100.
Laerdal Medical, http://www.laerdal.com/us/nav/203/Venous-Arterial-Access, printed Mar. 8, 2019 in 3 pgs.
Lampotang et al., "A Subset of Mixed Simulations: Augmented Physical Simulations with Virtual Underlays," Interservice/Industry Training, Simulation, and Education Conference (I/ITSEC), 2012, pp. 1-11.
Lampotang et al., "Mixed Reality Simulation for Training Reservists and Military Medical Personnel in Subclavian Central Venous Access," Informational Poster, Ufhealth, Center for Safety, Simulation and Advanced Learning Technologies, 2015, 1 pp. available at https://simulation.health.ufl.edu/files/2018/12/Dept_CoR_2015-Mixed_Reality_Simulation_for_Training.pdf.

(56) References Cited

OTHER PUBLICATIONS

Lee et al., "A Phantom Study on the Propagation of NIR Rays under the Skin for Designing a Novel Vein-Visualizing Device," ICCAS, Oct. 20-23, 2013, pp. 821-823.
Lee et al., "The utility of endovascular simulation to improve technical performance and stimulate continued interest of preclinical medical students in vascular surgery," Journal of Surgical Education, 2009 APDS Spring Meeting, vol. 66, No. 6, 367-373.
Lee et al., "Virtual Reality Ophthalmic Surgical Simulation as a Feasible Training and Assessment Tool: Results of a Multicentre Study," Canada Journal of Ophthalmology, Feb. 2011 vol. 46, No. 1, 56-60.
Lemole et al., "Virtual Reality in Neurosurgical Education: Part-Task Ventriculostomy Simulation with Dynamic Visual and Haptic Feedback," Neurosurgery, Jul. 2007, vol. 61, No. 1, pp. 142-149.
Leopaldi et al., "The dynamic cardiac biosimulator: A method for training physicians in beating-heart mitral valve repair procedures," The Journal of Thoracic and Cardiovascular Surgery, 2018, vol. 155, No. 1, pp. 147-155.
Lim, M.W. et al., "Use of three-dimensional animation for regional anaesthesia teaching: application to interscalene brachial plexus blockade," British Journal of Anaesthesia, Advance Access, 2004, vol. 94, pp. 372-377.
Liu et al. "Study on an Experimental AC Electromagnetic Tracking System" Proceedings of the 5th World Congress on Intelligent Control and Automation, Jun. 15-19, 2001. pp. 3692-3695.
Medgadget Editors, "EYESI Surgical Simulator," Medgadget, Aug. 28, 2006,4 pp., printed on Feb. 7, 2020, https://www.medgadget.com/2006/08/eyes_i_surgical.html.
Merlone1, Eyesi_Cataract_2011 (Sep. 9, 2011), https://www.youtube.com/watch?v=XTulabWmEvk.
Mnemonic, Ipsen Injection Simulators, available at http://mnemonic.studio/project/ispen-injection-simulators. Copyright 2019, Website viewed on Aug. 24, 2020.
Mnemonic, Injection Simulator (Oct. 20, 2017), https://vimeo.com/239061418.
Mukherjee et al., "An Ophthalmic Anesthesia Training System Using Integrated Capacitive and Hall Effect Sensors," IEEE, Transactions on Instrumentation and Measurement, Jan. 2014, vol. 63, No. 5 , 11 pp.
Nelson, Douglas A. Jr., "A Modular and Extensible Architecture Integrating Sensors, Dynamic Displays of Anatomy and Physiology, and Automated Instruction for Innovations in Clinical Education" Doctoral Dissertation, Univ. of Pitt., 2017, 260 pp.
Nelson et al., "The Tool Positioning Tutor: A Target-Pose Tracking and Display System for Learning Correct Placement of a Medical Device," *Medicine Meets Virtual Reality* 18, IOS Press, 2011, 5 pp.
Ottensmeyer et al., "Ocular and Craniofacial Trauma Treatment Training System: Overview & Eyelid Laceration Module," workshop Proceedings of the 8th International Conference on Intelligent Environments, IOS Press, 2012, 13 pp.
Ozturk et al., "Complications Following Injection of Soft-Tissue Fillers," Aesthetic Surgery Journal, from the American Society for Aesthetic Plastic Surgery, Inc. Reprints and permissions, http://www.sagepub.com/journalsPermissions.nav, 2013, pp. 862-877.
Pitt Innovates, BodyExplorer™ (Sep. 24, 2014), https://www.youtube.com/watch?v=T6G2OWJm5hs.
Pitt Innovates, Pitt Student Innovator Award, Pitt Intellectual Property 2017, Douglas A Nelson Jr. (Nov. 28, 2017), https://www.youtube.com/watch?v=0_CVBgWtCLo.
Rahman et al., "Tracking Manikin Tracheal Intubation Using Motion Analysis," Pediatric Emergency Care, Aug. 2011, vol. 27, No. 8, pp. 701-705.
Robinson et al., "A Mixed-Reality Part-Task Trainer for Subclavian Venous Access," Journal of the Society for Simulation in Healthcare, Feb. 2014, vol. 9, No. 1, pp. 56-64.
Salem et al., "Clinical Skills Laboratories "CSLs" Manual 1432-2011," Jan. 2011, pp. 0-88.
Samosky et al., "BodyWindows: Enhancing a Mannequin with Projective Augmented Reality for Exploring Anatomy, Physiology and Medical Procedures," Medicine Meets Virtual Reality 19, 2012, 433, J.D. Westwood et al. eds., IOS Press, pp. 433-439.
Samosky et al., "Enhancing Medical Device Training with Hybrid Physical—Virtual Simulators: Smart Peripherals for Virtual Devices," Medicine Meets Virtual Reality 20, Jan. 2013, J.D. Westwood et al. eds., IOS Press 377, pp. 377-379.
Samosky, Joseph, "View from the Top: Simulation Director Envisions Greater Use for Training Tool," Biomedical Instrumentation & Technology, 2012, pp. 283-288.
Samosky et al., "Toward a Comprehensive Hybrid Physical—Virtual Reality Simulator of Peripheral Anesthesia with Ultrasound and Neurostimulator Guidance," Medicine Virtual Reality 18, IOS Press, 2011, pp. 552-554.
Satava, "Accomplishments and Challenges of Surgical Simulation", Dawning of the next-generation surgical education, Surgical Endoscopy Ultrasound and Interventional Techniques, Online publication, Feb. 6, 2001, in 10 pages.
Schneider, Chad Michael, "Systems for Robotic Needle Insertion and Tool-Tissue Interaction Modeling," Research Gate, 2004, pp. 1-74, Baltimore, Maryland.
Simbionix, Valencia College's CVT program uses Simbionix ANGIO Mentor simulators, Feb. 26, 2013, https://www.youtube.com/watch?v=oAE0fWzXMjw.
SimEx, "Dental Augmented Reality Simulator," EPED, 3 pp. https://www.epedmed.com/simex. Available as early as 2019.
Spiteri et al., "Phacoemulsification Skills Training and Assessment," The British Journal of Ophthalmology 2010, Aug. 2009, 20 pp.
Stunt et al., "Validation of ArthroS virtual reality simulator for arthroscopic skills," Knee Surgery Sports Traum. Arthroscopy 23, Jun. 11, 2014, 8 pp.
Sultan et al., "A Novel Phantom for Teaching and Learning Ultrasound-guided Needle Manipulation," Journal of Medical Ultrasound, Elsevier Taiwan LLC, Jul. 2013, vol. 21, pp. 152-155.
Suzuki et al., "Simulation of Endovascular Neurointervention Using Silicone Models: Imaging and Manipulation," Neurol Med Chir (Tokyo), 2005, vol. 45, pp. 567-573.
The Simulation Group, Internet Archive Wayback webpage capture of http://www.medicalsim.org/virgil.htm, apparently available Apr. 10, 2013, site visited Aug. 25, 2020.
The Simulation Group, Virgil™ Videos (2002), http://www.medicalsim.org/virgil_vid.htm; http://www.medicalsim.org/virgil/virgil%20expert.mpg.
Ting et al., "A New Technique to Assist Epidural Needle Placement: Fiberoptic-guided Insertion Using Two Wavelengths," Anesthesiology, 2010, vol. 112, pp. 1128-1135.
Touch of Life Technologies, "ToLTech Cystoscopy Simulator Helps Practice Botox Injections," https://www.medgadget.com/2012/05/toltech-cystoscopy-simulator-helps-practice-botox-injections.html, May 2012, printed on Feb. 6, 2020 in 2 pgs.
Touch of Life Technologies, "Touch of Life Technologies' new cystoscopy and bladder injection simulator offers urologists training on use of Botox®," https://www.urotoday.com/recent-abstracts/pelvic-health-reconstruction/urinary-incontinence/50289-touch-of-life-technologies-new-cystoscopy-and-bladder-injection-simulator-offers-urologists-training-on-use-of-botox-onabotulinumtoxina-as-treatment-for-urinary-incontinence-in-adults-with-neurological-conditions.html, May 2012, printed on Feb. 6, 2020 in 2 pgs.
Ufcssalt, "Video of mixed simulation for placement of CVL needle"—(Patent Pending), Dec. 5, 2011, https://www.youtube.com/watch?v=0ITIFbiiwRs.
UFHealth, "UF developing mixed-reality simulators for training in treatment of injured soldiers," Aug. 20, 2014, https://www.youtube.com/watch?v=sMxH1Iprc10& feature=emb_title.
Ungi et al., "Perk Tutor: An Open-Source Training Platform for Ultrasound-Guided Needle Insertions," IEEE Transactions on Biomedical Engineering, Dec. 2012, vol. 59, No. 12, pp. 3475-3481.
Univervisty of Pittsburgh Innovation Institute, "BodyExplorer: An Automated Augmented Reality Simulator for Medical Training and Competency Assessment," Mar. 2016, 2 pp.
Univervisty of Pittsburgh Innovation Institute, "BodyExplorer: Enhancing a Mannequin Medical Simulator with Sensing. Tangible Inter-

(56) References Cited

OTHER PUBLICATIONS action and Projective Augmented Reality for Exploring Dynamic Anatomy, Physiology and Clinical Procedures," 2012, pp. 1-3.
Vaughan et al., "A review of virtual reality based training simulators for orthopedic surgery," Journal Engineering and Physics, 2016, vol. 38, Elsevier Ltd., pp. 59-71.
Virgil™, The Simulation Group/Cimit, "Medical Simulation Chest Trauma Training System," 2002, 6 pp. http://www.medicalsim.org/virgil.htm.
VirtaMed ArthroS™, "Virtual reality arthroscopy for knee, shoulder, hip, ankle & Fast basic skills," Fact Sheet/Brochure Jul. 13, 2011.
VirtaMed ArthroS™ Module Descriptions. 2019.
VirtaMed, ArthroS—The 2012 Arthroscopic Simulator for Knee Arthroscopy, Feb. 1, 2012, https://www.youtube.com/watch?v=Y6w3AGfAqKA.
VirtaMed, Arthroscopy Training Simulator ArthroS Now With Shoulder Module!, Mar. 13, 2013, https://www.youtube.com/watch?v=kPuAm0MIYg0.
VirtaMed, Arthroscopy Training 2013: VirtaMed ArthroS Shoulder Simulator, Sep. 24, 2013, https://www.youtube.com/watch?v=WdCtPYr0wK0.
Virtamed News, "VirtaMed ArthroS—Virtual reality training for knee arthroscopy," VirtaMed, Jul. 13, 2011, 2 pp. accessed on Feb. 6, 2020, https://www.virtamed.com/en/news/virtamed-arthros-virtual-reality-training-knee-arthroscopy/.
VirtaMed, VirtaMed ArthroS™—diagnostic and therapeutic arthroscopy in both the knee and shoulder (Apr. 15, 2014), https://www.youtube.com/watch?v=gtkISWnOzRc.
VRmagic, "eyesi by VRmagic Surgical Simulator," Product Brochure, 2015, available at https://pdf.medicalexpo.com/pdf/vrmagic/eyesi-surgical-product-brochure/112458-159450.html.
Walsh et al., "Use of Simulated Learning Environments in Dentistry and Oral Health Curricula," SLE in Dentistry and Oral Health: Final Report, 2010, Health Workforce Australia, pp. 1-112.
Welk et al., "DentSim—A Future Teaching Option for Dentists," 7 International Journal of Computerized Dentistry, 2004, 9 pp.
Wiles, Andrew et al., "Accuracy assessment and interpretation for optical tracking systems," SPIE, Medical Imaging: Visualization, Image-Guided Procedures and Display, 2004, vol. 5367, pp. 1-12.
Yeo et al., "The Effect of Augmented Reality Training on Percutaneous Needle Placement in Spinal Facet Joint Injections," IEEE, Transactions on Biomedical Engineering, Jul. 2011, vol. 58, No. 7, 8 pp.
Yu et al., "Development of an in Vitro Tracking System with Poly (vinyl alcohol) Hydrogel for Catheter Motion," Journal of Biomedical Science and Engineering, 2010, vol. 5, No. 1, 11-17.
Zoughi "Editor-in-Chief's year-end message"., IEEE Transactions on Instrumentation and Measurement, vol. 59, No. 12, Dec. 2010, pp. 3066-3068.

* cited by examiner

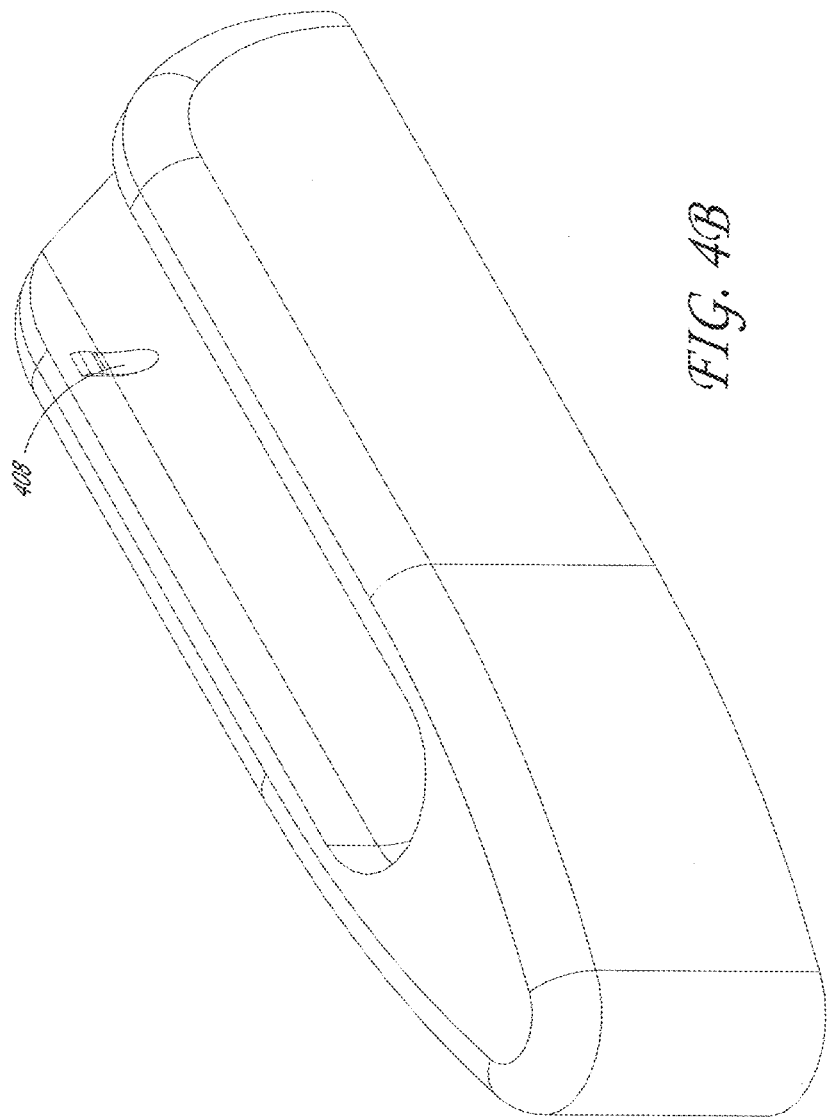

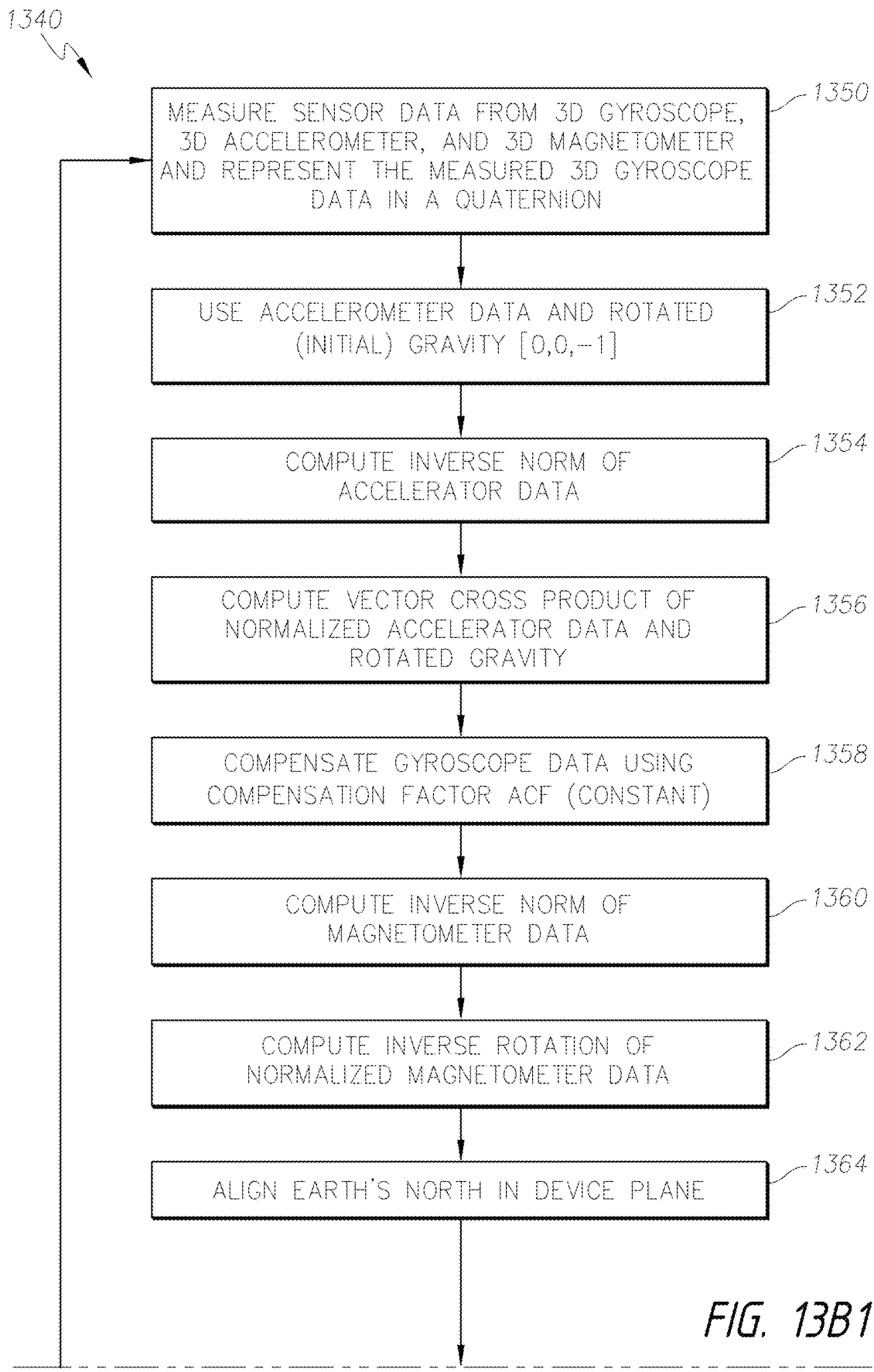
FIG. 13B1

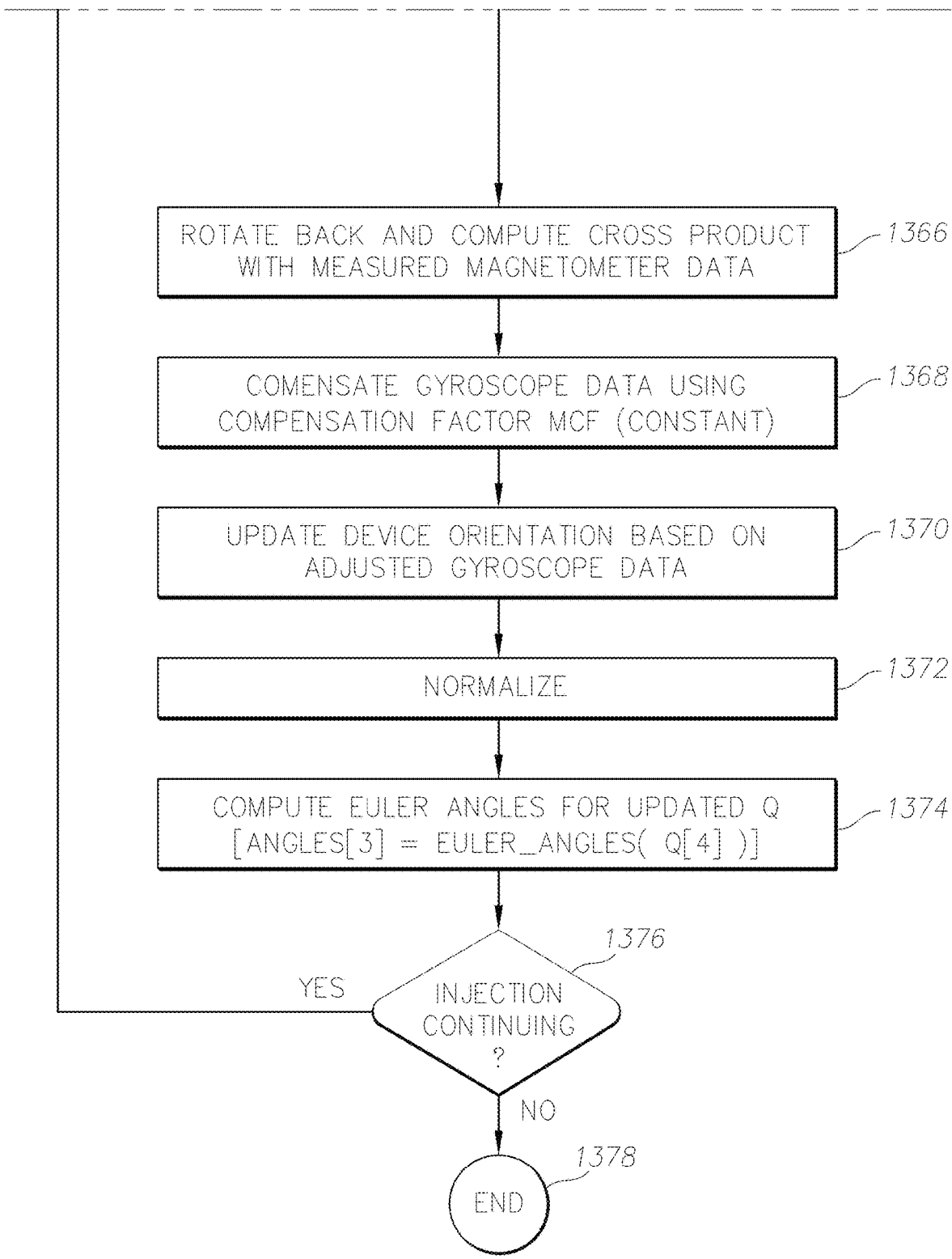
FIG. 13B2

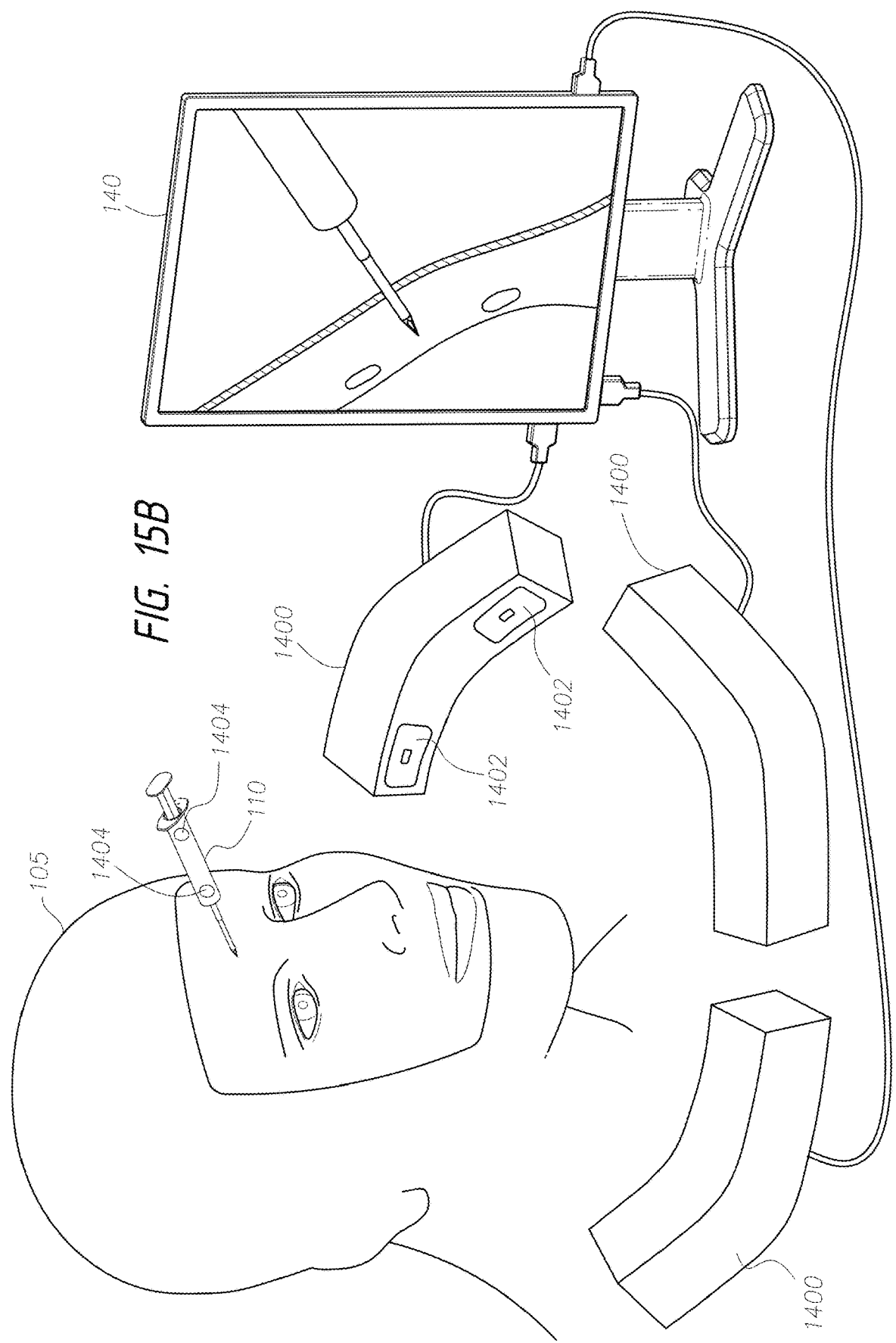

INJECTION SITE TRAINING SYSTEM

This application is a continuation of U.S. patent application Ser. No. 14/598,614, filed Jan. 16, 2015, which claims the benefit of U.S. Provisional Application No. 61/928,915, filed on Jan. 17, 2014, U.S. Provisional Application No. 61/939,093, filed on Feb. 12, 2014, and U.S. Provisional Application No. 62/066,792, filed on Oct. 21, 2014, the entirety of which are hereby incorporated herein by reference.

Any and all applications for which a foreign or domestic priority claim is identified in the Application Data Sheet as filed with the present application are hereby incorporated by reference under 37 CFR 1.57.

BACKGROUND

A variety of medical injection procedures are often performed in prophylactic, curative, therapeutic, or cosmetic treatments. Injections may be administered in various locations on the body, such as under the conjunctiva, into arteries, bone marrow, the spine, the sternum, the pleural space of the chest region, the peritoneal cavity, joint spaces, and internal organs. Injections can also be helpful in administering medication directly into anatomic locations that are generating pain. These injections may be administered intravenously (through the vein), intramuscularly (into the muscle), intradermally (beneath the skin), subcutaneously (into the fatty layer of skin), or intraperitoneally (into the body cavity). Injections can be performed on humans as well as on animals. The methods of administering injections typically vary for different procedures and may depend on the substance being injected, needle size, or area of injection.

Injections are not limited to treating medical conditions, but may be expanded to treating aesthetic imperfections or restorative cosmetic procedures. Many of these procedures are performed through injections of various products into different parts of the body. The aesthetics and therapeutic industry comprises two main categories of injectable products: neuromodulators and dermal fillers. The neuromodulator industry commonly uses nerve-inhibiting products such as Botox®, Dysport®, and Xeomin®. The dermal filler industry uses products administered by providers to patients for both cosmetic and therapeutic reasons, such as, for example, Juvederm®, Restylane®, Belotero®, Sculptra®, Artefill®, and others. These providers or injectors may include plastic surgeons, facial plastic surgeons, oculoplastic surgeons, dermatologists, nurse practitioners, dentists and nurses.

A problem in the administration of injections is that there is no official certification or training process. Anyone with a minimal medically-related license may inject a patient. These "injectors" may include primary care physicians, dentists, veterinarians, nurse practitioners, nurses, physician's assistants, or aesthetic spa physicians. However, the qualifications and training requirements for injectors vary by country, state, and county. For example, in most states in the United States, the only requirement to be permitted to inject patients with neuromodulators and/or fillers is to have a nursing degree or medical degree. Accordingly, there is a lack of uniformity and expertise in administering such injections. The drawbacks with this lack of uniformity in training and expertise are widespread throughout the medical industry. Doctors and practitioners often are not well-trained in administering injections of diagnostic, therapeutic, and cosmetic chemical substances. This lack of training has led to instances of chronic pain, headaches, bruising, swelling, or bleeding in patients.

Current injection training options are classroom-based, with hands-on training performed on live models. The availability of models is limited. Moreover, even when available, live models are limited in the number and types of injections they may receive. The need for live models is restrictive because injectors are unable to be exposed to a wide and diverse range of situations and anatomies in which to practice. For example, it may be difficult to find live models with different skin tones or densities. This makes the training process less effective because patients have diverse anatomical features as well as varying prophylactic, curative, therapeutic, or cosmetic needs. Live models are also restrictive because injectors are unable to practice injection methods on the internal organs of a live model due to safety and health considerations.

As a result of these limited training scenarios, individuals seeking treatments involving injections have a much higher risk of being treated by an inexperienced injector. This may result in low patient satisfaction with the results, or in failed procedures. In many instances, patients have experienced lumpiness from incorrect dermal filler injections. Some failed procedures may result in irreversible problems and permanent damage to a patient's body. For example, patients have experienced vision loss, direct injury to the globe of the eye, and brain infarctions where injectors have incorrectly performed dermal filler procedures. Additional examples of side effects include inflammatory granuloma, skin necrosis, endophthalmitis, injectable-related vascular compromise, cellulitis, biofilm formation, subcutaneous nodules, fibrotic nodules, and other infections.

As a result of the varying qualifications and training requirements for injectors, there is currently no standard to train, educate, and certify providers on the proper and accurate process of various injection techniques. Patients seeking injections also have few resources for determining the qualifications or experience of a care practitioner.

SUMMARY

The present disclosure generally relates to an injection apparatus and training system for prophylactic, curative, therapeutic, acupuncture, or cosmetic injection training and certification. The training system eliminates the need to find live models for hands-on training sessions. The training system provides feedback on trainees and the accuracy of injection procedures performed. In an embodiment, feedback is provided in real time. The training system can be used as a measurement on how the "trainee" is doing prior to receiving actual product by the manufacturing company as a measure of qualification. The training system reduces the risks associated with inexperienced and uncertified medical personnel performing injection procedures.

The training system can be used to educate, train, and certify medical personnel for injection procedures. It can also be utilized as a testing program for certifying medical personnel. The system will enable users to practice a variety of injections, ranging from on label to off label product injections. In some embodiments, the system may allow users to train for therapeutic treatments. In other embodiments, the system may allow users to train for injections into arteries, bone marrow, the spine, the sternum, the pleural space of the chest region, the peritoneal cavity, joint spaces, internal organs, or any other injection sites. The system may be used for any type of injection, including, but not limited to those involving prophylactic, curative, therapeutic, or cosmetic treatments in both humans and animals. Illustratively, by way of non-limiting example, the disclosed system may be used to simulate a cosmetic application of filling of a wrinkle with a dermal filler. In other applications, the systems disclosed herein can be used for dental application and training for dental procedures.

In an aspect of the present disclosure, an injection training system is described that includes a testing tool having a needle and a position sensor, where the position sensor is configured to obtain position information of the testing tool. The system also includes an injection apparatus configured to receive a simulated injection by the testing tool. The system includes a display device configured to receive the position information and to display position data reflective of the position information, wherein the display device includes a processor and a memory device.

In an embodiment of the disclosed injection training system, a method of tracking the position of a testing tool used in an injection training system is described. The method includes obtaining position information of the testing tool from one or more sensors; determining an estimate of the position of the testing tool; transmitting, to a display device, data reflective of the estimate of the position of the testing tool; and displaying, on the display device, the data reflective of the estimate of the position of the testing tool.

In an embodiment, an injection training system is disclosed. The injection training system includes a testing tool having a needle, a plunger, and a marker configured to reflect electromagnetic waves. The system also includes an injection apparatus configured to receive a simulated injection by the testing tool. The injection apparatus also has a marker configured to reflect electromagnetic waves. The system includes an optical tracking system having a field of view, where the optical tracking system is positioned such that the injection apparatus is in the field of view. The optical tracking system is configured to obtain position information of the testing tool and the injection apparatus and to transmit the position information to a display device. The display device is configured to receive the position information and to display position data reflective of the position information.

In one embodiment, there are three main components of the training system: (1) a training apparatus (also referred to interchangeably as an injection apparatus throughout the present disclosure) which features an anatomically accurate model of a human or human body part necessary for injection training, (2) a light detection device, such as, for example, a camera, associated with the training apparatus, and (3) a testing tool with light emitting capabilities. In an embodiment, a fourth component of the training system can include an output device that can run an application which receives communications from the training apparatus or light detection device and generates information regarding injection parameters based on the communications from the injection apparatus or light detection device. In an embodiment, the images captured by the camera are processed by a processor included either in the injection apparatus or in the light detection device before being communicated to the output device. This processing can include, for example, determining an indication of one or more injection parameters. In an embodiment, the anatomical model can include various injection conditions, such as, for example, layered skin, available in multiple tones and textures to mimic a diverse span of age, race, and skin texture. In an embodiment, the layered skin can be removable and/or replaceable. The injection apparatus can simulate any human or animal part, such as, for example, the face, head, brain, neck, back, chest, spine, torso, arms, legs, hands, feet, mouth, or any other body part or portion of the body of interest. In an embodiment, the testing tool can be, for example a syringe or hypodermic needle. In an embodiment, the injection apparatus is reusable. In an embodiment, the injection apparatus is disposable.

In an embodiment a syringe for simulating injection is disclosed. The syringe can include a barrel having a portal at a distal end, and an electronics assembly having a light source at a distal end of the electronics assembly. The electronics assembly can be configured to fit inside the barrel with the light source positioned at the portal of the barrel. A needle can be attached to the barrel. The needle can have a fiber bundle extending axially through it such that the fiber bundle is in close-fitting relation with the light source.

In some embodiments a testing tool for use in an injection training system includes a barrel having a fitting at a distal end of the barrel. The fitting can have a portal, and the barrel can have an opening and a finger grip at a proximal end of the barrel. A plunger can be configured to fit in the opening of the barrel to apply a force directed axially toward the distal end of the barrel. The testing tool can include an electronics assembly that has a light source at its distal end and a force sensor at its proximal end. The electronics assembly can be configured to fit inside the barrel with the light source positioned at the portal of the fitting, and the force sensor positioned near the proximal end of the barrel. The force sensor can be configured to sense the force applied by the plunger. The testing tool can include a needle assembly attached to the fitting of the barrel. The needle assembly can have a hollow needle, a fiber bundle extending axially through the hollow needle, and a hub configured to secure the hollow needle and to attach the needle assembly to the fitting of the barrel. The needle assembly can be attached to the barrel such that the fiber bundle within the hollow needle is in close-fitting relation with the light source of the electronics assembly.

In an embodiment, a method of simulating an injection into a synthetic anatomical structure is disclosed. The synthetic anatomical structure can be configured to attenuate light emitted into it and to detect the attenuated light. The method can include providing a testing tool to simulate a syringe. The testing tool can be configured to emit light through a needle at a distal end of the testing tool. The method can also include inserting the needle into the synthetic anatomical structure such that the light emitted through the needle is attenuated and detected by the synthetic anatomical structure.

BRIEF DESCRIPTION OF THE DRAWINGS

FIG. 4B is a perspective view of an embodiment of a docking station.

FIGS. 13B, 13B1, and 13B2, collectively, illustrate a process flow diagram of a process to determine the position and orientation of a testing tool according to an embodiment of the disclosed injection training system.

FIG. 15B illustrates an embodiment of an injection training system comprising an injection apparatus, a testing tool, an output device and a plurality of optical tracking systems, in accordance with an embodiment of the present disclosure.

DETAILED DESCRIPTION

Figure 1:
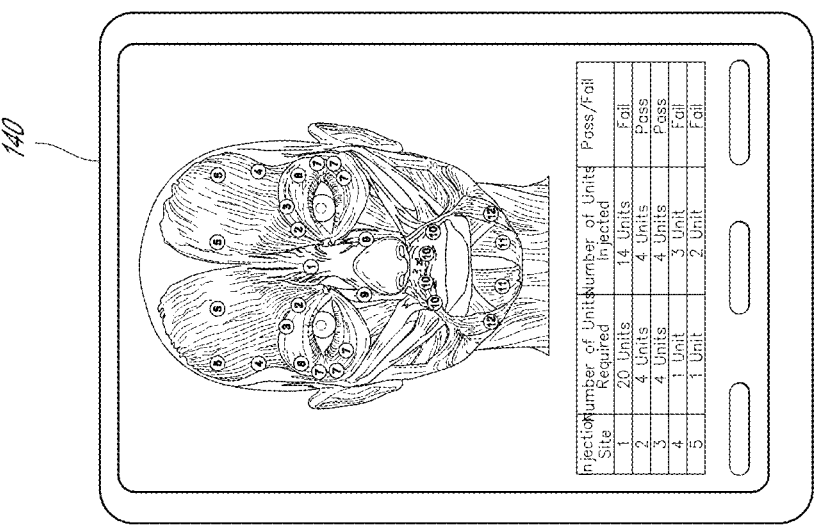
FIG. 1 illustrates an injection training system comprising an injection apparatus, a testing tool and an output device in accordance with an embodiment of the present disclosure.
Figure 1:
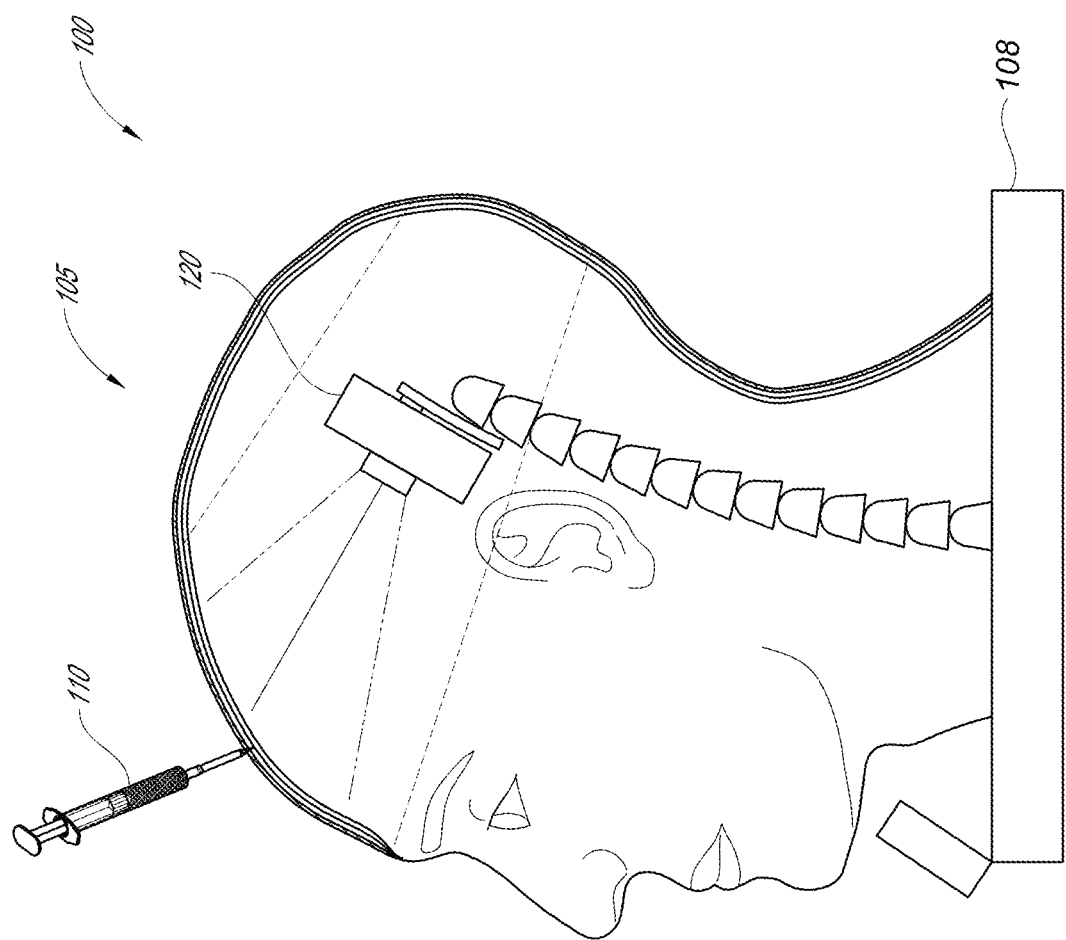

Embodiments will now be described with reference to the accompanying figures. The following description is merely illustrative in nature and is in no way intended to limit the disclosure, its application, or its uses. For purposes of clarity, the same reference numbers will be used in the drawings to identify similar elements. The terminology used in the description presented herein is not intended to be interpreted in any limited or restrictive manner, simply because it is being used in conjunction with a detailed description of certain specific embodiments of the disclosure. Furthermore, embodiments of the disclosure may include several novel features, no single one of which is solely responsible for its desirable attributes or which is essential to practicing the present disclosure. It should be understood that steps within a method may be executed in different order without altering the principles of the present disclosure.

FIG. 1 depicts an embodiment of an injection training system 100. An injection apparatus 105, comprising a synthetic anatomical structure, can be used for any type of injection training involved with administering diagnostic and therapeutic chemical substances. For example, injection training can be provided for epidural techniques and for intra-cardiac injections. In one embodiment, the injection apparatus 105 can anatomically model the face, neck, and head of a human or animal. Although not shown in the accompanying drawings, the injection apparatus 105 can model other injection sites including the chest, arms, mouth, back, buttocks, etc. The injection apparatus 105 may also represent any body part of a human or animal, including internal organs. In some embodiments, the injection apparatus 105 may include a simulated skull and layers of muscle and skin. The injection apparatus 105 can be positioned on a base 108 to facilitate use on flat surfaces, such as a table or desk.

A testing tool 110 is also illustrated which can be used with the injection apparatus 105 and in conjunction with a camera/light detector 120 located within the injection apparatus 105. The testing tool 110 may simulate any type of equipment used in connection with an injection or minimally invasive procedure, such as a needle, catheter or cannula. As described in further detail below, the camera/light detector 120 can capture visual indications of the user's injection using the testing tool 110. The visual indications provide an operator or user with information regarding the location, depth, pressure, or angle of the injection. In an embodiment, the testing tool 110 contains a light source that emits light through the needle portion of the testing tool 110 which is used to aid in obtaining the visual indications detectable by a camera/light detector 120. The light source can emit visible light. In an embodiment, a gradient of white light is emitted through the needle portion of the testing tool. Other colors of visible light can also be used, such as green, blue, red, yellow or any combination of those colors. In an alternative embodiment, the light source may emit light along a spectrum of visible or non-visible light, such as fluorescent, ultraviolet, or infrared light. In some embodiments, the light emitted from the light source is attenuated differently depending on which layer of simulated skin, muscle, or tissue the injection apparatus 105 is penetrated. Different colors, directions, graph lines, visual patterns, polarization, fluorescence, or intensities of light can be captured by the camera/light detector 120 as the testing tool 110 is inserted through the different layers of material surrounding the injection apparatus 105. The resulting light detected by the camera/light detector 120 can be used to determine the location of the injection, the pressure exerted by the user, the angle of injection, and/or the depth of the injection. This information can be detected, for example by a camera/light detector 120, and communicated to a user interface/display device 140 for training, testing, and/or certification purposes. In some embodiments, information used to determine the location of the injection, the pressure exerted by the user, the angle of injection, and/or the depth of the injection can be collected by the testing tool 110 and communicated to a user interface/display device 140 and/or a camera/light detector 120 for training, testing and certification purposes.

The camera/light detector 120 within the simulated skull of the injection apparatus 105 captures the attenuated light emitted by the testing tool 110, simulating an injection, through video recording and/or photographic images. The camera/light detector 120 can include a processor and can communicate output from the camera/light detector 120 to a user interface/display device 140. The information gathered from the camera/light detector 120 and testing tool 110 may be communicated to a user interface/display device 140 for data collection, testing or certification purposes. Output from the camera/light detector 120 can be raw or processed video or images obtained from the camera/light detector 120. The processor of the camera/light detector 120 can include software configured to interpret the visual indications for testing purposes or can merely pass images to the user interface/display device 140 for further processing. In an embodiment, the user interface/display device 140 can also communicate instructions to the camera/light detector 120 and/or to the testing tool 110.

Attention is now directed to embodiments of the testing tool 110. Although disclosed with reference to particular embodiments of the testing tool 110, an artisan will recognize from the disclosure herein that there is a large number and wide variety of embodiments and configurations that may be used to perform the functions of a testing tool 110 as described herein.

Figure 2A:
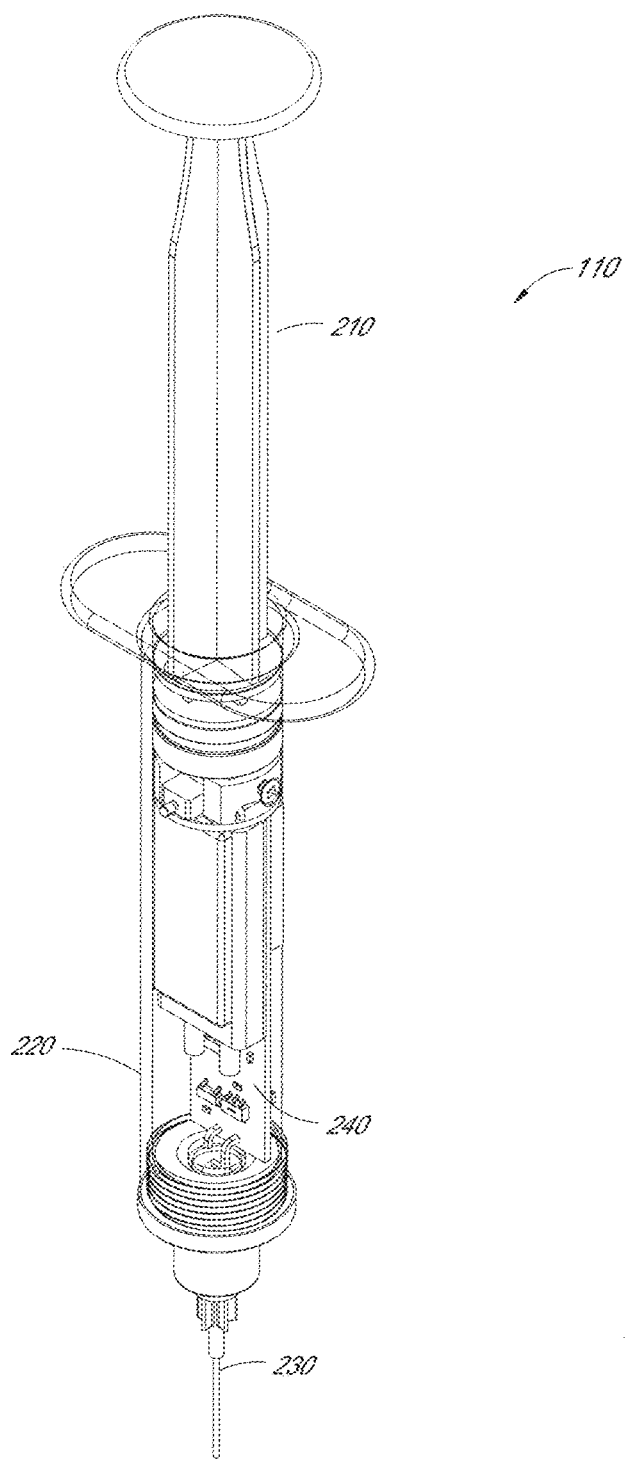
FIG. 2A is a perspective view of an embodiment of an assembled testing tool.
Figure 2B:
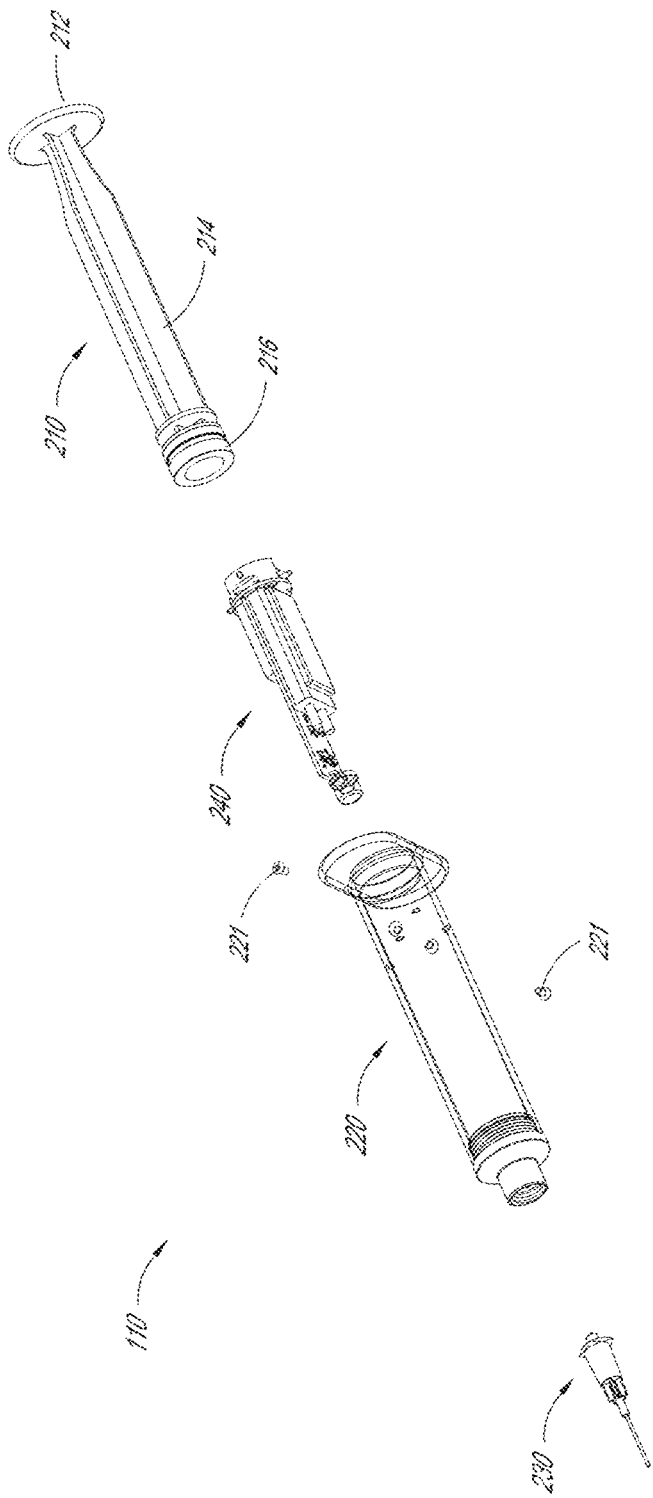
FIG. 2B is an exploded perspective view of an embodiment of a testing tool.

FIGS. 2A and 2B illustrate (in assembled and exploded views, respectively) an embodiment of the testing tool 110 adapted for use to train individuals to inject materials with a syringe. In an embodiment the testing tool 110 includes a plunger 210, a barrel 220, a needle assembly 230, and an electronics assembly 240. Also illustrated are fasteners 221, such as screws, to secure portions of the electronics assembly 240 to the barrel 220.

For purposes of this description, the end of the test tool 110 toward the needle assembly 230 is referred to as the "distal end," and motion or direction toward the distal end is described as being "distal." The end of the test tool 110 longitudinally opposite the distal end is referred to as "the proximal end," and motion or direction toward the proximal end is described as being "proximal."

The plunger 210 can be manufactured by using many types of materials including polypropylene, glass, and other materials known to skilled artisans. The plunger 210 includes a top portion 212 at the proximal end of the plunger 210. The plunger 210 also includes a shaft 214 which, in an embodiment, is x-shaped. In some embodiments the plunger shaft 214 can be cylindrical or any other shape suitable to perform the function of a plunger 210. In some embodiments, the plunger 210 is collapsible to simulate the process of injecting material into a patient. In some embodiments the plunger 210 is configured to house the electronics assembly 240. In some embodiments the plunger 210 is collapsible and configured to measure the plunger's 210 motion of contraction to determine a volume of material that would have been injected under the simulated circumstances and conditions of use of the testing tool 110. The collapsible plunger 210 can be reset by pulling it back to its original, un-collapsed (or extended) position. In some embodiments data reflecting the position of the plunger 210 is collected and communicated to, for example, the user interface/display device 140 and/or to the camera/light detector 120. In an embodiment the testing tool 110 includes a hydraulic and/or a friction-based device, acting against the plunger 210, to simulate the force of resistance that a liquid material with certain properties of viscosity, would exert against the plunger 210 as it is injected into a patient.

At the distal end of the plunger 210 is a seal 216, which is made of rubber in an embodiment. A skilled artisan will appreciate that in some embodiments the plunger seal 216 may be made from any material suitable for creating a seal between the plunger 210 and the inside walls of the barrel 220, such as various types of elastomers and/or polymers. In some embodiments the plunger 210 lacks a seal 216 because the testing tool 110 is not used to deliver liquid, chemical substances, thereby lacking a need to form a seal.

Figure 2C:
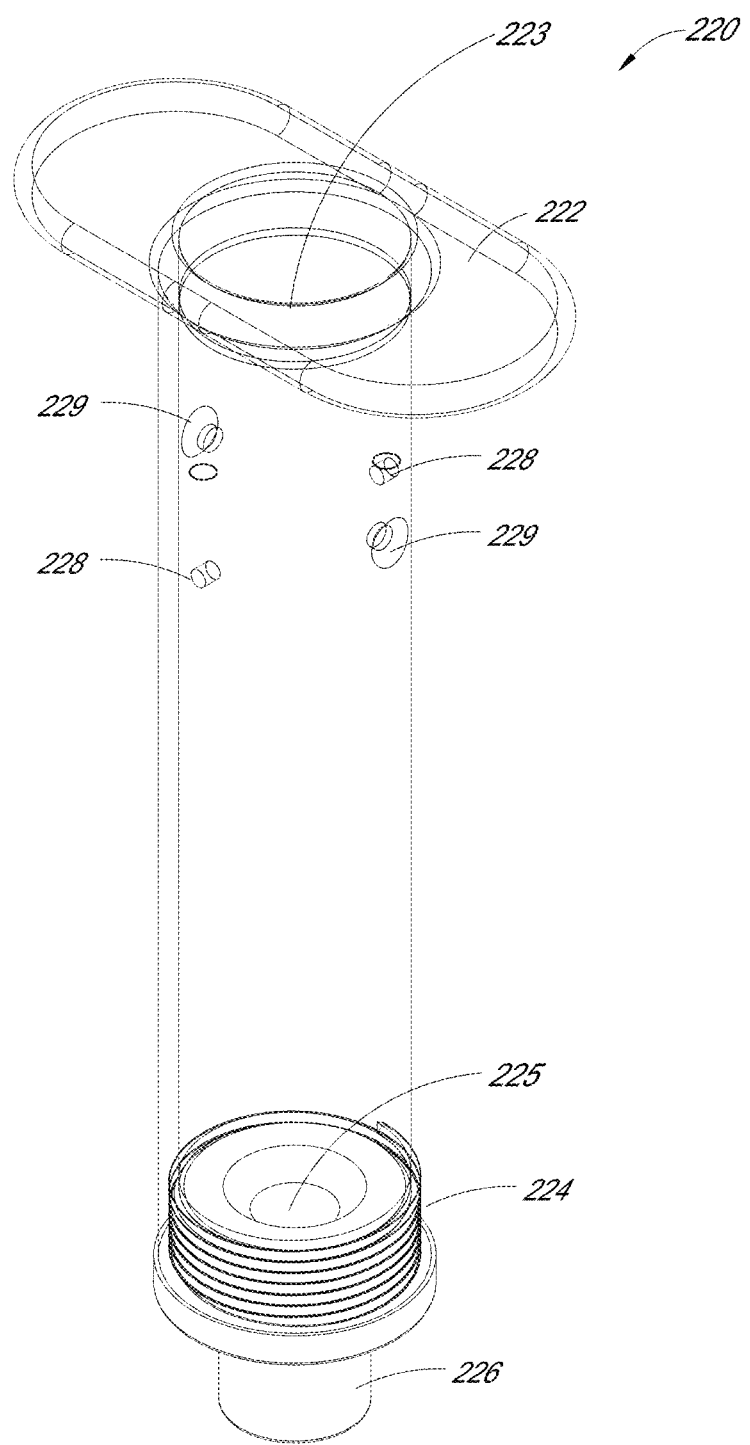
FIG. 2C is a perspective view of an embodiment of a barrel of a testing tool.

FIG. 2C is a perspective view of an embodiment of a barrel 220 of a testing tool 110. The barrel 220 can be made from many types of materials including polypropylene, glass, and other materials known to skilled artisans. The barrel 220 includes a grip 222 and an opening 223 at the barrel's proximal end. The grip 222 provides finger support for reciprocation of the plunger 210 relative to the barrel 220 during use for training. At the distal end of the barrel 220 is a threaded portion 224 configured to receive a fitting 226. The fitting has a portal 225 through which light passes from a light source (on the electronics assembly 240) to a fiber bundle housed within a hollow needle (in the needle assembly 230). In some embodiments the fitting 226 can be a Luer fitting, a standardized set of fittings used to make leak-free mechanical connections between a male-taper fitting and a mating female part on medical and laboratory instruments, including hypodermic syringe tips and needles. In some embodiments the fitting 226 is not tapered. Advantageously, in some embodiments, the fitting 226 can accommodate numerous configurations of needle assemblies 230 corresponding to various injection indications and applications. In some embodiments a customized fitting 226 includes a thread with no taper component to facilitate intimate contact between a light source and a fiber bundle that transmits the emitted light into the injection apparatus 105. In an embodiment the barrel 220 includes bores 228 configured to receive connector pins attached to the electronics assembly 240 to enable charging of a battery when, for example, the testing tool 110 is housed in a docking station. The barrel 220 also includes holes 229 through which fasteners, such as screws, can be used to secure the electronics assembly 240 to the barrel 220.

Figure 2D:
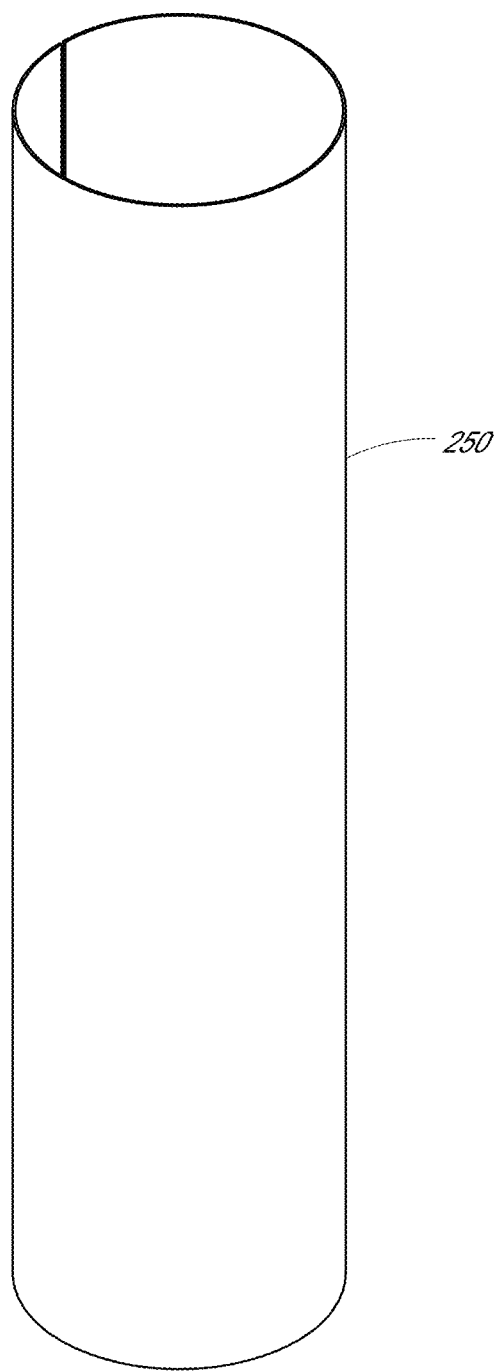
FIG. 2D is a perspective view of an embodiment of a label of a testing tool.

FIG. 2D is a perspective view of an embodiment of a label 250 of a testing tool 110. In an embodiment, the label 250 is configured to fit inside the barrel 220 in close-fitting relation with an inner wall of the barrel 220. In an embodiment the label 250 is configured to fit outside the barrel 220 in close-fitting relation with an outer wall of the barrel 220. The label 250 can be configured to present any type of information including, among other things, branding and/or instructional information.

Figure 2E:
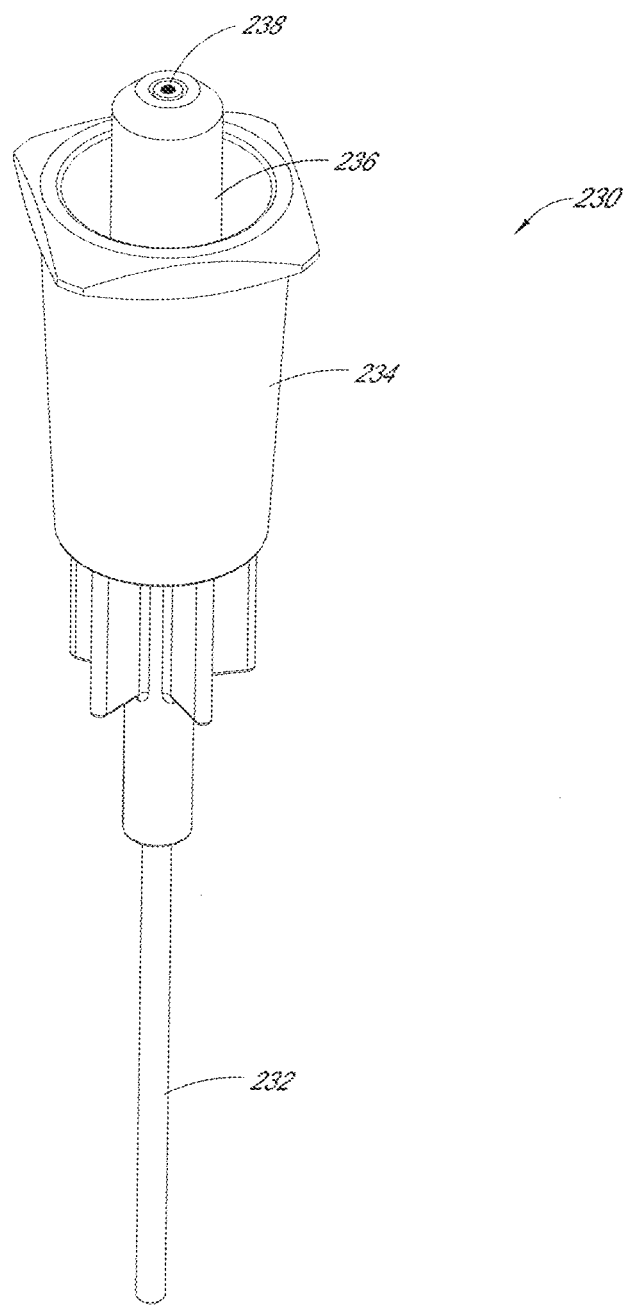
FIG. 2E is a perspective view of an embodiment of a needle assembly of a testing tool.
Figure 2F:
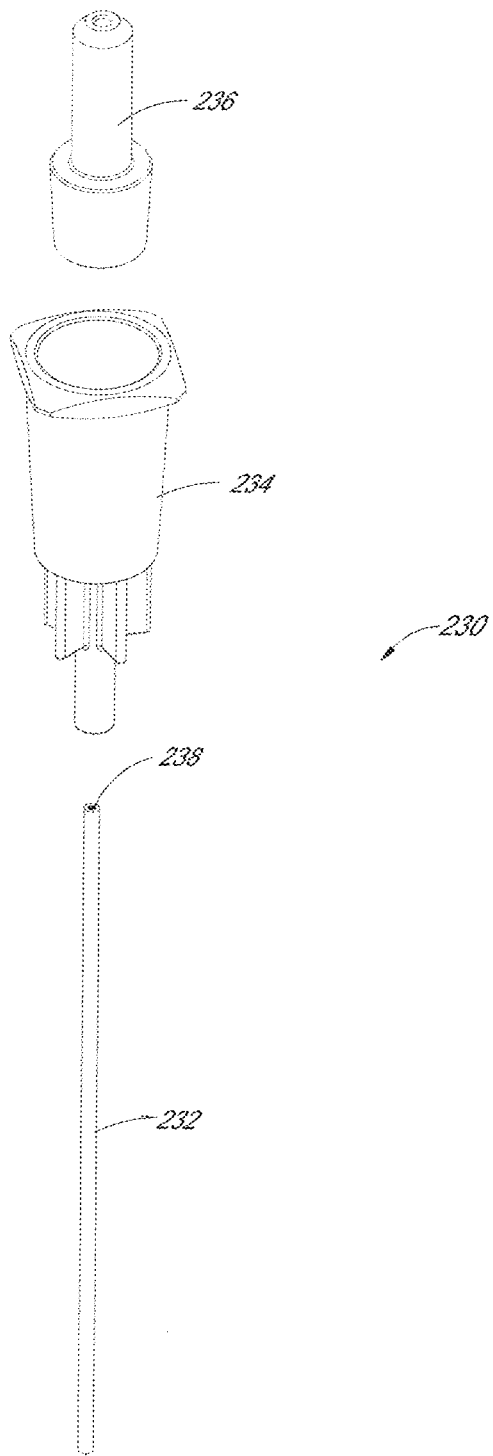
FIG. 2F is an exploded perspective view of an embodiment of a needle assembly of a testing tool.
Figure 2G:
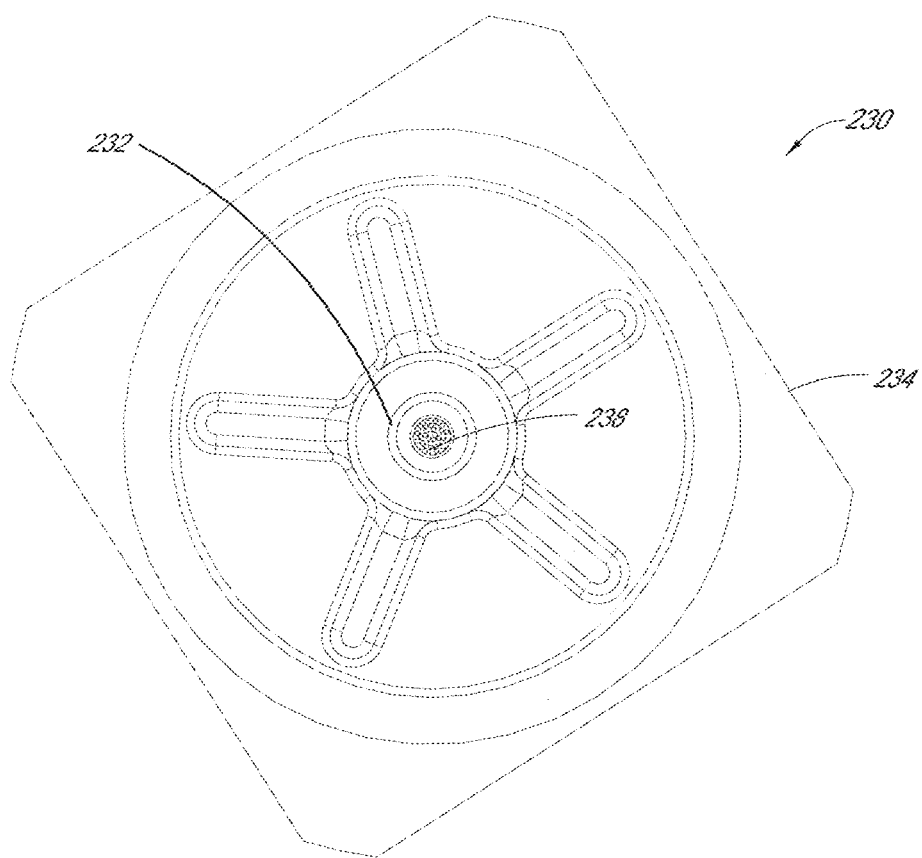
FIG. 2G is a top view of the distal end of an embodiment of the needle assembly of a testing tool.

FIGS. 2E-2F are perspective views (assembled and exploded, respectively) of an embodiment of a needle assembly 230 of a testing tool 110, including a hollow needle 232, a needle hub 234, an adapter 236, and a fiber bundle 238 positioned centrally along the longitudinal axis of the needle assembly 230 and configured to transmit light at the distal end of the testing tool 110. In some embodiments a needle hub 234 is configured to connect directly to the fitting 226 of the barrel 220, thereby eliminating the need for an adapter 236. The fiber bundle 238 is housed within the hollow needle 232. In an embodiment the hollow needle 232 is made from hypodermic tubing. A wide variety of hollow needles 232 used for, among other things, hypodermic applications, have outer diameters described by gauge numbers ranging from 7 to 34. Hollow needles 232 within this gauge range can be used in various embodiments of the disclosed needle assembly 230. Smaller gauge numbers indicate larger outer diameters. The inner diameters of such hollow needles 232 depend on both gauge and wall thickness. Thin-wall needles have identical outer diameters, but larger inner diameters, for a given gauge. Thin-wall needles can also be used in various embodiments of the needle assembly 230. In an embodiment the hollow needle 232 is made of stainless steel and has a gauge size of 23RW. A skilled artisan will appreciate that the hollow needle 232 can be of many different gauge sizes without departing from the scope of the disclosure herein. Free space between the fiber bundle 238 and the inner wall of the hollow needle 232 can be potted with optical epoxy. The proximal and distal ends of the hollow needle 232, having the fiber bundle 238 secured inside it, can be polished flat. The hollow needle 232 can be epoxy-bonded to the needle hub 234, which attaches to the fitting 226 on the barrel 220. FIG. 2G is a top view of the distal end of the needle assembly 230 illustrating the fiber bundle 238 housed and secured with optical epoxy within the hollow needle 232.

Figure 3A:
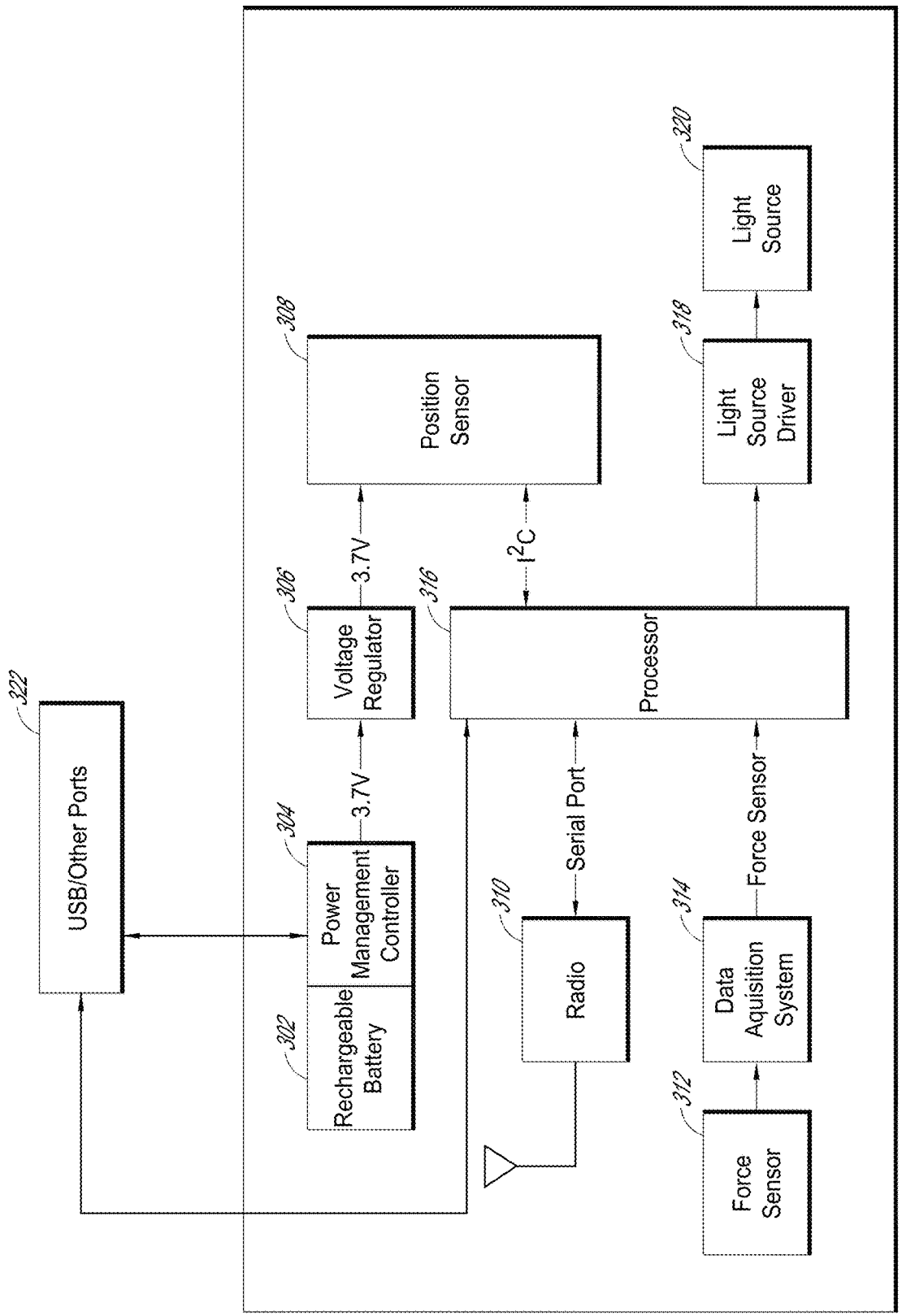
FIG. 3A is a simplified block diagram of an embodiment of an electronics assembly of a testing tool.

FIG. 3A is a simplified block diagram of an embodiment of the electronics assembly 240 of the testing tool 110. Functionally, among other things, the electronics assembly 240 emits light from a light source 320, measures the electronic assembly's 240 physical position and/or orientation with a position sensor 308, and measures force applied to the plunger 210 by a force sensor 312. The electronics assembly 240 communicates the measured position information and the measured force information to, for example, an external user interface/display device 140, and/or to a camera/light detector 120, by way of a communications protocol. In some embodiments the electronics assembly 240 communicates data by way of a USB port 322 using a cable that has a minimal diameter and is highly compliant. In some embodiments the electronics assembly 240 communicates data by way of a radio 310 employing, for example, a Bluetooth wireless communications protocol.

As illustrated in FIG. 3A, an embodiment of the electronics assembly 240 includes a battery 302, a power management controller 304, a voltage regulator 306, a position sensor 308, a radio 310, a force sensor 312, a data acquisition system 314, one or more processors 316, a light source driver 318, a light source 320 and one or more power/communication ports 322. In some embodiments the battery 302 is rechargeable, and the power management controller 304 is configured to communicate with an external battery-charging power/communication port 322, such as, for example, a universal serial bus (USB) port. The battery 302 can supply power to the components and circuitry of the electronics assembly 240. In an embodiment the battery 302 is an ultrathin, rechargeable, lithium polymer cell. A skilled artisan will appreciate that numerous other batteries can be used in the disclosed electronics assembly 240.

According to an embodiment, the electronics assembly 240 comprises a battery 302 and a light source 320, where the electronics assembly 240 is configured to emit light through the hollow needle 232 to achieve basic functionality of the disclosed testing tool 110. In an embodiment, the electronics assembly 240 comprises a light source 320 and a port 322 through which an external power source may be electrically connected to energize the light source 320 to achieve basic functionality of the testing tool 110. One skilled in the art will appreciate that various functional capabilities described in connection with embodiments of the electronics assembly 240 can be implemented in numerous ways. To illustrate this point, illustrative components, blocks, modules, and circuits have been described generally in terms of their functionality. The manner by which such functionality is implemented can depend upon the particular application and design constraints imposed on the overall system. The described functionality can be implemented in varying ways for each particular application, but such embodiment decisions should not be interpreted as causing a departure from the scope of the present disclosure.

To operate effectively in the injection training system 100, the light source 320 must be sensed by the camera/light detector 120. In an embodiment the camera/light detector 120 is configured to sense visible light and infrared light. In an embodiment the light source is a light emitting diode (LED) that emits low, infrared light at a wavelength of 810 nanometers (nm). In an embodiment the light source 320 is a laser that emits low infrared light at a wavelength of 850 nm. In an embodiment the light source 320 has a narrow emission angle of twenty degrees or less. In an embodiment, the light source 320 is an LED that has its dome removed and is polished flat to facilitate intimate contact with the proximal end of the fiber bundle 238 and the light source 320 when the testing tool 110 is assembled. In some embodiments lenses, reflectors, and/or fiber optic tapers are coupled to the light source 320 to focus and/or to intensify the emitted light in the direction of the fiber bundle 238. In some embodiments the intensity of the light emitted by the testing tool 110 is proportional to the amount of pressure applied to a plunger 210 of the testing tool 110, thereby simulating a process by which liquid material is injected through the testing tool 110. A skilled artisan will appreciate that many other light sources 320 and light ranges of various wavelengths can be used in the disclosed training system 100 without departing from the scope of the disclosure herein.

In an embodiment the force sensor 312 is configured to sense up to twenty pounds (20 lbs.) of force with a 2 percent accuracy factor. In an embodiment the position sensor 308 is a three-axis digital gyroscope with angle resolution of two degrees and with a sensor drift adjustment capability (pitch, yaw and roll) of one degree. A skilled artisan will appreciate that numerous other position sensors 308 and force sensors 312 can be used in the disclosed electronics assembly 240 without departing from the scope of the disclosure herein. In an embodiment the electronics assembly includes a power conditioning component, such as a voltage regulator 306, to enable operation of the position sensor 308 and the force sensor 312. In an embodiment the position sensor 308 senses the position of the testing tool 110 in three-dimensional space, and the sensed position information is communicated to the user interface/display device 140 and/or to the camera/light detector 120.

Figure 3B:
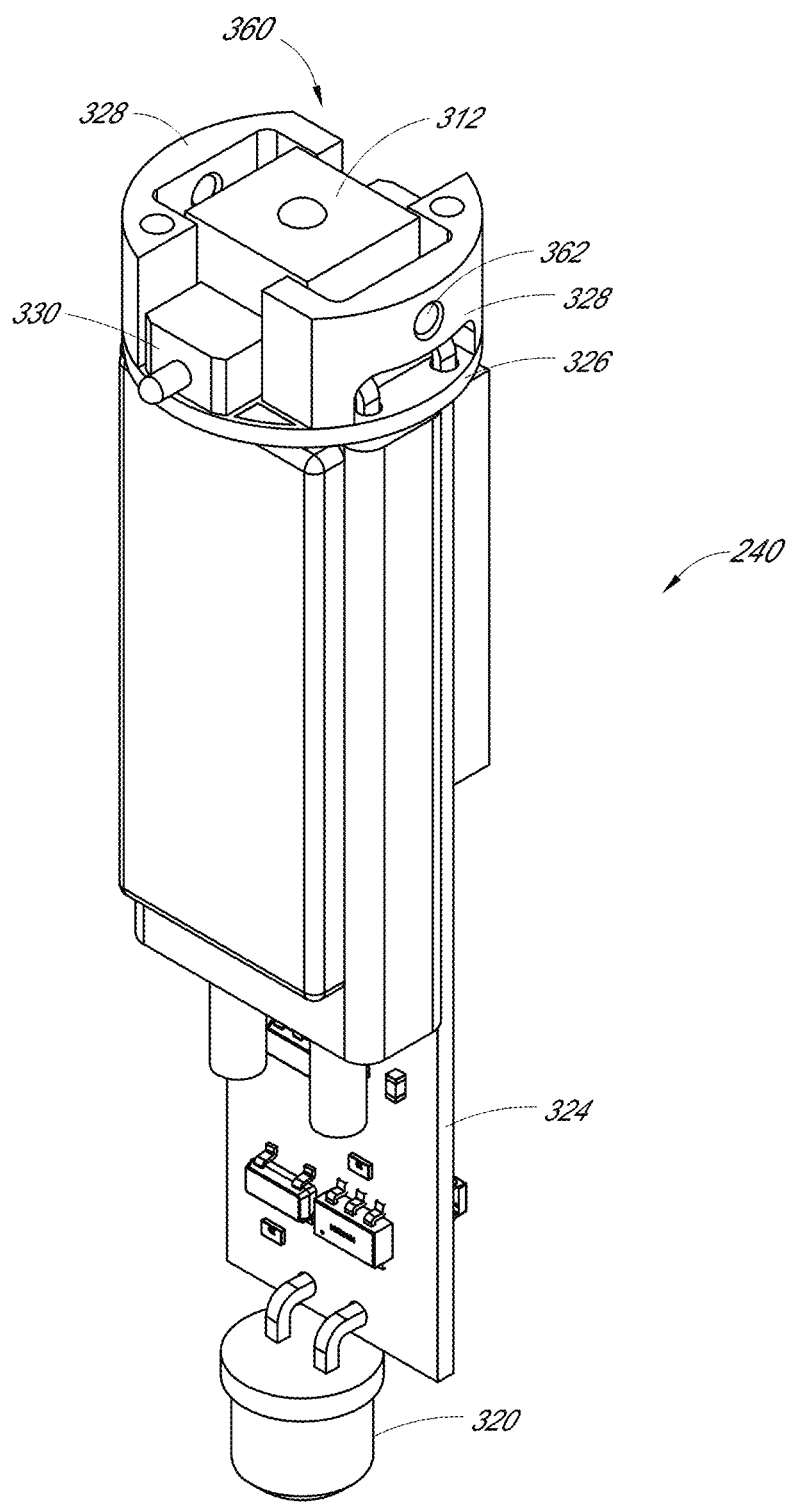
FIG. 3B is a perspective view of an embodiment of an electronics assembly of a testing tool.

FIG. 3B is a perspective view of an embodiment of the electronics assembly 240. Advantageously, the electronics assembly 240 is configured to fit within the barrel 220 of the testing tool 110. A rectangular circuit board 324 comprises a substrate onto which several components of the assembly 240 are attached. In an embodiment the electronics assembly includes the battery 302, the power management controller 304, the voltage regulator 306, the light source driver 318 and the light source 320. When the electronics assembly 240 is configured in the testing tool 110, it is positioned such that the light source 320 is located at the distal end of the testing tool 110, within the fitting 226 so as to make intimate contact with the proximal end of the fiber bundle 238, which is secured to the needle assembly 230.

Figure 3C:
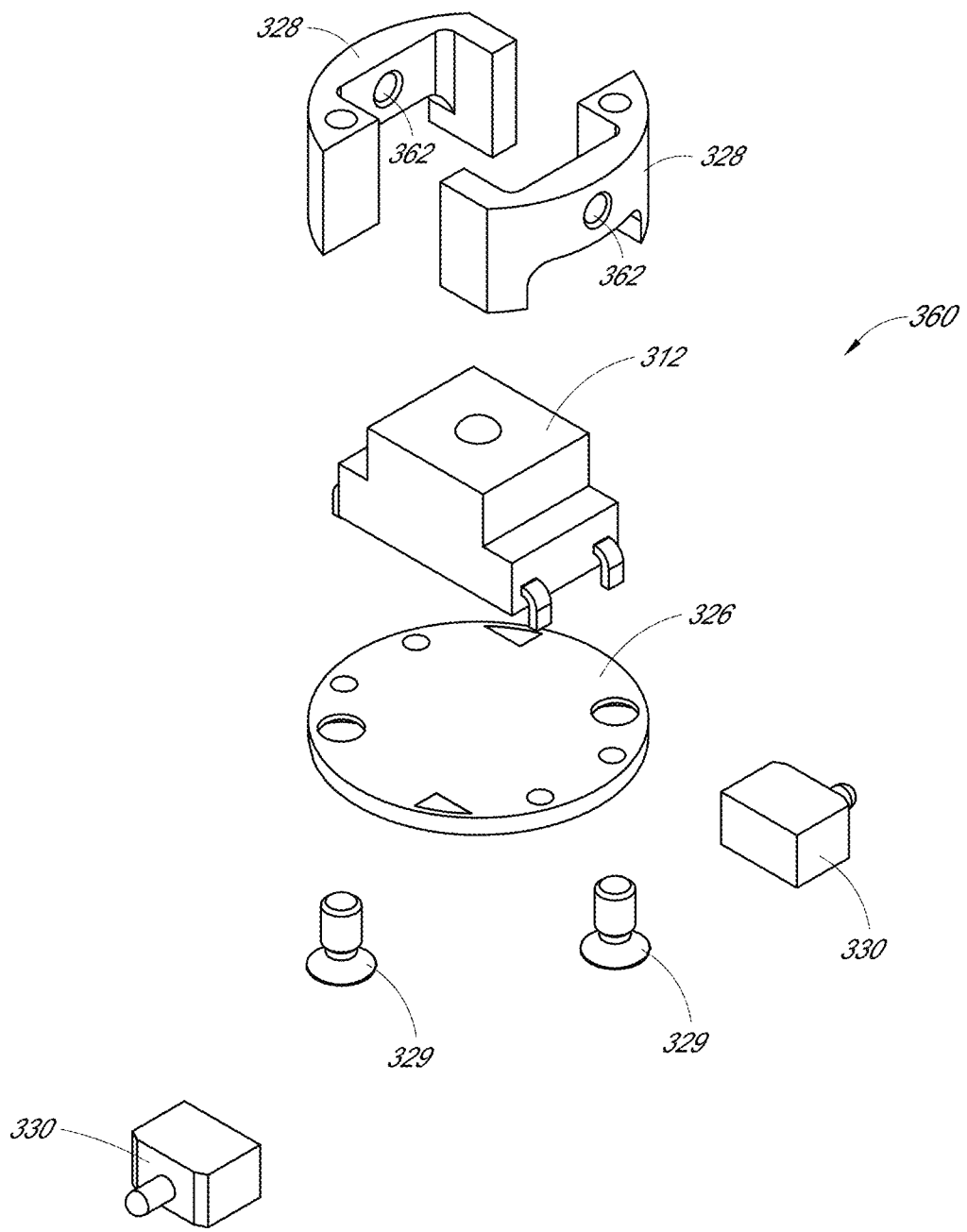
FIG. 3C is an exploded perspective view of an embodiment of a force sensor sub-assembly of an electronics assembly of a testing tool.

In an embodiment the electronics assembly 240 also includes a force sensor sub-assembly 360 illustrated in FIG. 3B and in FIG. 3C, in assembled and exploded views, respectively. The force sensor sub-assembly 360 has a circular printed circuit board 326 comprising a substrate to which several components of the force sensor sub-assembly 360 are attached, including a force sensor 312, backstops 328, and connector pins 330. The backstops 328 provide structural support for the force sensor sub-assembly 360 and serve as a mechanism by which to secure the force sensor sub-assembly 360 to the barrel 220. The circular printed circuit board 326 is attached to the two backstops 328 with fasteners 329. The connector pins 330 are used to couple to an external power source to charge the battery 302. In an embodiment, the connector pins 330 are spring-loaded contacts that are soldered to the circular printed circuit board 326 and configured to fit through the bores 228 in the barrel 220. By protruding through the bores 228 the connector pins 330 are able to make electrical connection with an external power source to enable charging of the battery 302.

When positioned within the testing tool 110, the force sensor sub-assembly 360 is oriented substantially perpendicular to the rectangular printed circuit board 324 such that the force sensor 312 is configured to sense axial force applied in the distal direction by the plunger 210. The force sensor sub-assembly 360 is secured to the barrel 220 by fasteners 221 (shown in FIG. 2B), such as flat head screws, that are inserted through the holes 229 of the barrel 220 and secured into threaded screw holes 362 located centrally on the backstops 328. In this manner the force sensor sub-assembly 360 resists being deflected in response to force applied to the force sensor 312 by the plunger 210.

In an embodiment the circular printed circuit board 326 is electrically coupled to the proximal end of the rectangular printed circuit board 324 to enable electrical communication between the force sensor 312 and the processor 316, and between the connector pins 330 and the power management controller 304.

An artisan will recognize from the disclosure herein that the functionality of the electronics assembly 240 may be accomplished in many different ways, using many different electronic components and organized in a large number of ways without departing from the scope of the disclosure herein.

Referring back to FIGS. 2A-2B, assembly of the testing tool 110, for some embodiments, is accomplished by securing the needle assembly 230 to the fitting 226, and by securing the electronics assembly 240 into the barrel 220. Spring-loaded connector pins 330 retract inward to permit the electronics assembly 240 to move to the distal end of the inside of the barrel 220, such that the light source 320 is in close intimate relation with the proximal end of the fiber bundle 238 of the needle assembly 230. The electronics assembly 240 may be rotated axially such that the spring-loaded connector pins 330 are aligned with bore holes 228, at which point the spring-loaded connector pins will expand to lock into position. Fasteners 221 are then used to secure the electronics assembly 240 to the barrel 220. The plunger 210 is inserted into the proximal end of the barrel 220.

In some embodiments the plunger 210 is configured to move distally through the barrel 220 when force is applied to the plunger 210, thereby simulating the plunger motion associated with injecting material into a patient. In an embodiment, the plunger shaft 214 is cylindrical, having an outer diameter slightly less than the inner diameter of the barrel 220. As the cylindrical plunger shaft 214 moves through the barrel 220 in the distal direction, the plunger shaft 214 slides around and envelops the electronics assembly 240. In an embodiment, a resistance device offers a resistive force in response to the force applied to the plunger 210, corresponding to a resistive force experienced when injecting liquid materials into a patient. In an embodiment the resistive device is a friction-based device. In an embodiment the resistive device is a fluid-based device. In an embodiment the resistive device includes a spring configured to apply a resistive force to the plunger 210. One skilled in the art will readily appreciate that there are many ways by which to achieve the functionality of the resistive device. In an embodiment, the force applied by the plunger 210 and the force applied by the resistive device are sensed and communicated to a user interface/display device 140 and/or to a camera/light detector 120.

In some embodiments the plunger shaft 214 is configured to collapse telescopically to simulate plunger motion associated with injecting material into a patient. In some embodiments, the collapsible plunger shaft 214 is configured to sense positional displacement of the plunger shaft 214 and to communicate the plunger shaft 214 displacement coordinates to a user interface/display device 140 and/or to a camera/light detector 120. In some embodiments measurements of the position of a movable, collapsible or telescoping plunger 210 are communicated to a user interface/display device 140 and/or to a camera/light detector 120 and used to determine whether proper doses are being delivered.

In some embodiments, the electronics assembly 240 is positioned within the plunger shaft 214, and is configured to move distally and proximally through the barrel 220, along with the plunger 210. Placing the electronics assembly 240 in a hollowed shaft 214 of the plunger 210 makes the barrel 220 available to hold a therapeutic agent that can be injected during the training into the injection apparatus 105. The position sensor 308 is configured to obtain position and orientation information of the testing tool 110 and of the plunger 210, and to wirelessly transmit the information to the user interface/display device 140. In an embodiment, the force sensor sub-assembly 360 can be positioned within the shaft 214 of the plunger 210 to measure the resistive force of the therapeutic agent in the barrel 220, as the injection is applied. The measured force information can be wirelessly transmitted to the user interface/display device 140. Illustratively, in such an embodiment the testing tool 110 operates in a manner similar to a syringe in that the testing tool 110 is configured to deliver a therapeutic agent through the needle 232 into the injection apparatus 105. In some embodiments the electronics assembly 240 is positioned within the plunger shaft 214 and is configured to move distally and proximally through the barrel 220, along with the plunger 210. The light source 320 is positioned at the distal end of the barrel 220, and a flexible connector connects the light source 320 to the electronics assembly 240. In some embodiments the flexible connector connecting the light source 320 to the electronics assembly is extendable and retractable. Accordingly, the plunger 210 is able to move axially into and out of the barrel 220, while the light source is configured to emit light through the tip 233 of the hollow needle 232.

Figure 4A:
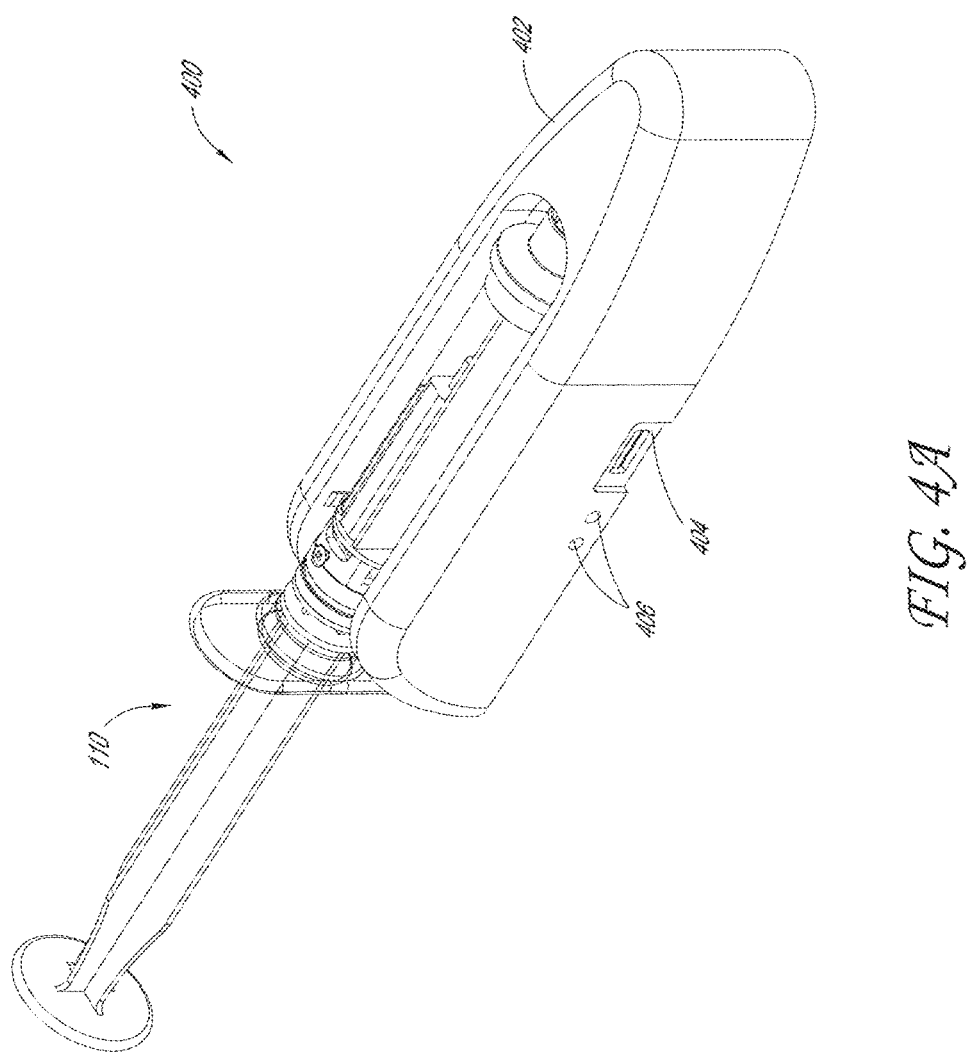
FIG. 4A is a perspective view of an embodiment of a testing tool docked in an embodiment of a docking station.
Figure 4C:
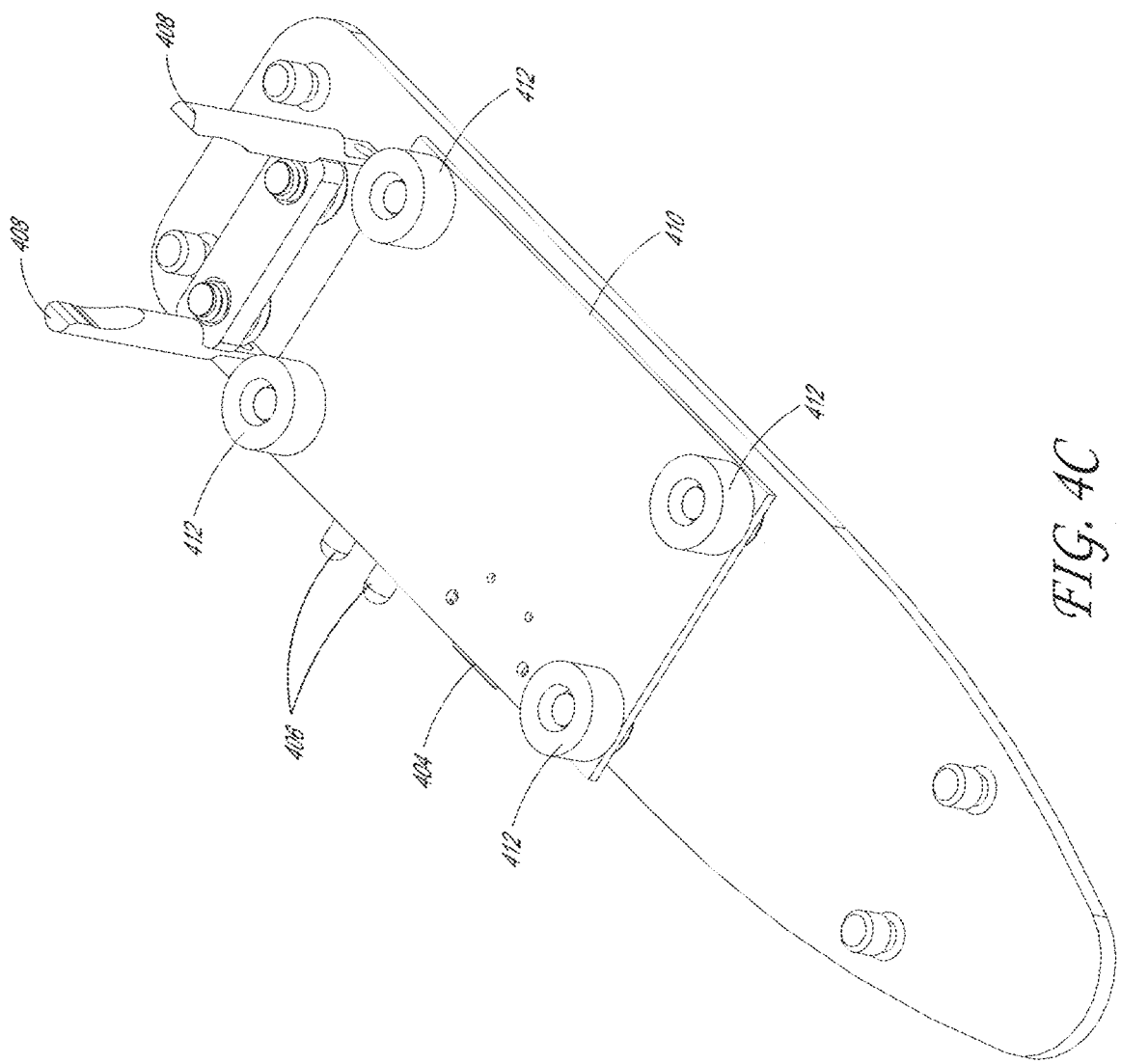
FIG. 4C is a perspective view of an embodiment of a docking station with its cover removed.

FIG. 4A illustrates an embodiment of a testing tool 110 docked in a docking station 400. The docking station 400 includes a dock cover 402, a USB port 404, and two indicator lights 406. The docking station 400 is contoured to accommodate the testing tool 110 such that the connector pins 330 of the testing tool 110 are in contact with contact pins 408 to facilitate charging of the battery 302. FIG. 4B provides a view of a contact pin 408 of the docking station 400. FIG. 4C illustrates the docking station 400 with its cover 402 removed revealing a dock circuit board 410 electrically coupled to the USB port 404 and to the indicator lights 406. The dock circuit board 410 is also electrically coupled to contact pins 408 such that when a connection is made from, for example, a standard power outlet to the USB port 404, the contact pins are configured to support charging of the battery 302 of the testing tool 110 when the testing tool is docked in the docking station 400. Standoff elements 412 are employed to provide appropriate spacing within the structure of the docking station 400.

In some embodiments of the injection training system 100, an injection training apparatus 105 or method can use one or more three-dimensional (3D) position sensors to determine a position of a testing tool 110, such as a syringe and/or needle, in an artificial patient injection site (such as, for example, an artificial face). One or more 3D position sensors can also be used for training caregivers on performing injections where accurate positioning is important, such as in facial injections (e.g., Botox®), spinal injections, and/or the additional injections described above.

By integrating one or more 3D sensors, the injection training apparatus and method may provide enhanced accuracy when tracking the trainee's injection technique. Increased training accuracy can facilitate increased detail on the feedback provided to the trainee. The features discussed below with reference to FIGS. 5-11 may be included, in whole or part, with the training systems, methods, and devices described herein.

Figure 5:
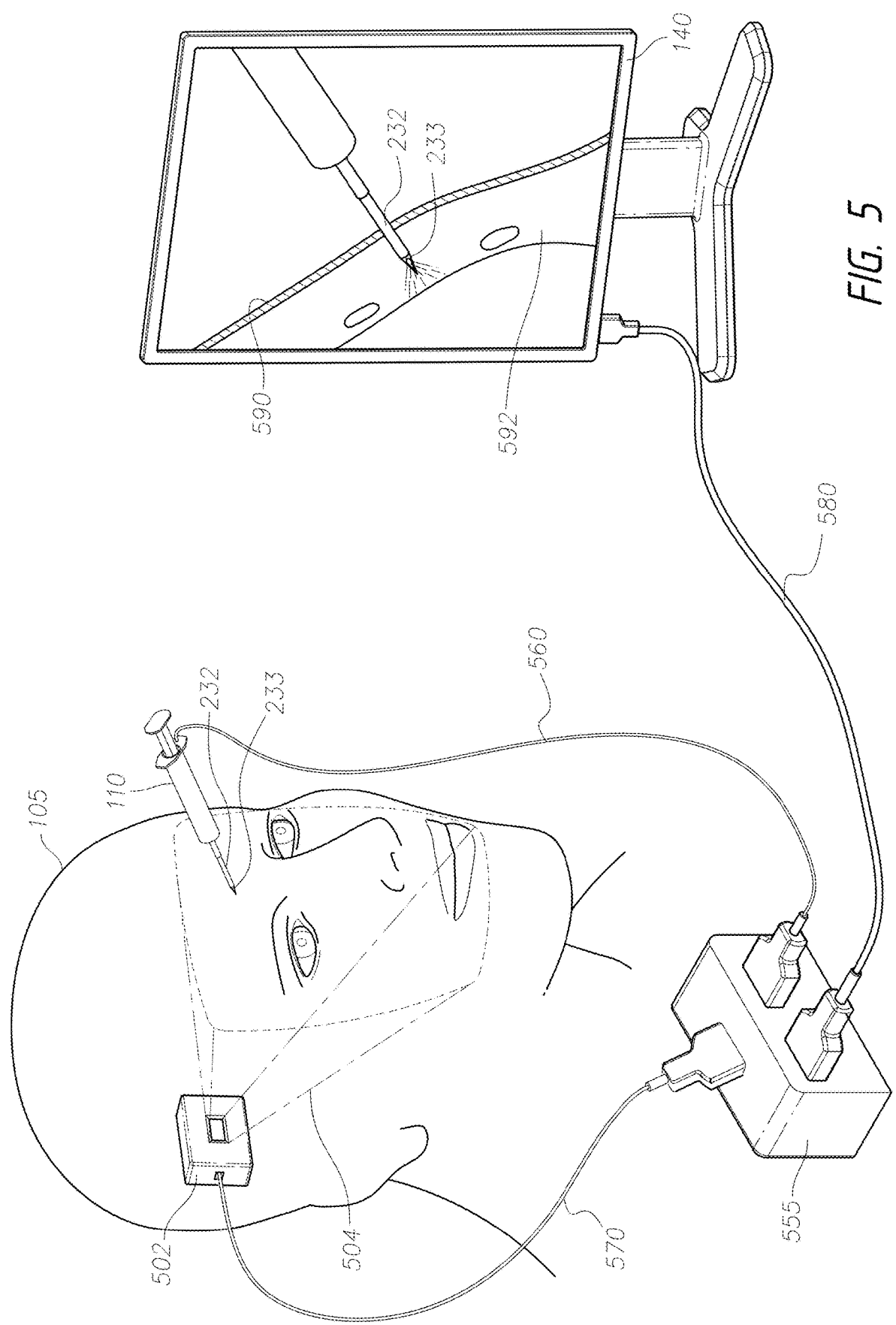
FIG. 5 illustrates an embodiment of the injection training system.

FIG. 5 illustrates an embodiment of the injection apparatus 105, testing tool 110 and user interface/display device 140. The injection apparatus 105 shown forms a head bust with realistic look and feel of human flesh. The external surface of the injection apparatus 105 may be a substantially synthetic or simulated skin. The synthetic or simulated skin can be an opaque rubber or other material which simulates skin and facial features of real patients. Underlying the skin may be a layer of substantially clear rubber (and/or any suitable elastomer) which simulates the viscosity, elasticity, and feel of skin, muscle, nerve, and bone tissue of a patient. The opaque skin and clear underlay may be capable of being pierced by a needle. It should be noted that the injection apparatus 105 need not include colored underlying skin to attenuate light.

The injection apparatus 105 is hollow and includes, within the cavity, a three-dimensional (3D) sensor 502. The 3D sensor 502 may include a camera, an array of light detectors or other sensor(s) capable of detecting a location of an object in three dimensions. The 3D sensor 502 is configured to detect a position of a needle and/or to view the interior surface of the injection apparatus 105. A field of view 504 is established in front of the 3D sensor 502. The field of view 504 represents an area in which the 3D sensor 502 may detect light.

A testing tool 110 is also shown. The testing tool 110 may be implemented as a syringe equipped with a light emitting needle, for example, as described in greater detail above. The light emitted by the testing tool 110 may be detected by the 3D sensor 502.

As shown in FIG. 5, the 3D sensor 502 and the testing tool 110 are coupled with a signal processing and display interface 555 via cables 560 and 570. The signal processing and display interface 555 can include one or more processors configured to receive and process information, provided from the 3D sensor 502 and/or from the testing tool 110 that corresponds to the position of the testing tool 110 relative to the injection apparatus 105. Illustratively, the processing and display interface 555 processes the received information from the 3D sensor 502 and from the testing tool 110 to determine the testing tool's 110 position relative to the injection apparatus 105. Although illustrated in FIG. 5 as being coupled by wires, coupling between the 3D sensor 502, the testing tool 110, and the user interface/display 140 can be accomplished via wired, wireless, or a combination of wired and wireless configurations. Moreover, the processing and interface 555 can be incorporated into the user interface/display 140. The method of coupling the 3D sensor 502 need not be identical to the method of coupling used for the testing tool 110.

In use, as illustrated in FIG. 5, a trainee punctures the face of the injection apparatus 105 with the testing tool 110 which is emitting light from a tip 233 of the hollow needle 232. When the tip 233 passes through the opaque skin layer of the injection apparatus 105, the 3D sensor 502 is configured to detect the light emitted from the tip 233 and to determine the three-dimensional position, in space, of the tip 233. The three-dimensional position information is transmitted to the signal processing and display interface 555, which is configured to communicate the three-dimensional position information to the user interface/display device 140. The user interface/display device 140 integrates the communicated position information into a digital model of the head bust injection apparatus 105. The user interface/display device 140 may be configured to present a visual representation of the position of the needle tip 233 relative to the injection site on the injection apparatus 105. The user interface/display device 140 allows the trainee to evaluate the actual needle position, as represented on the user interface/display device 140, in comparison to the ideal position, which is also represented on the user interface/display device 140. The user interface/display device 140, shown in FIG. 5, is coupled with the signal processing and display interface 555 by a cable 580. The coupling may be via wired, wireless, or a combination of wired and wireless configurations.

The three-dimensional position information relative to the 3D sensor 502 is mapped in software to a graphical representation of the injection site on the user interface/display device 140. This mapping is performed by determining accurate three-dimensional coordinates corresponding to the position of the injection apparatus 105 in the world. The position of the 3D sensor 502 relative to the injection apparatus 105 is also determined with a high degree of precision. This precision allows a very accurate mapping of the detected three-dimensional position information of the hollow needle 232 and its tip 233 to be accurately detected by the 3D sensor 502 and accurately mapped in software to recreate the position of the needle 232 and the needle tip 233 of the testing tool 110. This information is then used to determine both the accuracy of the injection relative to a predetermined injection site accuracy goal, as well as to provide a graphical illustration of the injection, again relative to the injection site goal. This mapping and display can be provided substantially in real time so that a user can adjust the trajectory of injection during the training.

Figure 6A:
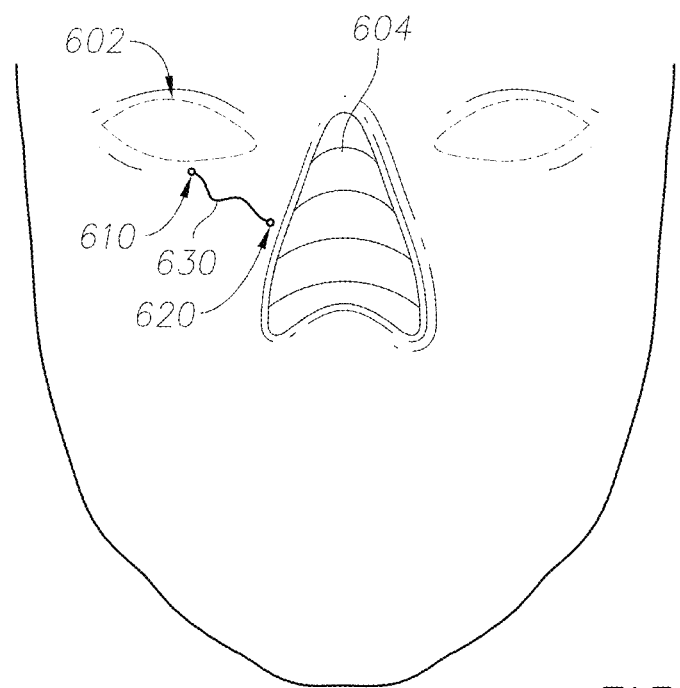
FIGS. 6A and 6B are two perspective views of an example trajectory for an injection.
Figure 6B:
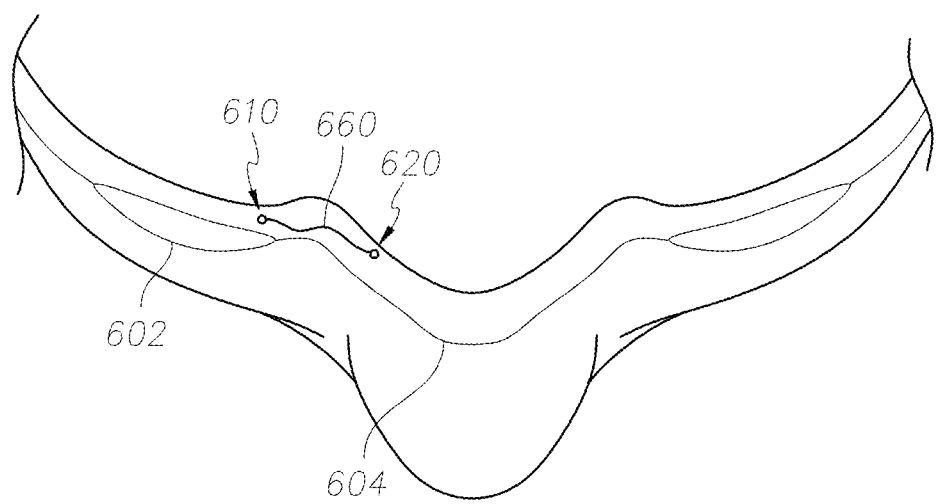

FIGS. 6A and 6B illustrate two views of a trajectory for an injection. FIG. 6A illustrates a view from the perspective of the 3D sensor 502, positioned inside the injection apparatus 105 and directed at the inner surface of the injection apparatus 105. To orient the reader, an eye 602 and a nose 604 have been labeled. An injection starting point 610 is detected by the 3D sensor 502. As the needle tip 233 proceeds into the injection apparatus 105, the changing positions of the light emitted from the needle tip 233 are measured by the 3D sensor 502. In some implementations, the measurement may be a video capture of the injection. In some implementations, the measurement may be a sampled capture at, for example, predetermined intervals. A trajectory path 630, from the starting point 610 to an ending point 620, is thus obtained. As shown in FIG. 6A, the trajectory path 630 takes the form of an irregular injection path, which may, in some circumstances, indicate the need for additional training.

The trajectory path 630 may be presented via the user interface/display device 140. The presentation may include providing a line tracking the injection path. The presentation may include providing an animated depiction of the injection. In some implementations, the presentation may be augmented with additional information such as identifying and showing which muscles, skin, body parts, etc. the injection is coming in contact with or is penetrating. The augmentation of the presentation may retrieve one or more models of the desired physiological information from a data store. The models include three-dimensional information indicating the location(s) of certain anatomical or physiological features. The feature information, along with the three-dimensional injection location information, is mapped onto the presentation of the injection apparatus 105.

Because three-dimensions of information are being obtained, multiple views of the injection trajectory may be provided. FIG. 6B provides a second view of the injection trajectory shown in FIG. 6A. FIG. 6B illustrates a view taken from an overhead perspective of a horizontal cross-section of the injection apparatus 105. The cross-section is taken at a point on the injection apparatus 105 which allows the viewer to see a horizontal injection trajectory path 660 of the needle. As in FIG. 6A, to orient the reader, the eye 602 and the nose 604 have been labeled.

The horizontal injection trajectory path 660 begins at the starting point 610 and ends at the ending point 620. However, because the perspective has changed, the shape of the path 660 is different than that shown in FIG. 6A. This provides another view of the injection result. It will be understood that the presentation model may be arbitrarily rotated, and a representation of the trajectory path for the representational model, as rotated, may be generated. The rotation may be provided to the system as a display point of view identifying the location in space from which to view the trajectory path. Because the injection apparatus digital model is combined with the three-dimensional injection information and, in some instances, anatomical or physiological information, the injection training may provide a wide variety of views, depending on the technique needed for the injection. The views may be provided as animated depictions, such as video or reconstructed animations. For example, in some embodiments, historical trajectories for the same type of injection can be shown in a 3D overlap view which illustrates historical injection trajectories to a current injection trajectory. In this way, a care provider can visually compare trajectory information for improvement progression analysis and general accuracy analysis. Different historical trajectories can be shown in different colors, shades, and/or highlights in order to illustrate age and/or accuracy of the trajectories.

The aspects shown in FIG. 5 allow a trainee to adjust his or her technique and monitor his or her progress toward the ideal injection technique. For example, the user interface/display device 140 may provide a view selector (not shown) to allow the trainee to see the injection site from a variety of views, such as rotated, zoomed in, zoomed out, cross-sectional, time-lapsed, and the like, both in real time and after the injection has occurred. As shown in FIG. 5, a cross-sectional view is displayed on the user interface/display device 140 whereby the trainee can see how far through an opaque skin layer 590 into a clear material layer 592 the testing tool has passed.

In some implementations, the three-dimensional position information received from the 3D sensor 502 may be converted before integration into the digital model of the injection apparatus 105. In such implementations, the received three-dimensional position information may be calibrated, adjusted, or otherwise converted such that the position information of the testing tool 110 may be correlated with a position on the digital model of the injection apparatus 105.

Figure 7:
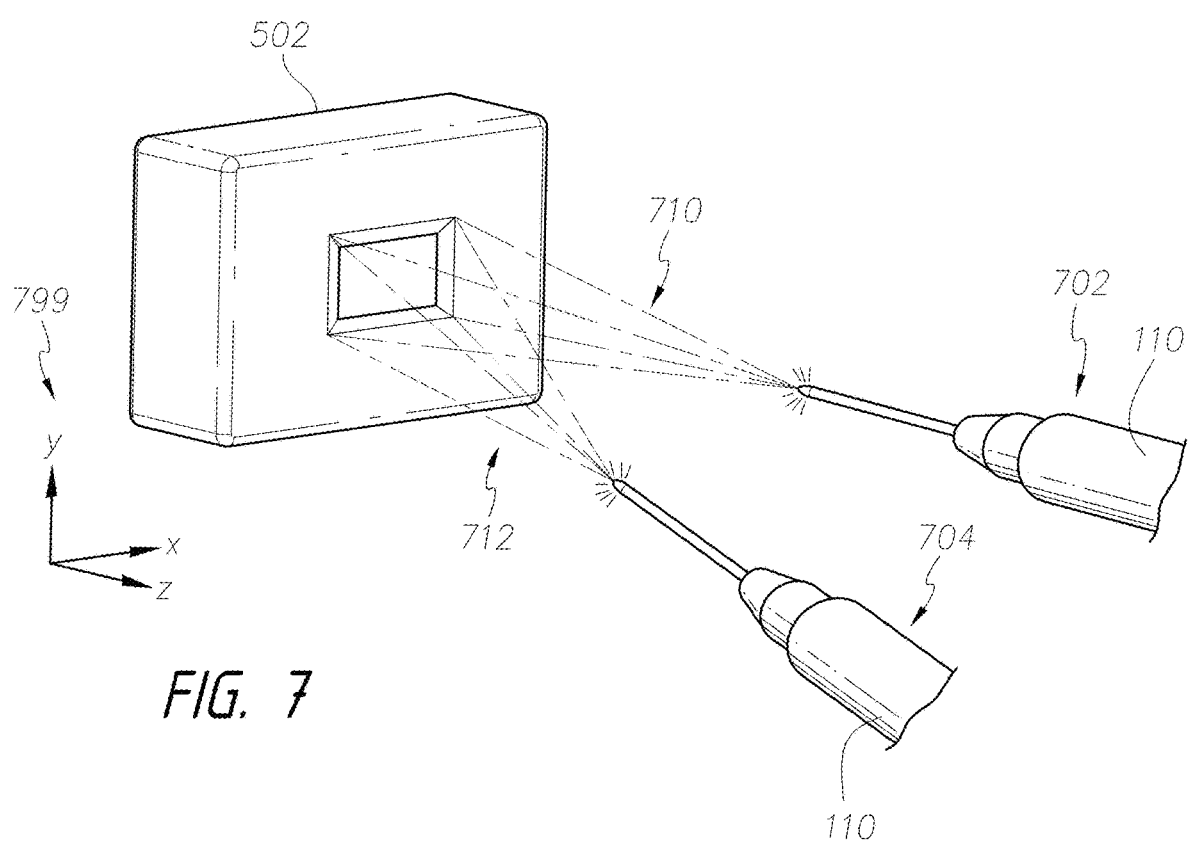
FIG. 7 illustrates an example embodiment of a three-dimensional (3D) injection detection sensor.

As discussed, one or more sensors may be provided within the training apparatus 105 which provide three-dimensional position information for the testing tool 110. FIG. 7 illustrates an example embodiment of a 3D sensor 502. A dimensional legend 799 is provided to indicate the three axes (e.g., X, Y and Z) of detection. This dimensional legend 799 is logical and may not physically be included in an embodiment of the injection training systems described. The names attributed to each axis may differ, but each axis should represent one unique dimension.

The 3D sensor 502 is shown receiving light from a testing tool 110 at a first position 702, and then at a second position 704. These positions are not simultaneous, but rather represent the sequential movement of the testing tool 110 over time. The light emitted from the testing tool 110 is received by the 3D sensor 502. The light is emitted from the tip 233 of the testing tool 110 and disperses on its way to the 3D sensor 502. As shown in FIG. 7, a first area of light 710 is generated when the testing tool is located at the first position 702. A second area of light 712 is generated at a second time when the testing tool 110 is located at the second position 704. The 3D sensor 502 may be configured to measure one or more characteristics of the received light and generate information corresponding to the three-dimensional position of the testing tool 110 based on the characteristics detected. Illustratively, the characteristics may include angle, intensity, brightness, color, dispersion, and/or duration of the light.

In one implementation, the 3D sensor 502 may include an array of light sensors. As light is emitted from the needle tip 233, one or more of the sensors in the array may receive light. By aggregating the information about which sensors received light and characteristics of the light received at each sensor, three-dimensional information about the position of the light source may be determined. Some 3D sensors 502 may be housed in a recess and, based on the light pattern cast on the sensor, determine the location of the light source. In generating the 3D location information, the 3D sensor 502 may also obtain calibration information for the needle tip 233 of the testing tool 110 to account for variability, such as in manufacturing, wear-and-tear, and power. Further calibration information may be used to specify the field of view 504 for the 3D sensor 502. The calibration information may be received, for example, through an initialization sequence whereby the testing tool 110 is placed at a predetermined location on the injection apparatus.

Because the 3D sensor 502 knows the light source and its particular location vis-à-vis the light source, the 3D sensor 502 can generate accurate and, in some implementations, real-time 3D location information for the testing tool 110.

Figure 8:
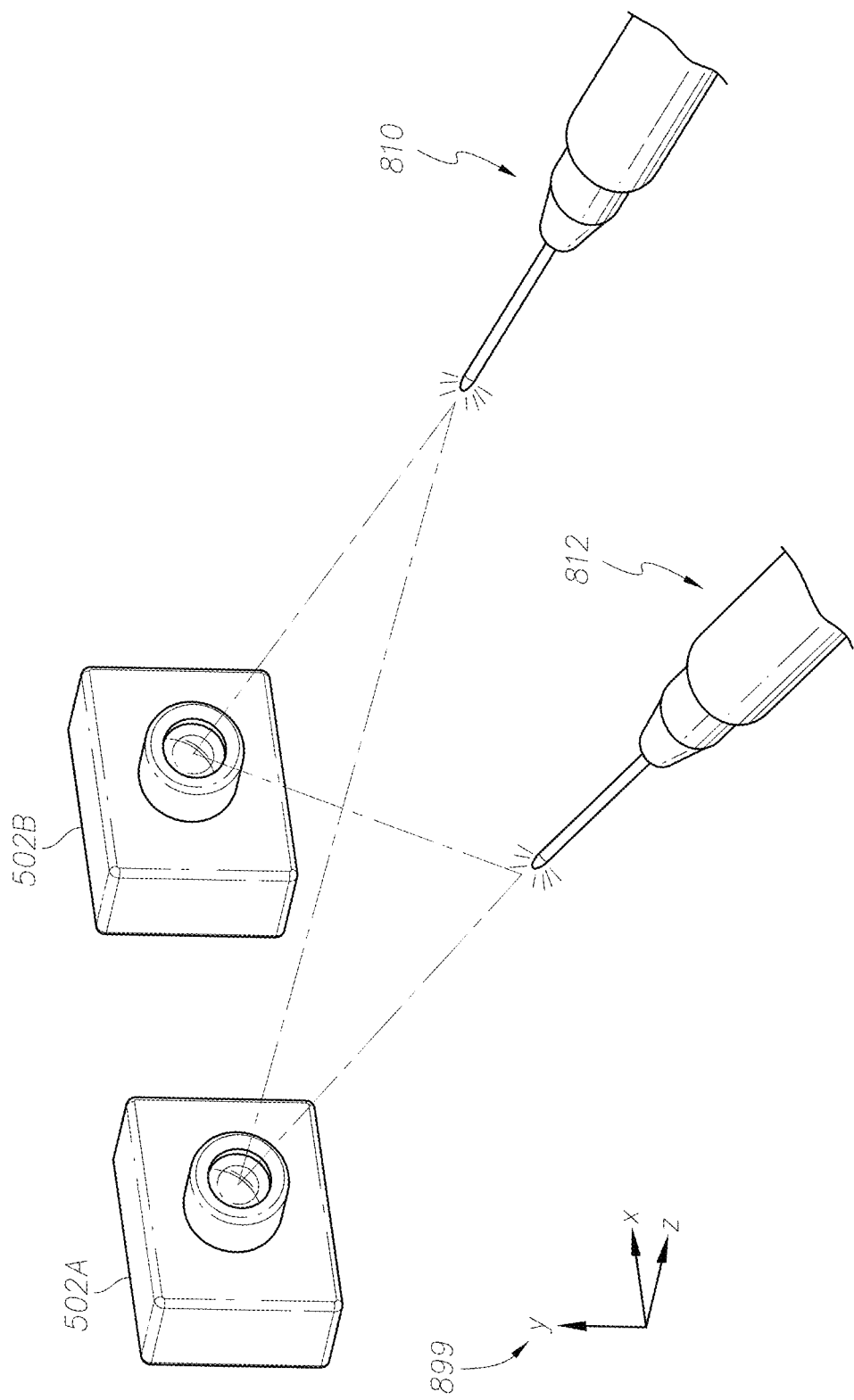
FIG. 8 illustrates an example embodiment of a 3D injection detection sensor.

FIG. 8 illustrates another embodiment of a 3D sensor 502. It may be desirable to implement the 3D sensor 502 as a stereoscopic sensor pair. A dimensional legend 899 is provided indicate the three axes (e.g., X, Y and Z) of detection. This dimensional legend 899 is logical and may not physically be included in an embodiment of the injection training systems described. The names attributed to each axis may differ, but each axis should represent one unique dimension.

The 3D sensor pair includes a first 3D sensor 502A and a second 3D sensor 502B. The first 3D sensor 502A and the second 3D sensor 502B are configured to receive, at substantially the same time, light from a testing tool 110. The testing tool 110 may be located at different positions at different times. FIG. 8 shows a first position 810 at a first time, and a second position 812 at a second time, for the testing tool 110.

Each 3D sensor 502A and 502B is configured to measure one or more characteristics of the light transmitted from the testing tool's 110 position and to generate three-dimensional location information corresponding to the position of the testing tool 110, based in the detected characteristics. The characteristics may include angle, intensity, dispersion, brightness, color, or duration of the sensed light. Combining the characteristic data received from the first 3D sensor 502A and the second 3D sensor 502B, three-dimensional information for the testing tool 110 may be generated. The combination may be performed by one of the 3D sensors 502A and 502B, or by the signal processing and display interface 555. In an embodiment the combination can be performed in the user interface/display device 140.

In generating the 3D location information, the generation of the three-dimensional information may also include obtaining calibration information for the needle tip 233 to account for variability such as in manufacturing, wear-and-tear, and power. The calibration information may be received, for example, through an initialization sequence whereby the testing tool 110 is placed at a predetermined location on the injection apparatus 105.

Figure 9:
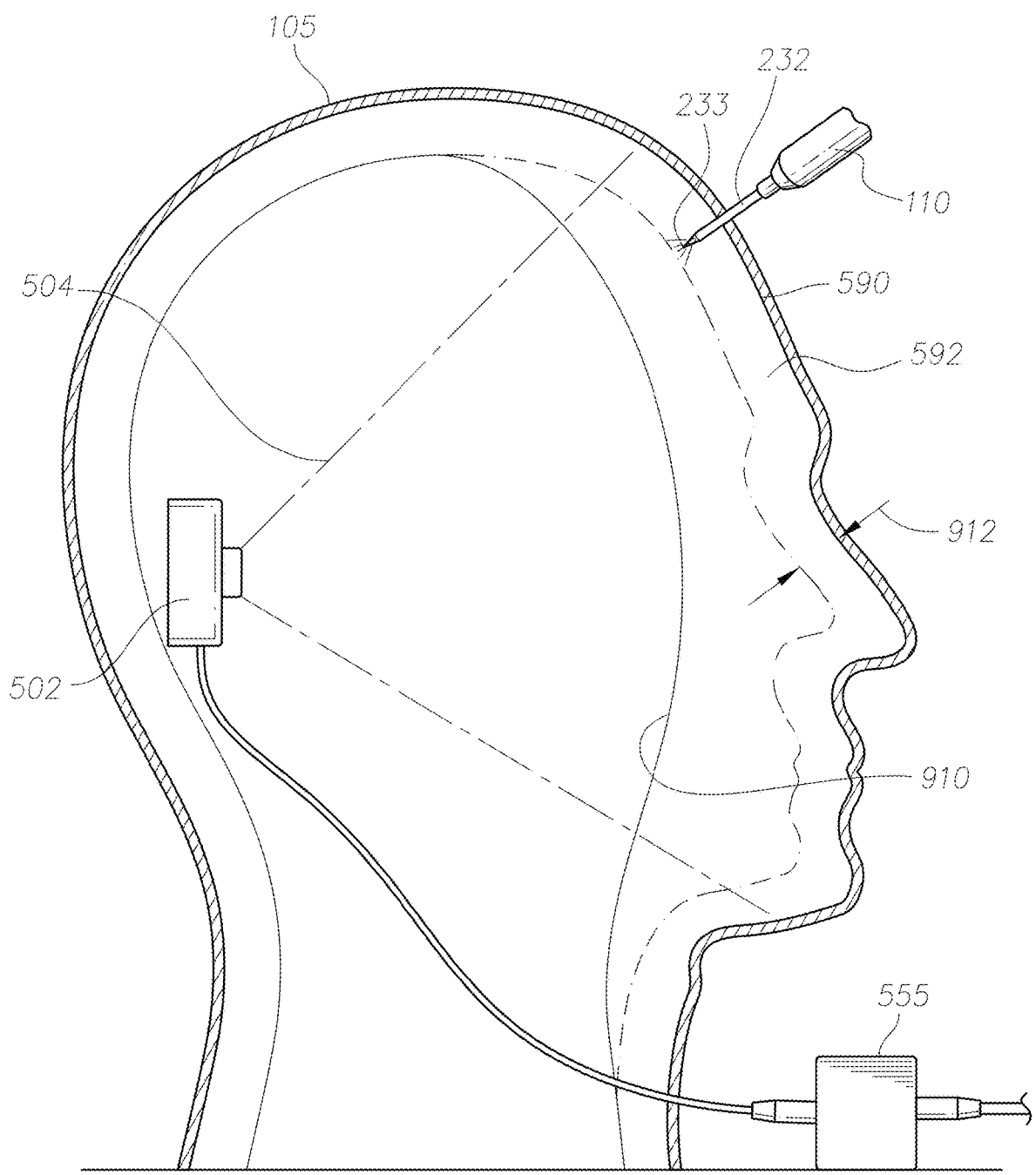
FIG. 9 illustrates a side view of one embodiment of the injection apparatus including a 3D injection detection sensor.

FIG. 9 depicts a side view of one embodiment of the injection apparatus 105, including a 3D sensor 502. The injection apparatus 105 is formed as a human head. A testing tool 110 is shown inserted into the injection apparatus 105. The testing tool 110 may be implemented as described above, such as in reference to FIGS. 2A-G, 3A-C and 4A-C. To minimize diffraction of the light emitted from the testing tool 110, a surface of clear elastomer 910 may be made substantially perpendicular to the direction of light travel. Accordingly, in an embodiment the inner surface of the clear elastomer 910 is formed as a spherical surface with the center facing a 3D sensor 502. The 3D sensor 502 may be implemented as described above such as in reference to FIGS. 5, 7 and 8. The 3D sensor 502 is configured to detect light emitted by the testing tool 110 within a field of view 504.

Rather than utilize a light emitting testing tool 110 in combination with a single two-dimensional (2D) camera that detects a two-dimensional position of the light emitting needle tip 233, the injection training system 100 may include one or more 3D sensors 502 and/or tracking equipment. With a single 2D camera, a position with respect to a third dimension may be determined, for example, by tinting the clear elastomer surface 910, causing a color of the light to change as the needle tip 233 transitions through the tinted layer. Illustratively, the color may trend toward white light as the needle tip 233 moves closer to the inner surface of the clear elastomer surface 910.

It may be desirable to avoid tinting the clear elastomer surface 910 and allow the use of 3D tracking equipment, such as 3D sensors 502 (which may be cameras or other types of sensors), examples of which are shown in FIGS. 7 and 8 above. Further examples of 3D tracking equipment include equipment sold by Personal Space Technologies B.V. (available at http://ps-tech.com/). An additional example of 3D tracking equipment is described in a Centre Suisse d'Electronique et Microtechnique SA (CSEM) Scientific & Technical Report entitled "spaceCoder: a Nanometric 3D Position Sensing Device," which is incorporated by reference herein in its entirety.

As the testing tool 110 penetrates an opaque skin layer 590 and enters the internal clear elastomer layer 592, the 3D sensor 502 detects characteristics of the light which can be used to generate a three-dimensional location of the testing tool 110. For example, it may be desirable to track a desired range 912 of needle penetration. In some implementations, the depth information is displayed on a display, such as the user interface/display device 140, as the testing tool 110 is inserted. This allows a trainee to visualize the location of the injection in near real-time. The signal processing and display interface 555 may provide the location information to facilitate such displays. In some implementations, the feedback may be provided in audio form such as a beep or an alert.

Figure 10:
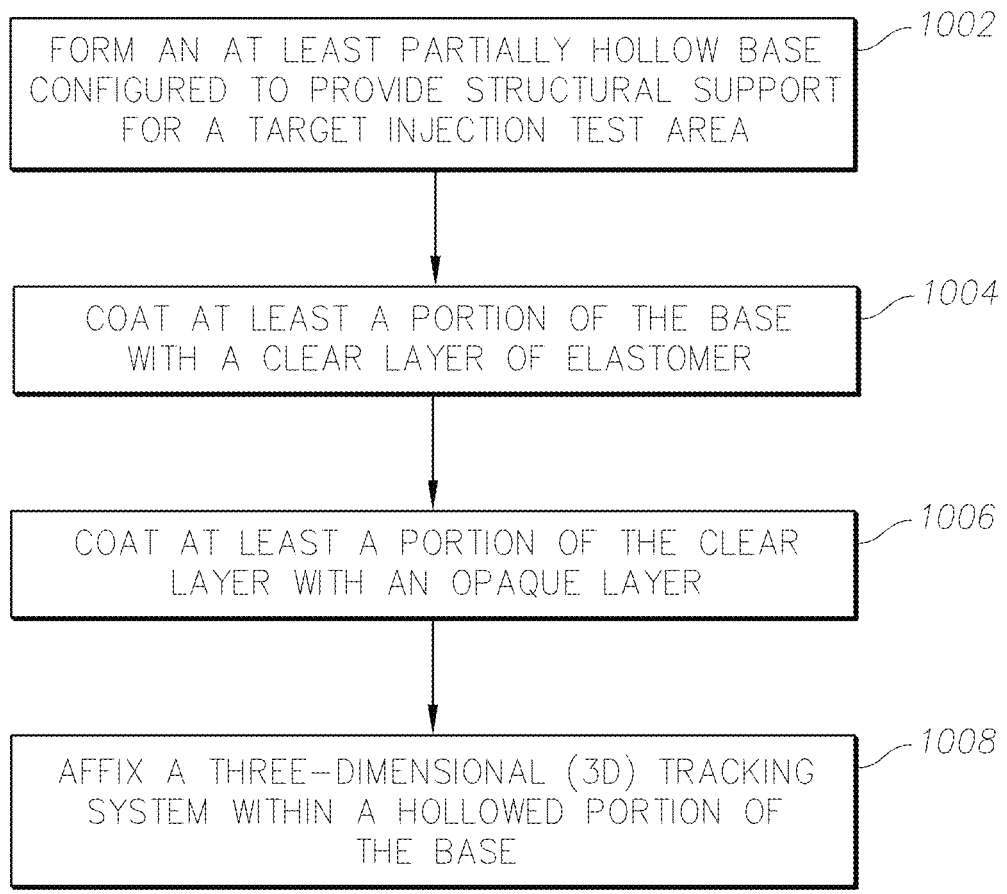
FIG. 10 is a process flow diagram of a method of manufacturing an anatomically shaped injection apparatus including a 3D tracking system.

FIG. 10 shows a process flow diagram of a method of manufacturing an anatomically shaped injection apparatus 105 including a 3D sensor 502, such as that shown in FIG. 9. The method includes, at block 1002, forming an at least partially hollow base configured to provide structural support for a target injection test area. The method includes, at block 1004, coating at least a portion of the base with a clear layer of elastomer. The method also includes, at block 1006, coating at least a portion of the clear layer with an opaque layer. The base, clear layer, and opaque layer form an anatomical shape such as a skull. The method further includes, at block 1008, affixing a three-dimensional (3D) tracking system (which can include one or more 3D sensors 502) within the hollowed portion of the base, wherein the three-dimensional tracking system provides a field of view of the clear layer covering the target injection test area. The three-dimensional tracking system may be a 3D camera such as that shown in FIG. 7 or a stereoscopic camera pair such as those shown in FIG. 8. In some implementations, the method may also include coupling the 3D tracking system with a location processor configured to provide location information for a light source inserted into the clear layer. The location information identifies a three-dimensional location of the light source relative to the injection apparatus 105. The location processor may be implemented in the signal processing and display interface 555 shown in FIG. 5.

Figure 11:
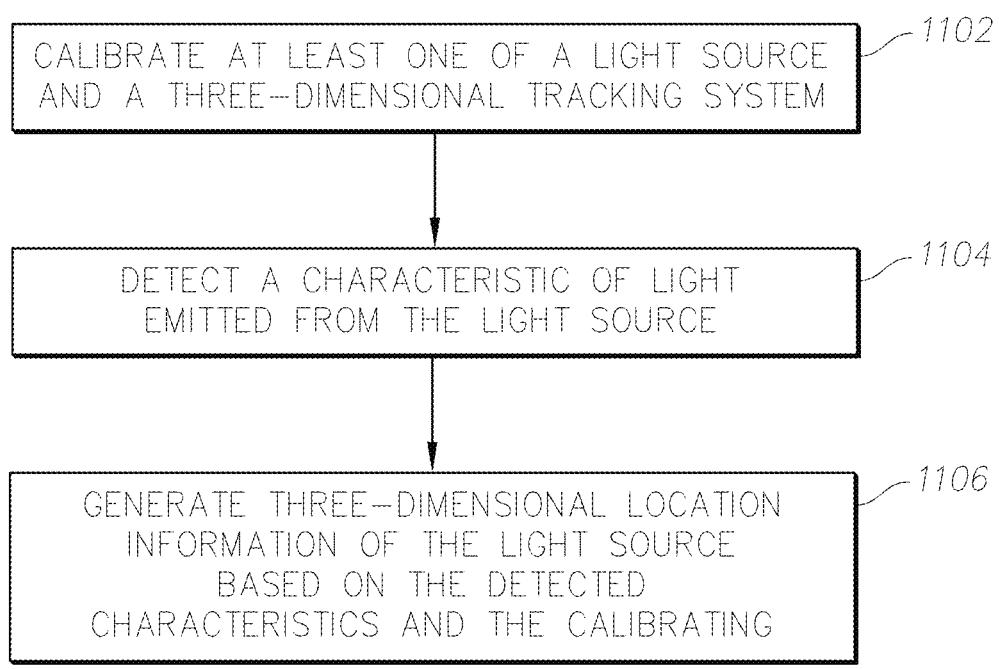
FIG. 11 is a process flow diagram for a method of 3D injection training.

FIG. 11 illustrates a process flow diagram for a method of three-dimensional (3D) injection training. The method may be performed in whole or in part by one or more of the devices described herein such as the training apparatuses described above.

The method includes, at block 1102, calibrating at least one of a light source and a three-dimensional tracking system. The light source may be a light emitter located at the tip 233 of a testing tool 110. The three-dimensional tracking system may include a 3D camera, a stereoscopic camera pair, or other sensor configured to provide three-dimensional location information for the light source. The method also includes, at block 1104, detecting, by the three-dimensional tracking system, a characteristic of light emitted from the light source for an injection. The characteristic may include intensity, angle, dispersion, brightness, color, or duration of the light. In some implementations, an array of sensors may be used to detect light. In such implementations, the characteristic may include which sensors in the array of sensors received light. The method further includes, at block 1106, generating three-dimensional location information of the light source based on the detected characteristics and said calibrating.

In some embodiments, the testing tool 110 is configured to determine its position and orientation in three-dimensional space relative to the injection apparatus 105. The testing tool 110 is also configured to communicate its position and orientation information to other components of the injection training system 100, such as, for example, the user interface/display device 140. The user interface/display device 140 can display, in near real time, the testing tool's 110 position relative to the injection apparatus 105, as injection training is performed. The testing tool 110 can also communicate its position and orientation information to the 3D sensor 502 and/or to the signal processing and display interface 555.

In an embodiment, the position sensor 308 collects nine dimensions of sensed information to determine the 3D position and orientation of the testing tool 110 in space with adequate accuracy. This is because processing sensed three-dimensional angular velocity provided by a 3D gyroscope leads to an accumulating error in the calculated position and orientation of the testing tool 110. To compensate for this error accumulation, measurements from a 3D accelerometer and from a 3D magnetometer can be used. The 3D accelerometer measures the earth's gravitational field, and the 3D magnetometer measures the earth's magnetic field. Together, the sensed information from the 3D accelerometer and 3D magnetometer can provide an absolute reference of orientation that can be used to compensate for the progressively accumulating error of the sensed and processed angular velocity data provided by the 3D gyroscope. A method for sensor fusion includes processing the measured nine dimensions of sensed information (from the 3D gyroscope, the 3D accelerometer, and the 3D magnetometer) to determine a single estimate of position and orientation of the testing tool 110, in three-dimensional world coordinates.

In an embodiment, the position sensor 308 of the testing tool 110 comprises a inertial measurement unit (IMU) that includes one or more accelerometers, one or more gyroscopes, one or more magnetometers to provide, in near real time, information describing the 3D position and orientation of the testing tool 110. In some embodiments, the position sensor 308 can also include an embedded processor that handles, among other things, signal sampling, buffering, sensor calibration, and sensor fusion processing of the sensed inertial data. The position sensor 308 can also include a wireless network protocol for data transmission to external components, such as, for example, the user interface/display device 140, the 3D sensor 502, and the signal processing and display interface 555. Illustratively, the position sensor 308 senses, processes and transmits sensed position and orientation data of the testing tool 110 to a sensor fusion processing component that can be configured to operate on, for example, the user interface/display device 140. In an embodiment, the position sensor 308 transmits already-processed position and orientation information, delivered in three-dimensional, world coordinates, to the user interface/display device 140 which graphically displays the position of the testing tool 110 relative to the injection apparatus 105 in near real time as the injecting training occurs. The position sensor 308 can provide calibrated 3D linear acceleration, 3D angular velocity, 3D magnetic field, and optionally, atmospheric pressure data, to the sensor fusion processing component which processes the data to deliver precise position and orientation information of the testing tool 110. In an embodiment, the sensor fusion processing component employs a Kalman filter to provide three degrees-of-freedom position and orientation information of the testing tool 110 relative to the injection apparatus 105. The sensor fusion processing component uses data collected from the gyroscopes, accelerometers and magnetometers to compute a statistical, optimal 3D position and orientation estimate, of high accuracy and with no drift, for movements of the testing tool 110.

Illustratively, the sensor fusion processing component comprises an algorithm in which the measurement of gravity (by the 3D accelerometers) and the earth's magnetic north (by the 3D magnetometers) compensate for otherwise slowly, but steadily increasing drift errors from the processing (using mathematical integration) of rate-of-turn data (angular velocity) measured from the rate gyroscopes. The described approach for compensating for drift can be referred to as attitude and heading referenced, and a system that employs this approach can be referred to as an Attitude and Heading Reference System (AHRS).

Figure 12:
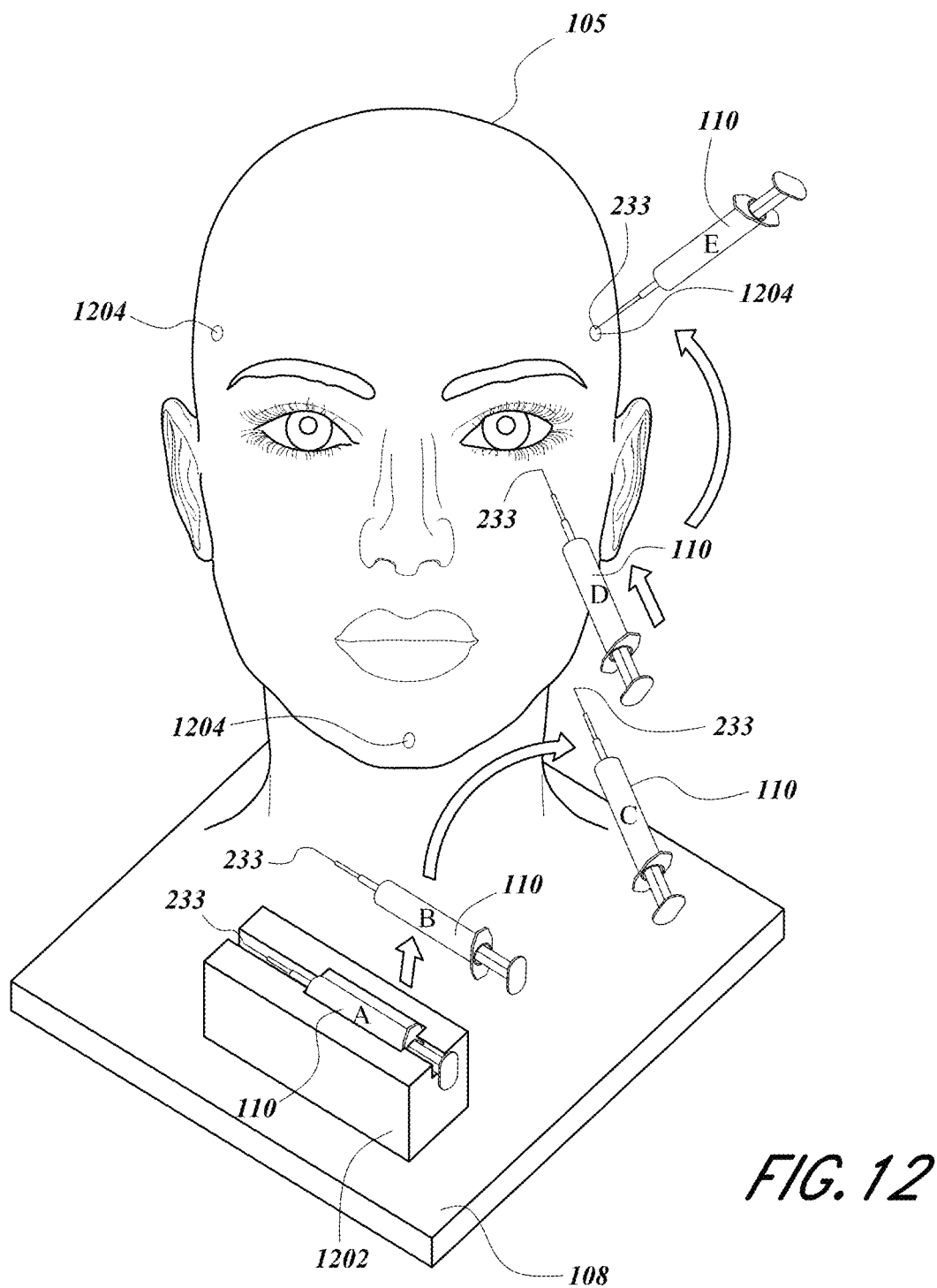
FIG. 12 illustrates an embodiment of an injection training system comprising an injection apparatus, a testing tool, and a resting cradle in which the testing tool follows a sequence of motion (A through D) from the resting cradle to an injection site of the injection apparatus.

FIG. 12 illustrates an embodiment of an injection training system 100 comprising an injection apparatus 105, a testing tool 110, and a resting cradle 1202 in which the testing tool 110 follows a sequence of motion (A through D) from the resting cradle 1202 to an injection site of the injection apparatus 105. In FIG. 12, the injector's hand is not shown to better illustrate the motion of the testing tool 110. At position A, the testing tool 110 sits in the resting cradle 1202. The resting cradle 1202 is in a known, fixed position relative to the injection apparatus 105. This can serve to calibrate the injection training system 100 to know where the testing tool 110 is located relative to the injection apparatus 105 at the initiation of the injection training. In an embodiment, the resting cradle 1202 is attached to the base 108 of the injection apparatus 105. In an embodiment, the injection apparatus 105 has calibration points 1204 that can be used to establish an initial position of the testing tool 110 relative to the injection apparatus 105.

Starting from the known position relative to the injection apparatus 105, such as from the resting cradle 1202, the movement of the testing tool 110 can be determined, even as the needle tip 233 penetrates the material of the artificial face. By way of non-limiting illustration, the testing tool is lifted from the resting cradle 1202 to position B. The testing tool 110 is rotated to position C, where the needle tip 233 is directed toward the injection apparatus 105. At position D, the needle tip 233 of the testing tool 110 is inserted into the injection apparatus 105. Position information corresponding to the testing tool 110, including the needle tip 233, can be conveyed to a digital model of the injection apparatus 105. The digital model includes target tissue (individual muscles) and details of vital structures (VS, which is also referred to as vital tissue, VT), such as, for example, arteries, veins, nerves, and skeletal portions, that are to be avoided or accommodated. By comparing the position of the needle tip 233, based on the determined position of the testing tool 110, to the target tissues and the vital structures illustrated on the user interface/display device 140, proximity to a desired injection target can be established. This proximity to target and to vital structures can serve as the basis for evaluating the skill of the injection trainee.

Various manufacturers offer for sale inertial measurement systems, devices, and methods, including sensor fusion processing components, for incorporation into products and systems. Such manufacturers include Xsens Technologies, B.V., of Enschede, the Netherlands; InvenSense, Inc. of Sunnyvale, Calif., USA; and Synopsys, Inc., of Mountain View, Calif., USA. Examples of systems, devices and/or methods for inertial measurement of objects in three-dimensional space are disclosed in U.S. Pat. No. 7,725,279B2, issued on May 25, 2010; U.S. Pat. No. 8,165,844B2, issued on Apr. 24, 2012; U.S. Pat. No. 8,203,487B2; issued on Jun. 19, 2012; U.S. Pat. No. 8,250,921B2, issued on Aug. 28, 2012; U.S. Pat. No. 8,351,773B2, issued on Jan. 8, 2013; and in U.S. Patent Application Publication Numbers 2009/0278791A1, published on Nov. 12, 2009; and 2009/0265671A1, published on Oct. 22, 2009, each of which is incorporated by reference herein in its entirety.

Computation of the position and orientation of an object in three-dimensional space is a task that can process inputs from several sensors to achieve accurate estimates of the position and orientation of the object. The method can be referred to generally as a fusion of sensor inputs. A sensor fusion process can reduce the impact of, and/or compensate for, inaccuracies of sensor measurements and/or processing approximations. Disclosed herein is a system and method to implement a fusion process that is computationally efficient and that includes nine dimensions of sensor input. In an embodiment, the system includes a processor that can be supplemented with hardware accelerators to help reduce power consumption. An example of a system, device and method to compute the 3D orientation of an object by processing nine dimensions of data using a sensor fusion process is described in a paper entitled "Ultra Low-Power 9D Fusion Implementation: A Case Study," by Pieter Struik, which is incorporated by reference herein in its entirety.

The disclosed system and method to fuse sensor information is one among many possible sensor fusion approaches. One skilled in the art will appreciate that there are numerous systems and methods for fusing sensor input to derive accurate position and orientation information of an object in three-dimensional space without departing from the spirit of the present disclosure. The disclosed system and method offers effective tracking performance while executing computations that are similar to those used by other sensor fusion processes. Performance optimization for this embodiment is based on an analysis of processing-intensive activities. One approach to optimization is to employ a fixed point processing implementation. Another approach to optimization can include the use of one or more hardware accelerators to execute certain computations efficiently. Such optimization approaches are directed at reducing the number of processing cycles required to determine accurate estimates of the position and orientation of an object in three-dimensional space.

Described herein is a system and method to calculate three-dimensional (3D) position and orientation of an object derived from inputs from three motion sensors attached to the object: an accelerometer configured to measure linear acceleration along three axes; a gyroscope configured to measure angular velocity around three axes; and a magnetometer configured to measure the strength of a magnetic field (such as the earth's magnetic field) along three axes. In an embodiment, the three motion sensors are attached to the testing tool 110. In an embodiment the three motion sensors are integrated into a single position sensor 308, as reflected in FIG. 3A. In an embodiment, the sensors are sampled at a rate of 50 Hz; however, one skilled in the art will appreciate that the sensors can be sampled at different rates without deviating from the scope of the present disclosure. The sampled data from the three motion sensors, which provide nine sensor inputs, are processed to describe the testing tool's 110 position and orientation in three-dimensional space. The testing tool's position and orientation are described in terms of Euler angles as a set of rotations around a set of X-Y-Z axes of the testing tool 110.

Theoretically, the method to determine orientation angles around the three axes of the testing tool 110 is a straightforward process that includes mathematically integrating the three angular velocity measurements provided by the 3D gyroscope sensor. However, when implemented, sensor drift and/or processing approximations can lead to a steadily increasing set of errors that affect the accuracy of such determinations. A method to compensate for the inaccuracy of the processed angular velocity measurements includes processing accelerometer data and magnetometer (or compass) data, in a sensor fusion process. The disclosed system and method to fuse sensor input applies principles that are comparable in accuracy to systems and methods that employ techniques of linear quadratic estimation, such as Kalman filtering, which may also be used to fuse sensor input data in some embodiments.

The disclosed system and method to fuse sensor input uses quaternion algebra to determine a present position and orientation of the testing tool 110. In practical application, quaternions can be used in conjunction with other processing methods, such as Euler angles and rotation matrices, to calculate rotations of objects in three-dimensional space. Illustratively, a quaternion, where Q=[q0 q1 q2 q3], can define a three-by-three rotation matrix "R" that translates each coordinate x=(x,y,z) of the initial testing tool's 110 orientation into its current position, Rx. A product (known as the Hamilton product in quaternion algebra, which is represented by the symbol "⊗") of two quaternions, such as Q0⊗Q1, delivers another quaternion that describes a compound rotation performed by a first rotation, described by Q0, which is followed by a second rotation, described by Q1. Use of quaternion algebra can reduce computational processing requirements because most of the computations used to perform quaternion algebra do not employ computationally-intensive trigonometric functions.

Figure 13A:
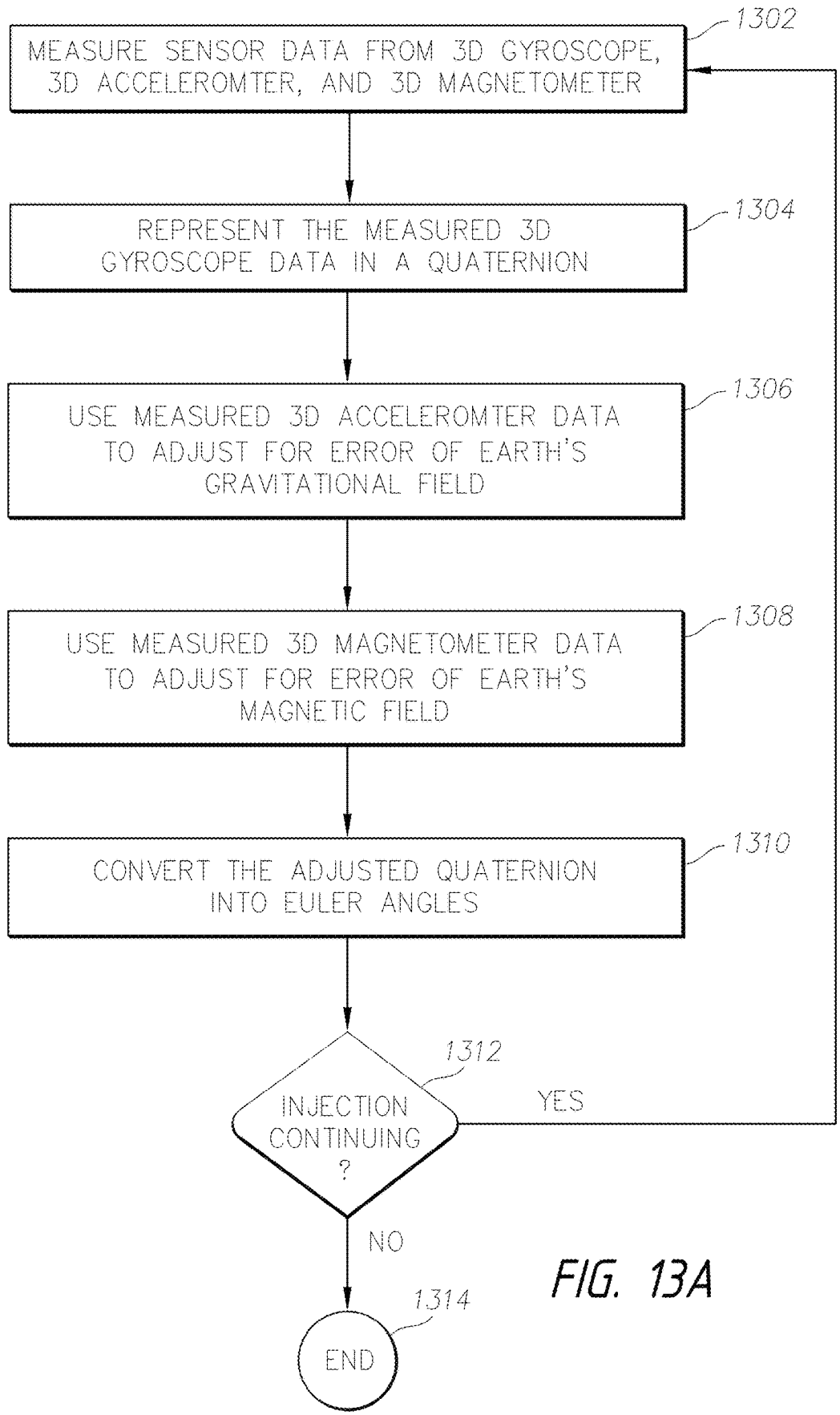
FIG. 13A illustrates a process flow diagram of a process to determine the position and orientation of a testing tool according to an embodiment of the disclosed injection training system.

FIG. 13A illustrates a process flow diagram of a process 1300 to determine the position and orientation of a testing tool 110 according to an embodiment of the disclosed injection training system 100. One skilled in the art will appreciate that there are numerous ways by which the position and orientation of the testing tool 110 can be determined without departing from the scope of the present disclosure. At block 1302, the process begins by collecting measured data from the 3D gyroscope, the 3D accelerometer, and the 3D magnetometer. The sampling rate can vary, depending on the components used to implement the process.

At block 1304, the present orientation of the testing tool 110 is represented by a quaternion "Q" which represents the currently measured angular acceleration data from the 3D gyroscope. This quaternion is an initial estimate of the position and orientation of the testing tool 110. The present orientation can be updated with information provided by the gyroscope sensor which may be represented as (gx, gy, gz). Additional rotation of the testing tool 110 that occurred since the most recent measurement can be represented by a quaternion [1 (gx/f) (gy/f) (gz/f)], where f is defined as a sampling frequency used to execute the sensor fusion process. This representation may be expressed as quaternion [C gx gy gz], with "C" being a constant that is proportional to the sampling frequency, f.

At block 1306, information provided by an accelerometer sensor is used to help compensate for accuracy errors in the angular velocity data provided by the gyroscope sensor. An acceleration vector (ax, ay, az), measured by the accelerometer, will equal the acceleration of gravity when the testing tool 110 is not in motion. When the testing tool 110 is in motion, its rotation can be characterized by rotation R, and the vector corresponding to gravity is directed towards the earth's center. When viewed relative to the motion of the sensors attached to the testing tool 110, the gravity vector will have been rotated by the same rotation R. Accordingly, the initial gravity vector v becomes Rv, relative to the testing tool 110, after rotation has taken place. If the testing tool 110 is not moving, the computed gravity vector, Rv, will be aligned with the measured accelerometer information (ax, ay, az). When Rv and (ax, ay, az) are pointing in different directions, we determine that rotation R is inaccurate and, therefore, the coordinates representing the present orientation, Q, must be adjusted based on the vector cross product Rv×(ax, ay, az).

At block 1308, fusion with information sensed by the magnetometer can also be applied. It is assumed that the testing tool 110 is subject to the earth's magnetic field. It is also assumed that the testing tool 110 is not subject to interference from a separate magnetic field, such as, for example, the field of a permanent magnet. Under these assumed conditions, the magnetic field measured by the 3D magnetometer (mx, my, mz) can be related to the initial orientation of the testing tool 110 by applying a reverse rotation R*, where the vector w=R*(mx, my, mz). It is also assumed that the earth's magnetic north is aligned in the direction of the X axis. Accordingly, an alignment error can be determined by comparing the vector w to a vector w', which is obtained by rotating the vector w onto the plane of the testing tool 110. An alignment error vector c can be calculated. The alignment error vector, c, is proportional to the vector cross product c=w×w'. As c is related to the initial orientation of the testing tool 110, Rc corresponds to the adjustment that can be applied to the testing tool's 110 present position and orientation, represented by quaternion Q.

At block 1310, the adjusted quaternion Q is converted into three Euler angles. Euler angles are a way of representing the spatial orientation of a coordinate system as a composition of three elemental rotations, starting from a known, standard orientation. The relation between the quaternion Q and the converted Euler angles includes calculations that use inverse sine and inverse tangent functions. Illustratively, the rotation angle around the Y axis is determined with the following conversion equation: $Y = -a\sin(2*q1*q3 + 2*q0*q2)$, where the quaternion $Q=[q0\ q1\ q2\ q3]$.

In an embodiment, the method 1300 to determine the position and orientation of a testing tool 110 updates the position and orientation of the testing tool 110 at the sampling rate of the sensors. Accordingly, at block 1312, the process 1300 determines whether the present injection training is continuing or whether it has ended. When the present injection training is continuing, the method 1300 returns to block 1302 to update the position and orientation information of the testing tool 110. When the present injection training is completed, the process 1300 terminates at block 1314.

Figures 13B, 13B1, 13B2:
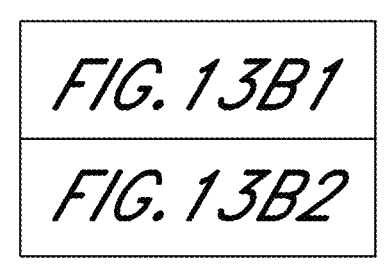

FIGS. 13B, 13B1, and 1362, collectively, illustrates a process flow diagram of a process 1340 to determine the position and orientation of a testing tool 110 according to an embodiment of the disclosed injection training system 100. Illustratively, process 1340 discloses one approach to implementing process 1300, described above. One skilled in the art will appreciate that there are numerous ways by which process 1300 can be implemented without departing from the scope of the present disclosure.

At block 1350, the process begins by collecting measured data from the 3D gyroscope (providing angular momentum information), the 3D accelerometer (providing linear accelerations information), and the 3D magnetometer (providing magnetic field information). The present position and orientation of the testing tool 110 is represented by a quaternion, based on the measured angular acceleration data from the 3D gyroscope. Blocks 1352 through 1358 illustrate computation actions implemented to compensate for inaccuracies in the angular velocity data, provided by the 3D gyroscope, based on the linear acceleration information provided by the 3D accelerometer. This methodology uses the earth's gravitational field to identify inaccuracies in the measured angular momentum data and to compensate for those inaccuracies. At block 1352, the measured 3D accelerometer data is compared with a rotated initial gravity vector. At block 1354, the accelerator data is inverted and normalized. At block 1356, a vector cross product of the normalized accelerator data and the rotated gravity vector is computed. And at block 1358, a compensation for gyroscope data inaccuracies is made, using a constant acceleration compensation factor.

Blocks 1360 through 1368 illustrate actions implemented to compensate for inaccuracies in the angular velocity data, provided by the 3D gyroscope, based on the magnetic field information provided by the 3D magnetometer. This methodology uses the earth's magnetic field to identify inaccuracies in the measured angular momentum data and to compensate for those inaccuracies. At block 1360, the measured 3D magnetometer data is normalized and inverted. At block 1362, an inverse rotation of the normalized magnetometer data is computed. At block 1364, the computed rotation is aligned in orientation with the testing tool 110, based on earth's magnetic north. At block 1366, the computed rotation is rotated back to the original orientation, and an alignment error vector is computed by computing a cross product of rotation vector with the measured magnetometer data. At block 1370, a compensation for gyroscope data inaccuracies is made, using a constant magnetic compensation factor. At block 1370, the testing tool's position and orientation, represented in a quaternion, is updated based on the adjusted gyroscope data, and it is normalize at block 1372. At block 1374, the updated position and orientation information of the testing tool 110 is converted into Euler angles which can be used by, for example, the user interface/display device 140 to graphically display the position of the testing tool 110. At block 1376, the process 1340 returns to block 1350, to begin another iteration when the injection training is continuing. Alternatively, the process terminates at block 1378 when the injection training is finished.

Advantageously, the disclosed method for determining the position and orientation of a testing tool 110 is robust, even when assumptions are not held. For example, when the testing tool 110 is moving, the measured accelerometer data (ax, ay, az) represents a non-zero linear acceleration relative to gravity; however the sensor fusion processing method nevertheless delivers accurate position data. Moreover, fusion of magnetometer data proves to be accurate in the presence of distortion in the gravitational magnetic field.

In an embodiment, the disclosed method can be implemented in a system of integrated hardware and software (or firmware) that can be optimized to process data from digital and analog sensors and to engage in power-efficient processing of the sensor data. The system can include a processor (such as the ARC EM4 32-bit processor core offered by Synopsys Inc.), a user-configurable set of serial digital interfaces, analog-to-digital converter interfaces, hardware accelerators, and a software library of digital signal processor (DSP) functions and input/output (I/O) software drivers. The system can take advantage of capabilities to implement tightly coupled I/O peripherals and tightly coupled hardware accelerators, which may be accessed directly from the processor pipeline without the overhead of additional hardware infrastructure, such as, for example, busses, bridges, and/or adapters.

In an embodiment, the system configuration contains one or more Inter-Integrated Circuit (I2C) master peripheral ports, a Serial Peripheral Interface (SPI) master peripheral port, and a general purpose input/output (GPIO) port. The processor can be configured to have a single-cycle 32-bit integer multiplier. The system can be configured to include one or more fixed-point hardware accelerators to perform computationally-intensive operations, such as, for example, multiply-accumulate (MAC) operations, trigonometric operations, and the square root operation. Illustratively, use of hardware accelerators can reduce processor cycle time with respect to computationally-intensive operations such as the square root operation. A hardware accelerator accepts a 32-bit fixed point number as input and computes the square root in 31 cycles, evaluating one bit at a time which is substantially faster than calculating a square root by use of software delivered as part of a compiler's standard library.

Many of the required computations used in the disclosed method are computationally-intensive when implemented using standard software routines. For example, rotation and inverse rotation operations are matrix-vector multiplications where the (inverse) rotation matrix has coefficients that are based on the quaternion Q. Illustratively, inverse rotation operations involve many multiplications and additions. Similarly computing the inverse norm of a vector or a quaternion requires the following operations: multiplication, addition, square root, and division. Likewise, computing a vector cross product requires multiplication operations and addition operations. Computing the Hamilton product of two quaternions takes many multiplications and additions. Computing Euler angles involves trigonometric functions (a tan 2 and a sin), where the arguments are expressions that are based on quaternion Q. These expressions include multiplication operations and addition operations. Use of one or more hardware accelerators to implement such operations can reduce overall processing time and power consumption.

To further improve performance and to reduce power consumption the disclosed system, device and method can be configured to be implemented using fixed point arithmetic as opposed to using floating point arithmetic. Conversion of numerical processing using floating point arithmetic to fixed point arithmetic requires care with respect to overflow and underflow in computations. However, after such conversion is performed successfully, the processing workload can be reduced by replacing floating point multiplication operations with single-cycle, 32-bit multiplications, and floating point addition operations with simple, 32-bit additions (or subtractions). Evaluation of the resulting fixed-point version of the disclosed method shows that the square root function, which is executed four times in each cycle of the disclosed method, consumes many processing cycles. Using a standard square root function call, which is typically included in a library of digital signal processing (DSP) functions, to apply the square root hardware accelerator can further reduce processing cycle count. Another optimization can be to reduce the cycle count of the Euler angles computation by applying a hardware accelerator for the inverse sine function. Because the inverse tangent function can be expressed in terms of the inverse sine and square root operations, using the hardware accelerators for the computations reduces computational workload, power consumption, and processing time per iteration. Thus the processing cycle count of the disclosed nine-dimensional sensor fusion method can be reduced by implementing a fixed point version of the process that takes advantage of available hardware accelerators. Reduction of cycle count leads to lower energy, as the energy that is used for executing the algorithm is proportional to the required performance.

In an embodiment, position sensors 308 are used in both the barrel 220 of the testing tool 110 and in the plunger 210 of the testing tool 110 to determine the position of the plunger 210 relative to the barrel 220 of the testing tool 110. This information can be used to indicate distal travel movement of the plunger 210 in the testing tool 110 during simulated injection. The distal travel movement can represent a volume of fluid that would be injected, and therefore the distal travel movement can be used to determine a measure of the injection trainee's performance.

An embodiment of the disclosed system, device and method to determine the position and orientation of the testing tool 110, relative to the injection apparatus 105, during injection training includes the use of one or more retro-reflectors attached to the testing tool 110 in association with an optical tracking system. A retro-reflector (sometimes called a retroflector or cataphote) is a device or surface that reflects light back to its source with a minimum of scattering. In a retro-reflector, an electromagnetic wave front is reflected back along a vector that is parallel to, but opposite in direction from, the wave's source. The angle of incidence at which the device or surface reflects light in this way is greater than zero, unlike a planar mirror, which reflects an electromagnetic wave (such as light) only if the mirror is exactly perpendicular to the wave front, having a zero angle of incidence. The retro-reflectors are locatable by an optical tracking system that can operate in, for example, the infrared (IR) range. The retro-reflectors can be positioned on the external surface of the testing tool 110 for use with optical tracking systems that operate by use of infrared illumination. This type of optical tracking allows for the triangulation of energy reflected from the retro-reflectors to determine the testing tool's 110 position in three-dimensional space. In an embodiment, alignment of the needle tip 233 with the injection apparatus 105 can be accomplished by touching the needle tip 233 to a known location on the injection apparatus 105, such as calibration points 1204.

Figure 14B:
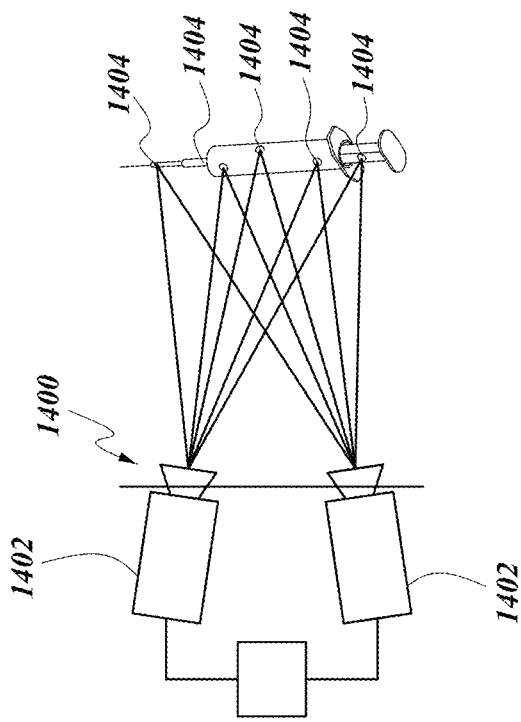
FIG. 14B is simplified perspective view of an exemplary optical tracking system sensing reflected light from testing tool according to an embodiment of the disclosed injection training system.
Figure 14A:
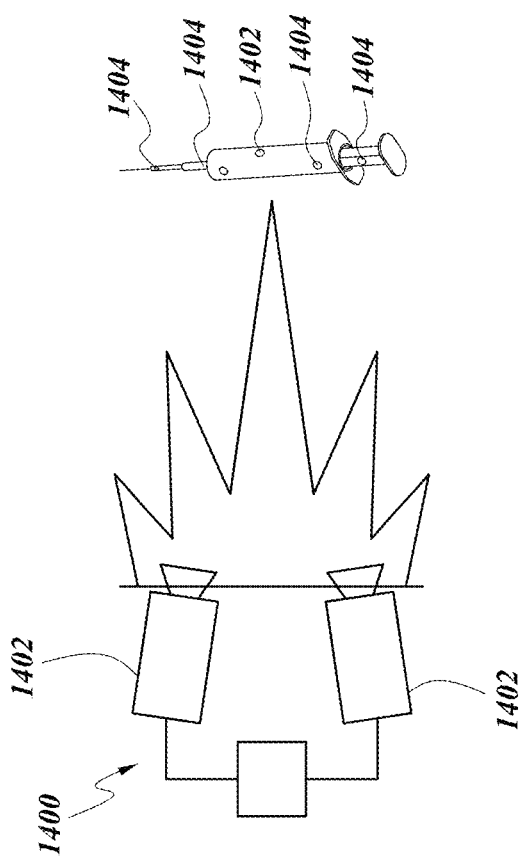
FIG. 14A is simplified perspective view of an exemplary optical tracking system illuminating a testing tool according to an embodiment of the disclosed injection training system.

FIGS. 14A and 14B are perspective views of an exemplary optical tracking system 1400. Optical tracking is a 3D localization technology that monitors a defined measurement space using two or more light sensors 1402, such as, by way of non-limiting example, cameras. In an embodiment, each light sensor 1402 is equipped with an infrared (IR) pass filter (not shown) in front of the lens, and a ring of IR light emitting diodes (not shown) around the lens to periodically illuminate the measurement space of the optical tracking system 1400 with IR light, as illustrated in FIG. 14A. Reflections from markers 1404 on the testing tool 110 are sensed by the light sensors 1402, and the sensed information is processed by the optical tracking system 1400 to determine the position and orientation of the testing tool 110 in three-dimensional space. Examples of optical tracking systems 1400 are described in a paper entitled "PST iris: Instruction Manual," published by Personal Space Technologies B.V, and in International Patent Application Number PCT/NL2009/050607, having International Publication Number WO 2011/043645A1, published on Apr. 14, 2011, which are incorporated by reference herein in their entirety.

Computer stereo vision is the extraction of 3D information from digital images, such as obtained by a charge-coupled device camera. By comparing information about a scene from two vantage points, 3D information can be extracted by examination of the relative positions of objects in the two panels. In traditional stereo vision, two cameras, displaced horizontally from one another are used to obtain two differing views on a scene, in a manner similar to human binocular vision. By comparing these two images, the relative depth information can be obtained, in the form of disparities, which are inversely proportional to the differences in distance to the objects. To compare the images, the two views are superimposed in a stereoscopic device. In camera systems, several pre-processing steps are required. The image is removed of distortions, such as barrel distortion to ensure that the observed image is a pure projection. The image is projected back to a common plane to allow comparison of the image pairs, known as image rectification. An information measure which compares the two images is minimized. This gives the best estimate of the position of features in the two images, and creates a disparity map. Optionally, the disparity as observed by the common projection, is converted back to a height map by inversion. Using a correct proportionality constant, the height map can be calibrated to provide precise distances. Active stereo vision is a form of stereo vision which actively employs a light, such as an infrared light source, to simplify the stereo matching problem. An examples of a stereo vision system and processing method is disclosed in U.S. Pat. No. 8,208,716B2, issued on Jun. 26, 2012, which is incorporated by reference herein in its entirety.

Objects to be tracked, such as the testing tool 110, can be equipped with retro-reflective markers 1404 that reflect the incoming IR light back to the light sensors 1402. The IR reflections are detected by the light sensors 1402 and then internally processed by the optical tracking system 1400. The optical tracking system 1400 calculates the 2D marker position, in image coordinates, with high precision. Using at least two light sensors 1402, the 3D position of each marker 1404 can be derived, as described above. The 3D position can be measured by using a single marker 1404 in the measurement space; however, to be able to also measure the orientation of an object (or to track multiple objects simultaneously), multiple markers 1404 must be placed on each object. Such a configuration can be created by affixing markers 1404 randomly onto the object, making sure at least two markers 1404 can be seen from each angle of the object that the user desires to be detected. By establishing a model of the configuration of each object, the optical tracking system 1400 can distinguish between objects and can determine the 3D position and orientation of each object.

Optical tracking systems 1400 offer some advantages over other approaches to measure and determine the 3D position and orientation of an object in three-dimensional space. For example, optical tracking is less susceptible to noise from the environment, such as, for instance, ferromagnetic metal in the environment which can influence the accuracy of the measurements of magnetic tracking systems. Additionally, optical tracking does not suffer from drift problems experienced in, for instance, inertial sensors, which cause measurements to slowly deviate from actual values, for which compensation techniques must be applied. Optical tracking also allows for many objects to be tracked simultaneously. Optically tracked devices can be lightweight and they do not require wires or power. As such, users are neither hampered by wires nor limited in their manipulation of the object.

Figure 14C:
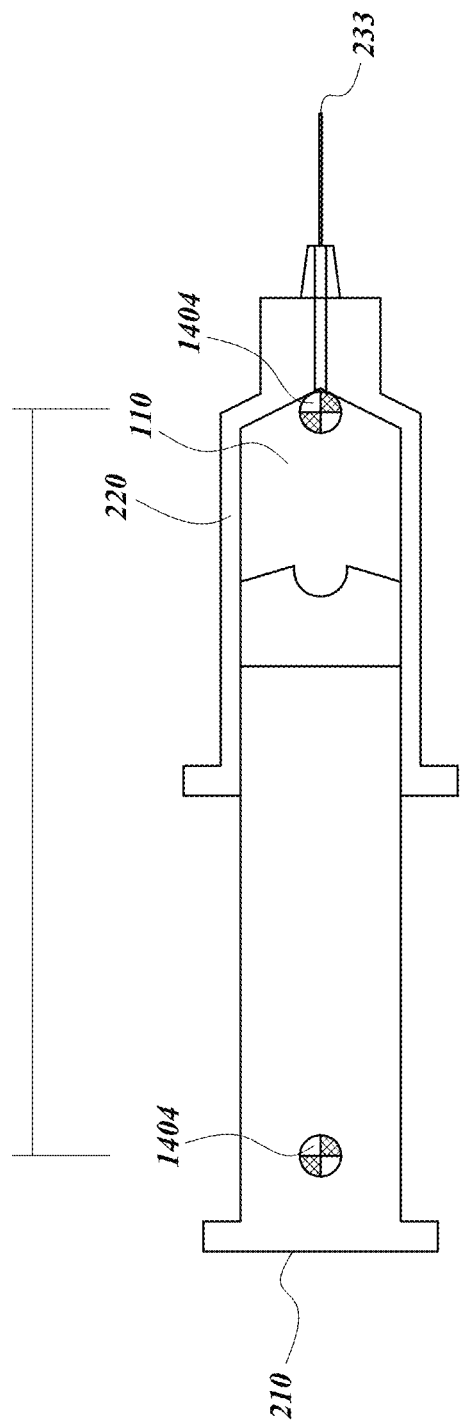
FIG. 14C illustrates a testing tool configured with multiple markers according to an embodiment of the disclosed injection training system.

FIG. 14C illustrates a testing tool 110 configured with multiple markers 1404, in accordance with an embodiment of the present disclosure. In an embodiment, an optical tracking system 1400 measures the 3D positions of markers 1404, such as, for example, retro-reflectors, affixed to the testing tool 110. The markers 1404 can be active or passive. Using this information, the optical tracking system 1400 can determine the position and orientation of the marked testing tool 110 within a specific field of view defined by the optical tracking system. The optical tracking system 1400 can be a self-contained, integrated system that does not require external processing or calibration components. The optical tracking system 1400 can be connected to the user interface/display device 140 via a wired or by a wireless communication scheme. The optical tracking system 1400 can deliver 3D position and orientation measurement of the testing tool 110 to the interface unit/display device 140. Advantageously, the disclosed optical tracking system 1400 delivers fully-processed position and orientation data to the user interface/display device 140, thereby freeing up the processing capability of the user interface/display device 140 for other computationally-intensive activities, such as, for example, processing and rendering of a digital model representative of the injection apparatus 105 and the testing tool 110 during injection training.

Figure 14D:
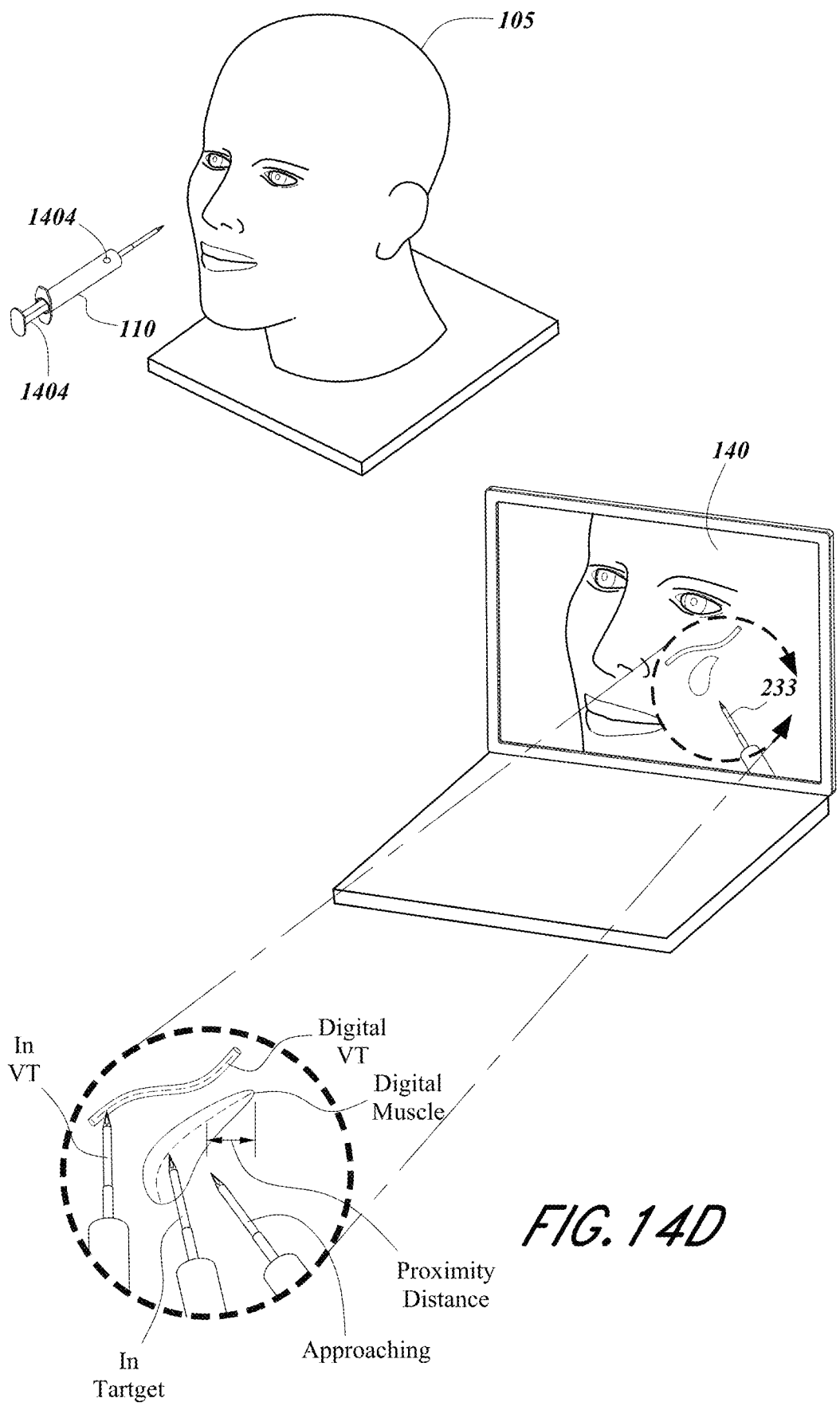
FIG. 14D illustrates aspects of the user interface/display device according to an embodiment of the disclosed injection training system.

FIG. 14D illustrates, among other things, aspects of the user interface/display device 140 according to an embodiment of the disclosed injection training system 100. Shown in magnified perspective are examples of how the user interface/display device 140 can graphically display, either during the injection training or afterwards, the location of the needle tip 233 as it penetrates the injection apparatus 105. The user interface/display device 140 illustrates portions of the anatomy in the vicinity of the injection site. In particular, vital tissue (VT), and muscle are represented digitally on the user interface/display device 140. Advantageously, the user can view a target site, a proximity to the target site, and nearby vital tissues or structures. In some embodiments, visual and/or aural signals are delivered to the trainee as indications of the needle tip's 233 proximity to the target site. During an injection, for example, the display can graphically illustrate the different skin and tissue layers as the needle tip 233 penetrates each layer. For example, this can be done by graphically peeling back the layers as a new layer is penetrated. For training purposes, the different layers can be labeled or provided with different textures or colors to indicate a new layer is shown.

Figure 15A:
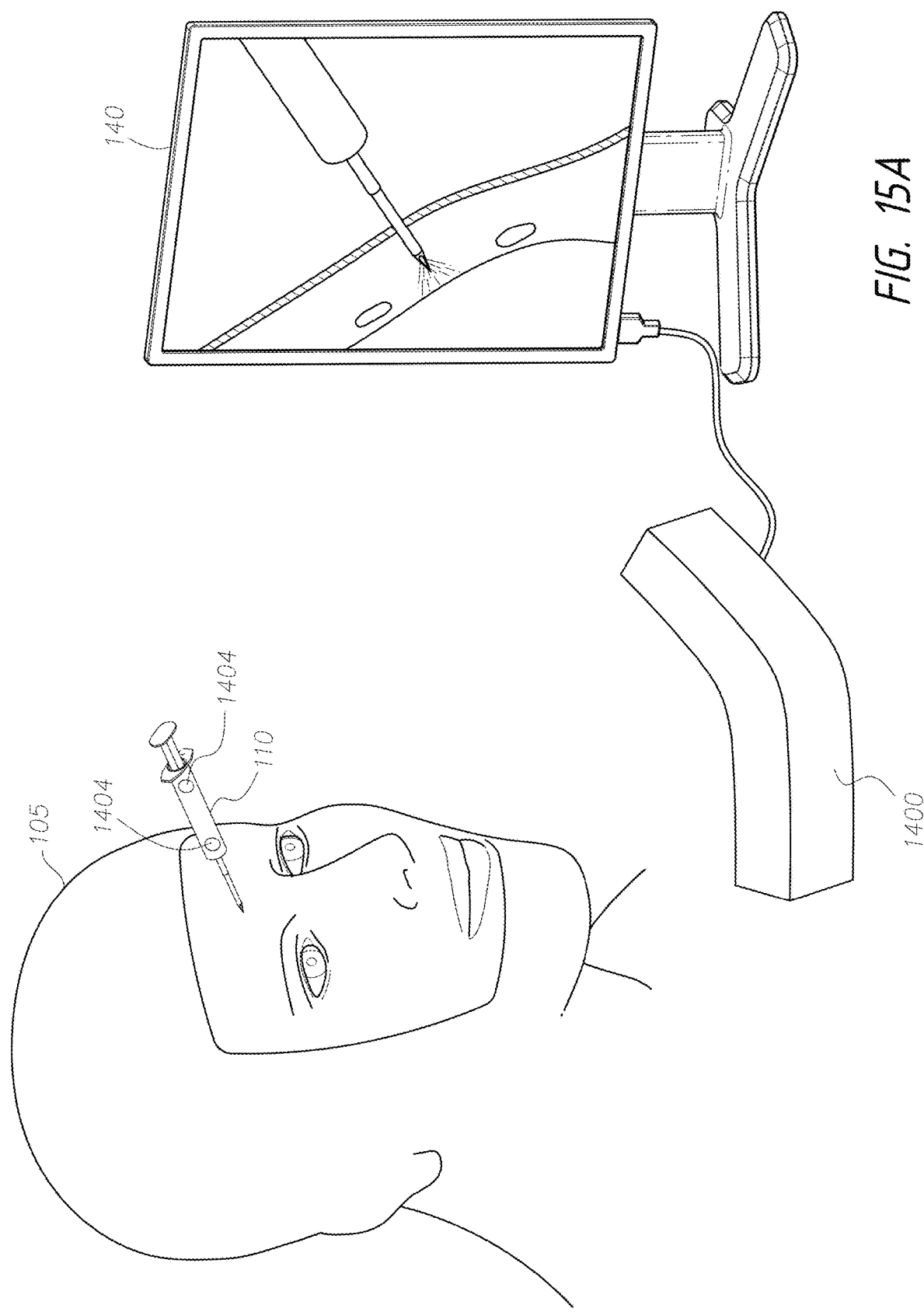
FIG. 15A illustrates an embodiment of an injection training system comprising an injection apparatus, a testing tool, an output device and an optical tracking system, in accordance with an embodiment of the present disclosure.

In an embodiment, a single optical tacking system 1400 can track the testing tool 110 in an injection training environment, as illustrated in FIG. 15A. In an embodiment, multiple optical tracking systems 1400 can be coupled together to extend the workspace environment or to reduce issues due to the line-of-sight requirement of the optical tracking system 1400, as illustrated in FIG. 15B. In an embodiment, the optical tracking system 1400 can be configured with different optics configurations to adapt the field of view and the performance characteristics of the optical tracking system 1400 to the intended environment and application. Illustratively, optics with a higher field of view result in a wider tracking area closer to the system, whereas optics with a lower field of view provide a narrower, but longer, tracking area.

The optical tracking system 1400 can use tangible, wireless devices for 3D interaction and 3D measurement, such as the testing tool 110. In an embodiment, the position and orientation (sometimes referred to as the "pose") of the testing tool 110 can be reconstructed with millimeter accuracy. Advantageously, the optical tracking system 1400 can be based on infrared lighting, which can reduce the interference of visible light sources from the environment. This allows the optical tracking system 1400 to be used under normal, ambient working conditions without requiring controlled lighting. The testing tool 110, and the injection apparatus 105, can be tracked by applying retro-reflective markers 1404 to their external surfaces. The optical tracking system 1400 employs these markers to recognize different objects and to reconstruct their poses. In an embodiment, and by way of non-limiting illustration, the optical tracking system 1400 reconstructs the pose of the testing tool 110, and optionally, of the injection apparatus 105, at an adjustable sampling frequency with a maximum of 120 times per second. One skilled in the art will appreciate that other sampling frequencies can be used without departing from the scope of the present disclosure. The optical tracking system 1400 can be triggered externally, such that it can be synchronized to external clock sources. This can, for instance, be used to prevent interference between the internal infrared flash and shutter glasses that are synchronized to a 3D monitor, such as the user interface/display device 140, using an infrared signal.

In an embodiment, tracking devices comprise physical objects, such as the testing tool 110 and the injection apparatus 105, that can be recognized by the optical tracking system 1400 and of which the 3D position and orientation can be measured. In an embodiment, such devices can be used to measure the spatial coordinates of objects, or for instance, to interact with virtual 3D objects in an application. Illustratively, just as a mouse can be used to position a pointer in two-dimensional space, so too can a tracking device be used to position an object in three-dimensional space, with six degrees of freedom. The 3D position and orientation (pose) of a tracking device, such as the testing tool 110, is optically tracked, ensuring wireless operation. Retro-reflective markers 1404 can be applied to objects, such as the testing tool 110 and the injection apparatus 105, to transform them into tracking devices. The tracking system uses these markers 1404 to recognize devices and to reconstruct each pose. In order for the optical tracking system 1400 to be able to determine the position and orientation of a tracking device, at least four markers 1404 need to be applied. The size of the markers 1404 helps to determine the optimal tracking distance. The optical tracking system 1400 supports flat retro-reflective markers 1404 for the construction of tracking devices. Such flat retro-reflective markers 1402 do not hamper manipulation.

In an embodiment, the markers 1404 are locatable by tracking systems, devices, and methods that can operate in the radio frequency (RF) range. The markers 1404 can be positioned on the interior of the testing tool 110 for tracking systems 1400 that operate through use of RF illumination, such as the technology known as radio-frequency identification (RFID). Advantageously, the RF energy is able to be transmitted through the tissue of the injector's hand, arm and other portions of the injector's body that may obstruct the required line-of-site view between an optical tracking system 1400 and the testing tool 110 during injection training, when implemented using optical tracking systems 1400 based on infrared illumination.

In an embodiment, the reflective markers 1404 comprise corner reflectors. Corner reflectors can operate in a wide range of electromagnetic frequencies including the infrared and the radio spectrums. A corner reflector is a retro-reflector comprising three mutually perpendicular, intersecting flat surfaces. The corner reflector reflects waves back directly towards the source, but shifted (translated). The three intersecting surfaces often have square shapes. Optical corner reflectors, called corner cubes, made of three-sided glass prisms, are used in surveying and laser range-finding. The incoming ray is reflected three times, once by each surface, which results in a reversal of direction. The three corresponding normal vectors of the corner's perpendicular sides can be considered to form a basis (a rectangular coordinate system) (x, y, z) in which to represent the direction of an arbitrary incoming ray, [a, b, c]. When the ray reflects from the first side, say x, the ray's x component, a, is reversed to −a while the y and z components are unchanged, resulting in a direction of [−a, b, c]. Similarly, when reflected from side y and finally from side z, the b and c components are reversed. So the ray direction goes from [a, b, c] to [−a, b, c] to [−a, −b, c] to [−a, −b, −c] and it leaves the corner reflector with all three components of direction exactly reversed. The distance traveled, relative to a plane normal to the direction of the rays, is also equal for any ray entering the reflector, regardless of the location where it first reflects.

In an embodiment, the optical tracking system 1400 views the testing tool 110 and the needle tip 233 as it approaches and penetrates the injection apparatus 105. The optical tracking system 1400 can operate in the visual and infrared spectrums. For optical tracking systems 1400 using the infrared spectrum, an improvement in resolution and differentiation is available by altering the temperature of the testing tool 110 and/or the needle tip 233 to be different (hotter or colder) than ambient temperature. Infrared thermography (IRT), thermal imaging, and thermal video are examples of infrared imaging science. Thermographic cameras detect radiation in the infrared range of the electromagnetic spectrum (roughly 9,000-14,000 nanometers or 9-14 μm) and produce images of that radiation, called thermograms. Since infrared radiation is emitted by all objects above absolute zero according to the black body radiation law, thermography makes it possible to see one's environment with or without visible illumination. The amount of radiation emitted by an object increases with temperature; therefore, thermography allows one to see variations in temperature. When viewed through a thermal imaging camera, warm objects stand out well against cooler backgrounds.

The testing tool 110 and needle tip 233 can be clearly resolved against the ambient temperature background when using thermal imaging. In an embodiment, the 3D sensor(s) 502 from the interior of the injection apparatus 105 can be configured to sense both light emitting from the testing tool 110 and thermal energy emitted from the testing tool 110 and/or needle tip 233 by use of infrared, or other forms of thermal imaging. Multiple methods for achieving temperature variation of the testing tool 110 relative to ambient temperature can be used, including, without limitation, resistive heating on the testing tool 110 interior with conductive heat transfer to the hollow needle 232, and routing gas of a controlled temperature through a tube into the testing tool 110 interior and exhausting the gas through the needle tip 233. In an embodiment, thermal imaging is available by including temperature markers on the injection apparatus 105 to be viewable by a the optical tracking system 1400, which can support accurate resolution of the testing tool's 110 position relative to the injection apparatus 105. In an embodiment, the depth of penetration of the needle tip 233 into the injection apparatus 105 can be determined by measuring the length of the needle 232 remaining exterior to the injection apparatus 105, thereby exposed to the view of the optical tracking system 1400. By knowing the orientation and position of the testing tool 110 relative to the injection apparatus 105, along with the measured length of the needle 232 remaining exterior to the injection apparatus 105, the depth of penetration of the needle tip 233 in the injection apparatus 105 may be determined.

In an embodiment, position information provided by the 3D sensor(s) 502 and the optical tracking system 1400 can be combined to determine the position and orientation of the testing tool 110 and the needle tip 233 relative to the injection apparatus 105 during injection training. Combination of position data corresponding to the light emitting needle tip 233 as the needle tip 233 passes through the opaque layer of artificial skin, as sensed by the 3D sensor(s) 502 from the interior of the injection apparatus 105, with the length of the needle 232 remaining exterior to the injection apparatus 105, as sensed by the optical tracking system 1400, can be combined to determine the position and orientation of the testing tool 110 and the needle tip 233 relative to the injection apparatus 105.

An injection training system has been disclosed in detail in connection with various embodiments. These embodiments are disclosed by way of examples only and are not to limit the scope of the claims that follow. One of ordinary skill in the art will appreciate from the disclosure herein any variations and modifications.

Terminology/Additional Embodiments

The term "injection" as used herein includes it usual and customary meaning of an injection, but is also to be interpreted broad enough to encompass, for example, the insertion of a catheter device or the use of simple needles, such as would be used in an acupuncture therapy. The techniques involved, particularly a camera embedded in a model of a living subject and a tool with a light emitter can be applied to any therapeutic procedure. For example, the tool can be a catheter and the procedure can be a minimally invasive procedure requiring the catheter to be located in a particular location.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such embodiment decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

What is claimed is:
1. An injection system, the system comprising:
a syringe having a syringe body and a plunger, the plunger configured to move relative to the syringe body, the syringe body comprising a body portion having a proximal end and a distal end and an internal barrel cavity between the proximal and distal ends, a flange portion disposed at or near the proximal end, and a needle coupling portion disposed at or near the distal end, the needle coupling portion configured to be coupled to a needle; and one or more sensors configured to measure injection information about an injection procedure performed using the injection system, the one or more sensors comprising a plunger shaft displacement sensor configured to measure positional displacement of a shaft of the plunger, wherein the one or more sensors are coupled to a portion of the syringe that is outside the internal barrel cavity so that the internal barrel cavity is available to hold a volume of a therapeutic agent, the syringe configured to deliver the therapeutic agent through the needle.

2. The injection system of claim 1, wherein the injection information comprises one or more of:

force and/or pressure of injection;
angle of injection;
depth of injection; and/or
location of injection.

3. The injection system of claim 1, further comprising at least first and second cameras spaced apart from each other, wherein the at least first and second cameras are configured to detect a location of the syringe relative to the at least first and second cameras.

4. The injection system of claim 3, further comprising a training apparatus configured to receive an injection using the syringe, wherein the at least first and second cameras are located within a cavity of the training apparatus.

5. The injection system of claim 4, wherein the syringe body further comprises a light source located at or near the distal end of the body portion.

6. The injection system of claim 5, wherein the syringe comprises the needle, the needle having an optic fiber disposed within a lumen of the needle, the optic fiber terminating distally at or near a tip of the needle.

7. The injection system of claim 1, wherein the one or more sensors comprise a force sensor, a pressure sensor, and/or a position sensor.

8. The injection system of claim 7, wherein the one or more sensors comprise the position sensor, the position sensor including an inertial measurement unit.

9. The injection system of claim 1, further comprising a rechargeable battery configured to provide power to the one or more sensors.

10. The injection system of claim 9, further comprising a light source, wherein the rechargeable battery is configured to power the light source.

11. The injection system of claim 9, further comprising one or more electrical contacts coupled to the rechargeable battery, the one or more electrical contacts accessible from outside the syringe.

12. The injection system of claim 11, further comprising a charging base, the charging base having one or more electrical connectors configured to contact the one or more electrical contacts when the syringe is docked onto the charging base.

13. The injection system of claim 12, wherein the charging base comprises a cradle contoured to accommodate the syringe.

14. The injection system of claim 1, comprising a friction device configured to act against the plunger to simulate a viscosity of a medication.

15. The injection system of claim 1, wherein at least some of the one or more sensors are located on at least one circuit board.

16. The injection system of claim 15, wherein the at least one circuit board comprises a first circuit board and a second circuit board, the first and second circuit boards being electrically coupled.

17. The injection system of claim 1, wherein the plunger shaft is collapsible, and wherein the plunger shaft displacement sensor is configured to measure a collapsible motion of the plunger shaft.

18. A method of improving injection training using a processor of an injection system, the injection system further comprising a syringe configured to perform an injection, the method comprising:

receiving sensor outputs from one or more sensors coupled to the syringe, the syringe comprising a syringe body including a body portion having a proximal end and a distal end and an internal barrel cavity between the proximal and distal ends, a flange portion disposed at or near the proximal end, and a needle coupling portion disposed at or near the distal end, the needle coupling portion configured to be coupled to a needle, the syringe further comprising a plunger, the plunger configured to move relative to the syringe body, wherein the one or more sensors are coupled to a portion of the syringe that is outside the internal barrel cavity so that the internal barrel cavity is available to hold a volume of a therapeutic agent, the syringe configured to deliver the therapeutic agent through the needle;

determining, based at least in part on the sensor outputs, injection information about an injection procedure performed using the injection system, wherein the injection information comprises a displacement of a shaft of the plunger; and outputting the injection information, through wireless electrical communications, to a display device.

19. The method of claim 18, wherein the one or more sensors comprise a force sensor, the method further comprising determining a force applied to the plunger of the syringe based at least in part on sensor inputs from the force sensor.

20. The method of claim 18, further comprising receiving outputs from at least two cameras of the injection system, the at least two cameras being spaced apart from each other, the outputs related to a three-dimensional position information of the syringe, wherein the determining is based at least in part on the outputs from the at least two cameras.

21. The method of claim 20, wherein the one or more sensors comprise a position sensor, the syringe further comprising a light source, and the at least two cameras located within a cavity of a training apparatus configured to receive the injection, wherein the determining further comprises obtaining the three-dimensional position information of the syringe by combining the sensor outputs from the position sensor and the outputs from the at least two cameras detecting light emitted from the light source.

* * * * *

UNITED STATES PATENT AND TRADEMARK OFFICE
CERTIFICATE OF CORRECTION

PATENT NO. : 10,896,627 B2
APPLICATION NO. : 15/886363
DATED : January 19, 2021
INVENTOR(S) : Clark B. Foster It is certified that error appears in the above-identified patent and that said Letters Patent is hereby corrected as shown below:

On the Title Page

In Column 1, item (73), Assignee, Line 1, delete "Truinjet" and insert --Truinject--.

On page 5, in Column 1, item (56), Other Publications, Line 59, delete "invensese" and insert --invensense--.

In the Specification

In Column 23, Line 63, delete "1362," and insert --13B2,--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*